US007029845B2

(12) United States Patent
Nassif et al.

(10) Patent No.: US 7,029,845 B2
(45) Date of Patent: Apr. 18, 2006

(54) **DNAS AND PROTEINS OR PEPTIDES SPECIFIC TO BACTERIA OF THE SPECIES *NEISSERIA MENINGITIDIS*, PROCESSES FOR OBTAINING THEM AND THEIR BIOLOGICAL USES**

(75) Inventors: Xavier Nassif, Paris (FR); Colin Tinsley, Paris (FR)

(73) Assignees: Institut National de la Sante et de la Recherche Medicale (I.N.S.E.R.M.), Paris (FR); Max-Planck-Gesellschaft zur Forderung des Wessenschaften E.V., Munich (DE); Smithkline Beecham, Brentford (GB)

( * ) Notice: Subject to any disclaimer, the term of this patent is extended or adjusted under 35 U.S.C. 154(b) by 223 days.

(21) Appl. No.: 09/928,457

(22) Filed: Aug. 14, 2001

(65) Prior Publication Data

US 2002/0164603 A1 Nov. 7, 2002

Related U.S. Application Data

(63) Continuation of application No. 09/214,759, filed as application No. PCT/FR97/01295 on Jul. 11, 1997, now abandoned.

(30) Foreign Application Priority Data

Jul. 12, 1996 (FR) .............................. 96 08768

(51) Int. Cl.
*C12Q 1/68* (2006.01)

(52) U.S. Cl. ..................... 435/6; 435/183; 435/252.3; 435/320.1; 435/69.3; 536/23.7; 536/24.32; 536/24.33; 514/44

(58) Field of Classification Search ............. 435/6, 435/91.2, 252.3, 320.1, 183, 69.3; 514/44; 536/23.7, 24.32, 24.33, 23.1, 23.2, 23.3
See application file for complete search history.

(56) References Cited

U.S. PATENT DOCUMENTS 5,445,933 A * 8/1995 Eadie et al. ................... 435/6
5,747,252 A * 5/1998 Yang et al. .................... 435/6

FOREIGN PATENT DOCUMENTS

| EP | 0 301 992 | 2/1989 |
| EP | 0 337 896 | 10/1989 |
| EP | 0 452 596 | 10/1991 |
| EP | 548012 A | of 1993 |
| EP | 9407356 A | of 1993 |
| WO | WO 88/03957 | 6/1988 |
| WO | WO 90/15621 | 12/1990 |
| WO | WO 94/05703 | 3/1994 |

OTHER PUBLICATIONS

Dempsey, Jo Ann Fanney et al, Journal of Bacteriology, Nov. 1995, vol. 177(22), pp. 6390–6400.*
Wolff, K et al, FEMS microbiology letters, Jan. 15, 1995, vol. 125(2–3), pp. 255–263.*
Martin, Pr et al, accession No. M65216, Sequence analysis and complemetation studies of the argJ gene encoding ornithine acetyltransferase from *Neisseria gonorrhoeae*, created date in EMBL May 2, 1992.*
Gaher, M et al, A physical and genetic map of *Neisseria meningitidis* B1940. Molecular Microbiology, Jan. 1996, vol. 19(2), pp. 249–259.*
Dempsey, Jo Ann F. e tal, Journal of Bacteriology, Apr. 1994, vol. 176(7), Location of Genetic Markers on the Physical Map of Chromosome of *Neisseria gonorrhoeae* FA 1090.*
Serizawa, H et al, Nucleic Acids Research, vol. 15(3), pp. 1153–1163, 1987.*
Welcher, Andrew A et al, Nucleic acids Research, vol. 14(24) pp. 10027–10044, Dec. 22, 1986.*
Gaher, Martin et al, Molecular Microbiology, vol. 19(2), pp. 249–259, 1996.*
Swanson, J et al, Infection and Immunity, vol. 10(3), pp. 633–644, Sep. 1974.*
Zhou et al, "Sequence diversity with in the argF, fbp and recA genes of natural isolates of *Neisseria meningitidis*: interspecies recombination within the argF gene", Mol Microbiol. Aug. 1992, 6 (15), pp. 2135–2146, England.
Devi et al, "Antibodies to poly[(2——8)-alpha-N-acetyl-neuraminic acid] and poly[(2——9)-alpha-N-acetyl-neuraminic acid] are elicited by immunization of mice with *Escherichia coli* K92 conjugates: potential vaccines for group B and C meningococci and *E. coli* K1.", Proc Natl Acad Sci USA, Aug. 15, 1991, 88 (16, pp. 1715–9.
Wolff et al, "Identificaiton and characterization of specific sequences encoding pathogenicity associated proteins in the genome of commensal *Neisseria species*", FEMS Microbiol Lett, Jan. 15, 1995, 125 (2–3), pp. 255–263, Netherlands.
Petering et al, "Genes associated with meningococcal capsule complex are also found in *Neisseria gonorrhoeae*", J Bacteriol, Jun. 1996, 178 (11) pp. 3324–5, United States.

(Continued)

*Primary Examiner*—Lynette R. F. Smith
*Assistant Examiner*—Ginny Allen Portner
(74) *Attorney, Agent, or Firm*—Nixon & Vanderhye P.C.

(57) ABSTRACT

The DNA of the invention are characterised in that they concern the whole or part of genes, with their reading frame, to be found in *Neisseria meningitidis*, but not in *Neisseria gonorrhoeae*, or in *Neisseria lactamica* except the genes involved in the biosynthesis of the polysaccharide capsule, frp A, frp C, opc, por A, rotamase the sequence IC1106, IgA protease, pilline, pilC, transferrin binding proteins and opacity proteins. The invention also concerns the polypeptides corresponding to these DNA and the antibodies directed against these polypeptides. It is applicable in the prevention and the detection of meningococcus induced infections and meningitis.

8 Claims, 9 Drawing Sheets

OTHER PUBLICATIONS

Figure 2:
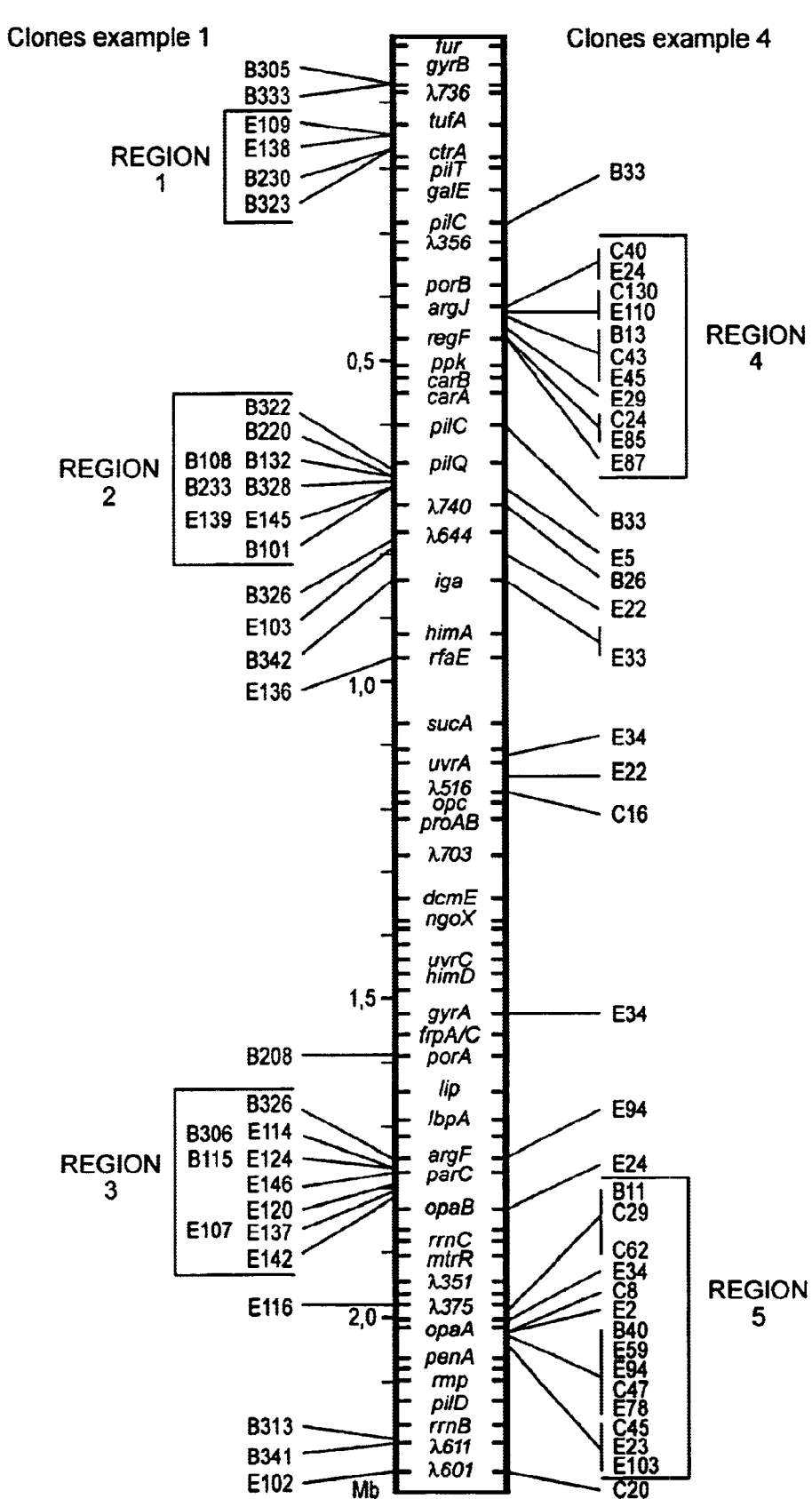

Frosch et al, "Evidence for a common molecular origin of the capsule gene loci in gram–negative bacteria expressing group II capsular polysaccharides", Mol Microbiol, May 1991, 5 (5), pp. 1251–1263, England.

Frosch et al, "Phospholipid substitution of capsular polysaccharides and mechanisms of capsule formation in *Neisseria meningitidis*", Mol Microbiol, May 1993, 8 (3), pp. 483–493, England.

Frosch et al, "Conserved outer–membrane protein of *Neisseria–meningitides* involved in capsule expression" Infection and Immunity, 1992, 60, pp. 798–803.

Strathdee et al, "Identification of Epidemiologic markers for *Neisseria–meningitidis* using difference analysis", GENE, 1995, 166, pp. 105–110.

Lauerman et al, "Avian mycoplasma identification using polymerase chain reactiom amplicon and restriction fragment length polymorphism analysis", Avian Dis, Oct.–Dec. 1995, 39, (4) pp. 804–811. United States.

Zhang, Q et al, Antimicrobiol Agents Chomother., vol. 34(8), pp. 1523–1528, Aug. 1990.

Knight et al., "Identification and Characterization of a Novel Insertion Sequence, IS 1106, Downstream of the porA Gene in B15 *Neisseria Meningitidis*", Molecular Microbiology (1992) 6(11), pp. 1565–1573.

Dempsey, J. et al, Journal of Bacteriology, vol. 177, No. 22, Nov. 1995, pp. 6390–6400 (Nov. 1995).

Virji, M. et al, Molecular Microbiology, vol. 6(19), Oct. 1992, pp. 2785–2795 (abstract).

Virji, M. et al, Molecular Microbiology, Vo. 10(3), pp. 499–510, Nov., 1993 (abstract).

Frosch et al., "Phospholipid Substitution of Capsular Polysaccharides and Mechanisms of Capsule Formation in *Neisseria Meningitidis*", Molecular Microbiology (1993)8(3), pp. 483–493.

Schutte et al., "Isolation of YAC Insert Sequences by Representational Difference Analysis", Nucleic Acids Research, 1995, vol. 23, No. 20, pp. 4127–4133.

Lisitsyn et al., "Cloning the Differences Between Two Complex Genomes", Science, vol. 259, Feb. 12, 1993, pp. 946–951.

Tinsley et al., "Analysis fo the Genetic Difference between *Neisseria Meningitidis* and *Neisseria Gonorrhoeae*: Two closely related Bacteria Expressing two Differenct Pathogenicities", Proc. Natl. Acad, Sci., USA, vol. 93, pp. 11109–11114, Oct. 1996 Microbiology.

Weiss, E et al, The immune system and infectious diseases, 1975, vol. 4, pp. 423–440 (abstract).

Moore, Td et al, Infection Immunity, vol. 63(4), pp. 1603–1607 Apr., 1995 (abstract).

Bautsch, W, FEMS Microbiology Lett., Mar. 1, 1993, vol. 107 (2–3), pp. 191–197.

Versalovic, J et al, Methods in Molecular and Cellular Biology, vol. 5(2), pp. 96–104, 1995.

\* cited by examiner

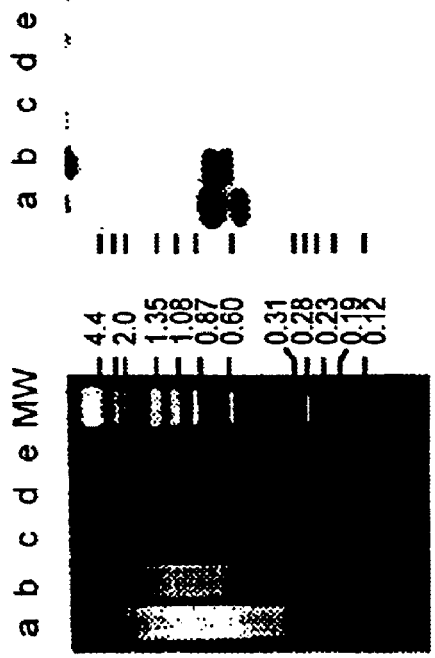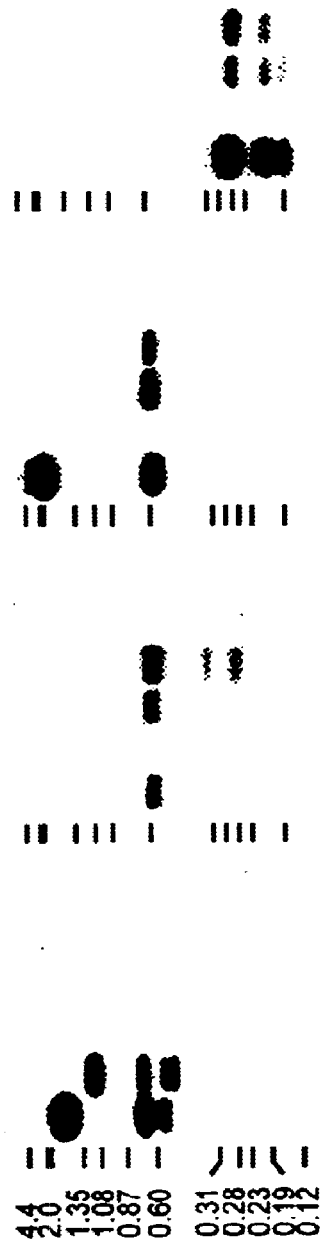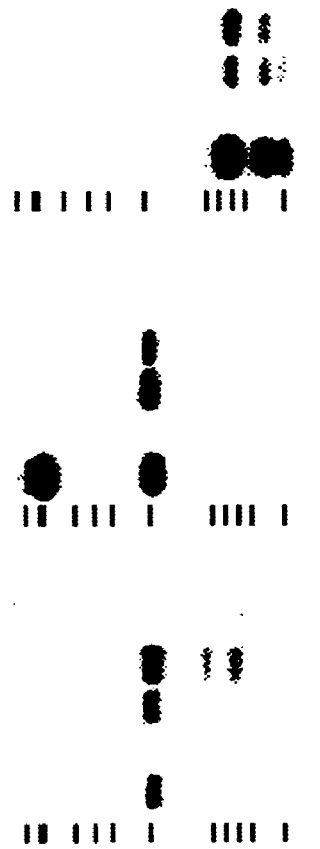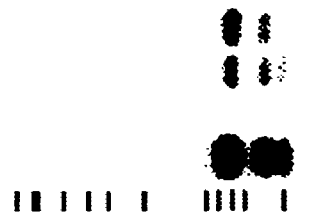

DNAS AND PROTEINS OR PEPTIDES SPECIFIC TO BACTERIA OF THE SPECIES *NEISSERIA MENINGITIDIS*, PROCESSES FOR OBTAINING expression products are interpreted on the basis of identical hybridization conditions (16 h at 65° C., with NaPO$_4$ 0.5 M, pH 7.2; EDTA-Na 0.001 M, 1%, 1% bovine serum albumin and 7% sodium dodecylsulphate) using the same probe and the same labelling intensity of the probe, the same amount of chromosomal DNA and the same comparison element (chromosomal DNA of the homologous strain).

It is therefore considered that the DNA is present if the signal obtained with the probe is practically the same as that obtained with the reference strain.

Conversely, it is considered that the DNA is absent if this signal appears very weak.

A second consideration of the pathogenicities of Nm and Ng leads to taking into account their common capacity for colonization and penetration of the mucosa, and then invasion of the subepithelial space of the latter. It is highly probable that this process involves virulence factors common to the two pathogens. In this respect, it is known that a certain number of virulence factors have already been identified in Nm and in Ng, such as the pili proteins, PilC, the opacity proteins, the IgA proteases, the proteins for binding to transferrin and to lactoferrin, and the lipooligosaccharides.

The approach of the inventors is thus extended to investigation of the Nm regions which are specific to Nm and Ng but absent from the non-pathogenic species Nl, and in a general manner to investigation of the chromosomal regions of the DNAs and their expression products specific to a given species by the means developed in accordance with the invention.

The object of the invention is thus to provide DNAs of Nm specific to its pathogenic potency and means for obtaining them, in particular by formulating banks formed exclusively from these Nm-specific DNAs.

It also provides the products derived from these DNA sequences.

The invention also relates to the utilization of specific and exhaustive characteristics of these banks to formulate tools which can be used, in particular, in diagnostics, treatment and prevention.

The DNAs of the invention are characterized in that they are in all or part genes, with their reading frame, present in *Neisseria meningitidis*, but absent either from *Neisseria gonorrhoeae* and from *Neisseria lactamica*, with the exception genes involved in the biosynthesis of the polysaccharide capsule, frpA, frpC, opc, por A, rotamase, the sequence IS1106 (Accession No. Z 11857 in the EMBL/GenBank/DDBJ Nucleotide Sequence Data Libraries; see Knight et al., 1992, Molecular Microbiology 6(11): 1565–1573), IgA proteases, pilin, pilC, proteins which bind transferrin and opacity proteins.

As stated above, the terms "present" and "absent" are interpreted on the basis of the hybridization conditions used in the Southern blotting described in the examples and referred to above.

It can be seen that these DNAs include variants where these express a function intrinsic to the Nm species, more particularly a phenotype found solely in Nm or in common exclusively with Ng.

According to a main aspect, these DNAs are specific to the pathogenicity of *Neisseria meningitidis*, in spite of the genetic variability of this species.

According to an embodiment of the invention, the said DNAs are specific to Nm, in contrast to Ng.

More particularly, the Nm-specific DNAs are absent from *Neisseria lactamica* and from *Neisseria cinerea.*

Surprisingly, the majority of genetic differences between the strains of meningococci and those of gonococci appear grouped in distinct regions, which are said to correspond to the pathogenicity islets described previously for *E. coli* and *Y. pestis.*

In a preferred embodiment of the invention, these DNA are thus also characterized in that they comprise one or more sequence(s) present on the chromosome of *Neisseria meningitidis* Z2491 between tufA and pilT, or region 1 of the chromosome, and/or the sequence(s) capable of hybridizing with the above sequence(s), with the proviso of being specific to *Neisseria meningitidis.*

"Specific" in the description and the claims means the nucleotide sequences which hybridize only with those of Nm under the hybridization conditions given in the examples and referred to above.

In this respect, it can be seen that, in a general manner, when "all or part" of a sequence is referred to in the description and claims, this expression must be interpreted with respect to the specificity defined above.

Furthermore, all or part of a peptide or a fragment of a peptide or an antibody means a product having the biological properties respectively of the natural peptide or the antibody formed against the peptide.

Genes of the *Neisseria meningitidis* capsule are grouped in region 1.

DNAs of this type have a sequence corresponding in all or part to SEQ ID No. 9, 13, 22 or 30, and/or to any sequence located at more or less 20 kb from these SEQ ID on the chromosome of an Nm strain, and/or have a sequence which is capable of hybridizing with at least a fragment of any one of these sequences.

In another preferred embodiment of the invention, these DNA are also characterized in that they are made up of one or more sequence(s) present on the chromosome of *Neisseria meningitidis* Z2491 between pilQ and λ740, or region 2 of the chromosome, and/or the sequences(s) capable of hybridizing with the above sequence(s), with the proviso of being specific to *Neisseria meningitidis.*

DNAs according to this embodiment have a sequence corresponding in all or part to SEQ ID No. 1, 2, 4, 6, 7, 10, 15, 31 or 34, and/or to any sequence located at more or less 20 kb from these SEQ ID on the chromosome of an Nm strain, and/or have a sequence which is capable of hybridizing with at least a fragment of any one of these sequences.

The invention especially provides all or part of the DNA sequence SEQ ID No. 36 of 15,620 bp, and the sequences corresponding to the open reading frames SEQ ID No. 37, SEQ ID No. 38, SEQ ID No. 39, SEQ ID No. 40, SEQ ID No. 41, SEQ ID No. 42, SEQ ID No. 43, SEQ ID No. 44 and SEQ ID No. 45.

In yet another preferred embodiment of the invention, these DNAs are also characterized in that they are made up of one or more sequence(s) present on the chromosome of *Neisseria meningitidis* Z2491 between argF and opaB, or region 3 of the chromosome, and/or the sequence(s) capable of hybridizing with the above sequence(s), with the proviso of being specific to *Neisseria meningitidis.*

DNAs according to this embodiment are characterized in that they have a sequence corresponding in all or part to SEQ ID No. 8, 21, 23, 25, 26, 28, 29, 32 or 35, and/or to any sequence located at more or less 20 kb from these SEQ ID on the chromosome of an Nm strain, and/or have a sequence which is capable of hybridizing with at least a fragment of any one of these sequences.

Regions 1, 2 and 3 identified above have a high proportion of sequences specific to *Neisseria meningitidis* and also fall within the context of the invention.

Other DNAs representative of the specificity with respect to *Neisseria meningitidis* have one or more sequences which is/are present on the chromosome of *Neisseria meningitidis* Z2491 but are not part of regions 1, 2 and 3 defined above.

Such DNAs comprise one or more sequence(s) corresponding in all or part to SEQ ID No. 3, 5, 11, 12, 14, 16, 18, 19, 20, 24, 27 or 33, and/or to any sequence located at more or less 20 kb from these SEQ ID on the chromosome of an Nm strain, and/or have a sequence capable of hybridizing with such sequences.

Taking into account the uses envisaged in particular, the invention more specifically relates to the above DNAs involved in the pathogenesis of the bacterial organism.

In particular, it provides the DNAs corresponding to at least one of the characterizations given above and coding for a protein exported beyond the cytoplasmic membrane, and/or of which all or part of their sequence corresponds to the conserved region of the said DNAs.

According to another embodiment of the invention, the DNAs are thus common with those of Ng, but are absent from those of Nl.

These are more specifically the DNAs which are present on region 4 (arg J to reg F) or on region 5 (lambda 375 marker to pen A) on the chromosome of Nm Z2491 and/or are capable of hybridizing with the said DNAs present, with the proviso of being specific to Nm and Ng, in contrast to Nl.

"Specific to Nm and Ng in contrast to Nl" means the DNAs which hybridize with the DNAs of Nm and Ng under the hybridization conditions of the examples (see example 4 in particular).

The DNAs of regions 4 and 5 and those capable of hybridizing with these DNAs, with the proviso of expressing the intrinsic functions of Nm, have the advantage of intervening in a significant manner in the virulence of Nm, being involved in the stage of initial colonization and penetration and in the septicaemic dissemination.

According to other embodiments, the invention provides transfer and expression vectors, such as plasmids, cosmids or bacteriophages, comprising at least one DNA as defined above.

It also provides host cells transformed by at least one DNA as defined above.

Other host cells of the invention comprise genes or gene fragments specific to Nm, and are characterized in that their chromosome is deleted by at least one DNA according to the invention, in particular a DNA responsible for the pathogenicity. They are more specifically bacterial cells, in particular of Nm.

The invention also relates to the RNAs of which the sequence corresponds in all or part to the transcription of at least one DNA sequence or sequence fragment as defined above.

The invention also relates to the antisense nucleic acids of the DNAs as defined above, or of fragments of these DNAs.

These antisense nucleic acids carry, where appropriate, at least one substituent, such as a methyl group and/or a glycosyl group.

Other products which fall within the context of the invention include polypeptides.

These polypeptides are characterized in that they have an amino acid chain corresponding to all or part of a sequence coded by the nucleic acids defined above, or deduced from sequences of these nucleic acids.

They are advantageously polypeptides corresponding to all or part of the polypeptides exported beyond the cytoplasmic membrane, more specifically polypeptides corresponding to all or part of those coded by a conserved region.

As a variant, the polypeptides of the invention can be modified with respect to those corresponding to the nucleic acid sequences such that they are particularly suitable for a given use, in particular use as a vaccine.

Modification is understood as meaning any alteration, deletion or chemical substitution where this does not affect the biochemical properties of the corresponding natural polypeptides, more specifically of functional proteins exported at the periplasm and the external membrane.

Other products according to the invention include antibodies directed against the above polypeptides.

The invention thus provides polyclonal antibodies, and also monoclonal antibodies, characterized in that they recognize at least one epitope of a polypeptide as described above.

It also relates to fragments of these antibodies, more particularly the fragments Fv, Fab and Fab'2.

The invention also relates to the anti-antibodies which are capable of recognizing the antibodies defined above, or their fragments, by a reaction of the antigen-antibody type.

According to the invention, the various products considered above are obtained by a synthesis and/or biological route in accordance with conventional techniques.

The nucleic acids can also be obtained from banks made up of Nm-specific DNAs such as are formulated by a subtractive technique, this technique comprising:

- mixing of two DNA populations,
- realization of at least one subtractive hybridization-amplification iteration, and
- collection of the desired DNA or DNAs, followed, where appropriate, by its/their purification with elimination of redundant sequences.

According to the invention, the two DNA populations originate respectively from a strain of *Neisseria meningitidis*, the so-called reference strain for which the specific bank must be constructed, and a strain of *Neisseria*, the so-called subtraction strain, having a homology in primary DNA sequences of greater than about 70% with the *Neisseria meningitidis* strain, the DNA sequences of the subtraction and reference strains being obtained respectively by random shearing, and by cleavage by a restriction endonuclease capable of producing fragments less than about 1 kb in size.

The invention provides in particular a process for obtaining *Neisseria meningitidis*-specific DNA banks, comprising the stages of

- random shearing of the chromosomal DNA of a strain of *Neisseria gonorrhoeae*, the so-called subtraction strain, in particular by repeated passage through a syringe,
- cleavage of the chromosomal DNA of a strain of *Neisseria meningitidis*, the so-called reference strain, preferably by a restriction enzyme producing fragments less than about 1 kb in size,
- splicing of the DNA fragments of the reference strain, cleaved by the restriction enzyme, with suitable oligonucleotide primers,
- realization of a subtractive hybridization-amplification iteration, by:
  - mixing of the two DNA populations under suitable conditions for hybridization of homologous sequences, and then
  - amplification of auto-reannealed fragments and collection of these fragments,
  - digestion of these fragments by a restriction enzyme and re-splicing with oligonucleotide primers, followed by a
- purification of the spliced DNA and, where appropriate, a new iteration of the subtractive hybridization, comprising mixing of DNA fragments of *Neisseria gonorrhoeae* sheared as indicated above with DNA fragments of *Neisseria meningitidis* produced by the preceding iteration, followed, if desired, by cloning of the DNAs of the bank.

The primers used are oligodeoxynucleotide primers which are suitable for the restriction endonuclease used and allow insertion into a cloning site, such as the EcoRI site of the plasmid pBluescript. Such primers will advantageously be chosen among the oligodeoxynucleotides referred to in the sequence listing under SEQ ID no. 36 to 45.

The banks thus obtained are formed from DNAs which are specific to meningococci and absent from gonococci.

The specificity of the DNAs was verified, as described in the examples, at each iteration by Southern blots, with genes common to the subtraction strain and to the reference strain, or with the total DNA of each of the strains digested by a restriction endonuclease, such as ClaI.

At each iteration, the exhaustivity of the DNA bank was also verified by Southern blotting with probes known to be specific to the reference strain, that is to say for *Neisseria meningitidis* the frp, opc and rotamase genes in particular.

The experiments carried out showed that the banks obtained by the process of the invention are deficient in genes having a significant homology with species of *Neisseria* other than *Neisseria meningitidis*, for example the ppk or pilC1 genes, generally in only 2 or 3 iterations.

If necessary, two routes, which are not exclusive of each other, can be taken.

It is possible to proceed with an $(n+1)^{th}$ iteration using the DNA of iteration n as the DNA population of the reference strain.

As a variant, a second bank independent of the first is constructed, with a restriction enzyme of different specificity to that used in the first bank, for example MboI.

In all cases, it is preferable to keep each of the products produced by each of the iterations performed.

The invention also provides the use of the subtractive technique described above to obtain banks of the DNAs common to Nm and Ng, but specific with respect to Nl.

Three different banks are advantageously constructed, two of them by digestion of the chromosomal DNA of Nm by MboI and Tsp5091, and the third by digestion of the chromosomal DNA of Nm with MspI. Two subtraction series allow the DNAs having the required specificity to be collected, as described in the examples.

The invention also relates to the process for obtaining these banks and the banks themselves.

It can be seen that, generally, the process of the invention can be used to obtain banks of DNAs specific to a given cell species, or to a given variant of the same species, where another species or another variant which is close genomically and expresses different pathogenic potencies exists.

Using the process of the invention, DNA banks specific to given species of *cryptococci, Haemophilus, pneumococci* or also *Escherichia coli*, or more generally any bacterial agent belonging to the same species and having different pathovars will advantageously be constructed.

Furthermore, from these banks the invention provides the means to have available virulence factors specific to a species or a given variant.

Such banks are therefore tools which are of great interest for having available attributes which are responsible for the specificity of a pathogen, this use being more specifically illustrated according to the invention by the obtaining of banks comprising the attributes responsible for the specificity of the meningococcal pathogenesis.

Study of the products of the invention, the nucleic acids, polypeptides and antibodies, has enabled an absolute specificity with respect ot *Neisseria meningitidis*, regardless of the strain and its variability, to be demonstrated.

These products are therefore particularly suitable for diagnosis or prevention of infections and meningitis caused by *Neisseria meningitidis*, whether in adults or children and regardless of the serogroups of the strain in question.

The method for diagnosis, according to the invention, of a meningococcal infection, and more particularly of meningococcal meningitis, by demonstration of the presence of *Neisseria meningitis* in an analytical sample is characterized by the stages of:

- bringing into contact a sample to be analysed, that is to say a biological sample or a cell culture, and a reagent formulated from at least one nucleic acid as defined above, if appropriate in the form of a nucleotide probe or a primer, or, as a variant, from at least one antibody or a fragment of an antibody as defined above, under conditions which allow, respectively, hybridization or a reaction of the antigen-antibody type, and
- detection of any reaction product formed.

If the reagent is formulated from a nucleic acid, this can be in the form of a nucleotide probe in which the nucleic acid or a fragment of the latter is labelled in order to enable it to be detected. Suitable markers include radioactive, fluorescent, enzymatic or luminescent markers.

As a variant, the nucleic acid is included in a host cell, which is used as the reagent.

In these various forms, the nucleic acid is used as such or in the form of a composition with inert vehicles.

If the reagent is compiled from an antibody, or a fragment of an antibody, this can be labelled for detection purposes. Most generally, a fluorescent, enzymatic, radioactive or luminescent marker is used.

The antibody or the antibody fragment used, which is labelled if appropriate, can be used as such or in the form of a composition with inert vehicles.

The sample used in the stage of bringing the components into contact is a biological sample produced by a mammal, such as cephalorachidian fluid, urine, blood or saliva.

The detection stage is carried out under conditions which allow the reaction product to be demonstrated when it is formed. Conventional means use fluorescence, luminescence, colour or radioactive reactions, or also autoriadography [sic] techniques. It is also possible to quantify the product.

The invention also relates to the labelled products, the nucleic acids and antibodies, as new products.

The method defined above can be used for diagnosis of an immune reaction specific to a meningococcal infection.

The reagent used is thus a polypeptide according to the invention, as coded by the said nucleic acid sequences, corresponding to the natural product or a polypeptide which is modified but has the biological and immunological activity of the corresponding natural polypeptide.

It is advantageously a polypeptide exported beyond the cytoplasmic membrane of *Neisseria meningitidis*, more particularly the part of such a polypeptide corresponding to the conserved region of the DNA.

The invention also relates to kits for carrying out the methods defined above. These kits are characterized in that they comprise:

- at least one reagent as defined above, that is to say of the nucleic acid, antibody or polypeptide type,
- products, in particular markers or buffers, which enable the intended nucleotide hybridization reaction or immunological reaction to be carried out, as well as use instructions.

The specificity of the products of the invention and their location on the chromosome of *Neisseria meningitidis* Z2491, either grouped in a region and able to be interpreted as pathogenicity islets, or isolated on the chromosome, impart to them a very particular interest for realization of vaccine compositions with a universal purpose, that is to say whatever the strain and the variability which it expresses. These compositions can include in their spectrum other prophylaxes, and can be, for example, combined with childhood vaccines.

The invention thus provides vaccine compositions which include in their spectrum antimeningococcal prophylaxis, intended for prevention of any infection which may be caused by *Neisseria meningitidis*, these compositions being characterized in that they comprise, in combination with (a) physiologically acceptable vehicle(s), an effective amount of polypeptides or anti-antibodies or their fragments as defined above, these products optionally being conjugated, in order to reinforce their immogenicity [sic].

Immunogenic molecules which can be used comprise the poliovirus protein, the tetanus toxin, or also the protein produced by the hypervariable region of a pilin.

As a variant, the vaccine compositions according to the invention are characterized in that they comprise, in combination with (a) physiologically acceptable vehicle(s), an effective amount:

of nucleic acids as defined above, of transformed host cells as defined above, or of Nm cells, the chromosome of which has been deleted by at least one DNA sequence according to the invention involved in the pathogenicity of the bacterium. The nucleotide material used is advantageously placed under the control of a promoter of its expression in vivo and synthesis of the corresponding protein. To reinforce the immunogenicity, it is also possible to combine this nucleic material with a DNA or an RNA which codes for a carrier molecule, such as the poliovirus protein, tetanus toxin or a protein produced by the hypervariable region of a pilin.

The vaccine compositions of the inventions can be administered parenterally, subcutaneously, intramuscularly or also in the form of a spray.

Other characteristics and advantages of the invention are given in the examples which follow for illustration thereof, but without limiting its scope.

BRIEF DESCRIPTION OF THE SEVERAL VIEWS OF THE DRAWING(S)

In these examples, reference will be made to FIGS. 1 to 11, which show, respectively, FIGS. 1A, 1B, 1C, 1D, 1E, 1F and 1G: analysis of the subtractive bank Tsp5091, FIG. 2: the distribution of the Nm-specific sequences, in contrast to Ng, on the chromosome of the strain Z2491 (left-hand part) and of Nm-specific sequences, in contrast to Nl (right-hand part), FIGS. 3A to 3C: the reactivity of the clones of the 3 regions of the chromosome according to the invention towards a panel of strains of the genus *Neisseria,*

FIG. 4: the position in region 2 of the chromosome of Nm of oligonucleotides used as probes, FIGS. 5, 6 and 7: the Southern blots of a panel of strains of the genus *Neisseria*, using parts of region 2 of Nm as probes, FIGS. 8A to 8C: the Southern blots with 3 subtractive banks over a panel of 12 strains of *Neisseria*, and FIGS. 9, 10 and 11: the reactivity of clones of the 3 subtractive banks with respect to Nm, Nl and Ng.

In the examples which follow, the following materials and methods were used:

Bacterial strains—To obtain the subtractive banks, strain Z2491 of Nm (Achtman et al., 1991*, J. Infect. Dis.* 164, 375–382), the strains MS11 (Swanson et al., 1974*, Infect. Immun.* 10, 633–644) and the strains 8064 and 9764 of Nl were used, it being understood that any other strain of the species in question could be used.

In order to verify the specificity of these banks, 6 strains of Nm, 4 strains of Ng, one strain of Nl (*Neisseria lactamica*) and one strain of Nc (*Neisseria cinerea*) were used.

The six strains of Nm are: Nm Z2491 of serogroup A, Nm 8013 of serogroup C (XN collection), Nm 1121, no serogrouping possible (XN collection), Nm 1912 serogroup A (XN collection), Nm 7972 of serogroup A (XN collection) and Nm 8216 of serogroup B (XN collection).

The four strains of Ng are: Ng MS11 (Pasteur Institute, Paris), Ng 403 (Pasteur Institute, Paris), Ng 6934 (Pasteur Institute, Paris), Ng WI (isolated from a disseminated gonococcal infection), Ng 4Cl, Ng 6493 and Ng FA 1090.

The strains of Nl are Nl 8064 and Nl 9764 (XN collection), and that of Nc is Nc 32165 (XN collection).

Molecular Genetics Techniques

Unless indicated otherwise, the techniques and reagents used correspond to those recommended by Sambrook et al (Sambrook et al 1989, Molecular Cloning: A Laboratory Manual. Cold Spring Harbor Laboratory Press). The oligodeoxynucleotides used in this study are:

```
                                        (SEQ ID No.54)
RBAm12,    3' AGTGGCTCCTAG 54
                                        (SEQ IN No.55)
RBam24,    5' AGCACTCTCCAGCCTCTCACCGAG 3';
                                        (SEQ ID No.60)
Jbam12,    3' GATCCGTTCATG 5';
                                        (SEQ ID No.61)
JBAM24,    5' ACCGACGTCGACTATCCATGAACG 3';
                                        (SEQ ID No.56)
REco12,    AGTGGCTCTTAA;
                                (= RBam 24,SEQ ID NO.55)
REco24,    5' AGCACTCTCCAGCCTCTCACCGAG 3';
                                        (SEQ ID No.62)
JEco12,    GTACTTGCTTAA;
                                            (= JBam 24)
JEco24,    5' ACCGACGTCGACTATCCATGAACG 3';
                                        (SEQ ID No.64)
NEco12,    AATTCTCCCTCG;
                                       (SEQ ID No.65).
NEco24,    AGGCAACTGTGCTATCCGAGGGAG;
```

Transfer to Membranes (Southern Blots)

The transfers to membranes were effected by capillary transfers to positively charged nylon membranes (Boehringer Mannheim). The hybridizations were carried out at 65° C. in a solution comprising NaPi [sic] 0.5 M pH 7.2/EDTA 1 mM/SDS 7%/BSA 1%. The membranes were washed in a solution comprising NaPi [sic] 40 mM pH 7.2/EDTA 1 mM/SDS 1%. The final washing was carried out at 65° C. for 5 min.

The probe frp obtained with oligonucleotides based on the frpA sequence corresponds to 2.4 kb of the 5' end of the gene of the strain Z2491. The opc and rotamase probes corresponding to whole genes are produced from the strain Z2491 using oligonucleotides constructed on the basis of published sequences. The probes pilCl and ppk (polyphosphate kinase) correspond to inserts of the plasmids pJL1 and pBluePPK6001 respectively.

EXAMPLE 1

Construction of Banks of DNAs Present in Nm and Absent from Ng a. "MboI" Bank Construction—The DNA of Nm Z2491 was cleaved by the endonuclease MboI and subjected to two iterations of a method called CDA (comprehensive difference analysis) below. This method comprises subtractive hybridization in the presence of excess sheared DNA of Ng MS11 and amplification by PCR of those meningococcal sequences which, since they are absent from or do not have significant homology with the DNA of Ng MS11, could reanneal.

The chromosomal DNA of the strain Ng MS11 is sheared randomly by repeated passage through a hypodermic syringe until fragments of a size ranging from 3 to 10 kb are obtained. These DNA fragments are purified by extraction with phenol.

The chromosomal DNA of the strain Nm Z2491 is itself cleaved by the restriction endonuclease MboI. These DNA fragments (20 µg) are spliced with 10 nmol of annealed oligonucleotides RBam12 and RBam24. The excess primers are removed by electrophoresis over 2% agarose gel of low melting point. The part of the gel containing amplified fragments greater than 200 bp in size is excised and digested by β-agarase. These fragments are purified by extraction with phenol.

To carry out a subtractive hybridization (first iteration), 0.2 µg of the Nm DNA spliced with the RBam oligonucleotides is mixed with 40 µg Ng DNA in a total volume of 8 ml of a buffer EE 3× (a buffer EE 1× is composed of N-(2-hydroxyethyl)piperazine-N'-(3-propanesulphonic acid) 10 mM and EDTA 1 mM, and its pH is 8.0). This solution is covered with mineral oil and the DNA is denatured by heating at 100° C. for 2 min. 2 µl NaCl 5 M are added and the mixture is left to hybridize at 55° C. for 48 h. The reaction mixture is diluted to 1/10 in a preheated solution composed of NaCl and buffer EE, and in then immediately placed on ice.

10 µl of this dilution are added to 400 µl of PCR reaction mixture (Tris.HCl pH 9.0 10 mM; KCl 50 mM; $MgCl_2$ 1.5 mM; Triton X100 0.1%; 0.25 mM of each of the four triphosphate deoxynucleotides; Taq polymerase 50 units per ml). The mixture is incubated for 3 min at 70° C. to complete the ends of the reannealed meningococcal DNA fragments.

After denaturing at 94° C. for 5 min and addition of the oligonucleotide RBam24 in an amount of 0.1 nmol per 100 µl, the hybridizations are amplified by PCR (30 cycles of 1 min at 94° C., 1 min at 70° C. and 3 min at 72° C., followed by 1 min at 94° C. and 10 min at 72° C.; Perkin-Elmer GeneAmp 9600).

The amplified meningococcal fragments are separated from the primers and high molecular weight gonococcal DNAs on gel. They are digested by MboI and the oligonucleotides JBam12 and JBam 24 are spliced to them again. These spliced DNAs are again purified over gel and extracted with phenol.

A second iteration of the subtractive hybridization is carried out on 40 µg of the randomly sheared Ng DNA and 25 ng of the DNA spliced with the JBam oligonucleotides obtained from the first iteration of the subtractive hybridization. During this second iteration, amplification of the auto-annealed Nm DNA is effected with the aid of the oligonucleotide JBam24.

Specificity—In order to confirm their Nm specificity, the amplified sequences after the second iteration of the CDA method are labelled and used as a probe for the DNA digested by ClaI produced from a panel of six strains of *Neisseria meningitidis*, four of *Neisseria gonorrhoeae*, one of *Neisseria lactamica* and one of *Neisseria cinerea*.

The Southern blots obtained show that the amplified sequences resulting from the second iteration of the CDA method have a high reactivity with several bands corresponding to meningococci, and do not have a reactivity with the bands corresponding to the Ng, Nl and Nc strains.

The "MboI" bank thus appears to be Nm-specific.

Exhaustivity—In order to test the exhaustivity of the bank, all the products produced from the first and second iterations of the CDA method and also the initial chromosomal materials of Nm Z2481 [sic] and Ng MS11 are subjected to agarose gel electrophoresis, transferred to a membrane and brought into contact with probes comprising genes known to be meningococcus-specific, that is to say frp, opc and rotamase (Southern blotting).

As a result of these hybridizations, the Nm-specific gene frp is represented in the MboI bank by a fragment of 600 bp, but no activity is observed for the rotamase and opc genes. The MboI bank, although Nm-specific, therefore cannot be considered exhaustive.

Given their high specificity, the fragments produced by the second iteration of the CDA method for the MboI bank can nevertheless be cloned on the BamHI site of the plasmid pBluescript.

A sequence corresponding to any of the Nm-specific genes can be included in the subtractive bank only if it is carried by a restriction fragment of appropriate size. This condition is a function of two factors. Firstly, the probability that the largest fragments are entirely Nm-specific is low. Secondly, even if such fragments existed, they would be under-represented in the bank because of the limitations of the PCR technique, the amplification effectiveness of which decreases with increasing size of the fragments. Fragments greater that about 600 bp in size are not included in the bank. Because of the absence of Mbo fragments of suitable size from the chromosome of Nm Z2491, the rotamase and opc genes cannot be included in the bank. Any enzyme cannot by itself produce a small fragment corresponding to any Nm-specific gene. A second bank was therefore constructed using another restriction enzyme with a different specificity: Tsp509 [sic].

b. "Tsp509I" Bank

Construction—The enzyme Tsp5091 has the advantage of producing fragments of smaller size (less than about 1 kb) than the enzyme MboI.

Tsp509I recognizes the sequence AATT and leaves, projecting at 5', a sequence of 4 bases compatible with EcoRI. The oligonucleotides used are Reco, Jeco and NEco.

The method followed conforms with that followed for construction of the "MboI" bank described above. However, higher quantities of meningococcal DNA were used for the first iteration of the subtractive hybridization in order to compensate for the higher number of fragments of low molecular weight produced by Tsp509I. For the first iteration, 400 ng Nm DNA fragments and, in the second, 25 ng Nm fragments are subjected to subtractive hybridization with 40 µg randomly sheared Ng DNA.

For the construction of this "Tsp509I" bank, as a control, a third iteration of the subtractive hybridization is carried out using 40 µg sheared Ng DNA and 0.2 ng Nm fragments resulting from a digestion by Tsp509I and a resplicing, with NEco adaptors, of the fragments obtained as a result of the second iteration.

Specificity—As described for the previous bank, the product resulting from the second iteration of the CDA method is labelled and used as the probe for a panel of strains of Neisseria.

FIG. 1A illustrates the Southern blot hybridization of products of the second iteration of the CDA method with the DNA digested by ClaI of: Nm in track a, Ng MS11 in track b, Nm 8013 in track c, Ng 403 in track d, Nm 1121 in track e, Ng 6934 in track f, Nm 1912 in track g, Ng WI (strain DGI) in track h, Nm 7972 in track i, Nl 8064 in track j, Nc 32165 in track k, Nm 8216 in track l.

In contrast to the high reactivity observed with all the Nm strains, a low or no reactivity is observed with the Ng, Nl and Nc strains.

The specificity of the bank was studied earlier by reacting membrane transfers (Southern blots) of the products produced by each of the three iterations of the CDA method with probes corresponding to pilC1 and ppk. These two genes are common to Nm and Ng.

FIG. 1B shows an agarose gel after electrophoresis of the chromosomes of Nm Z2491 and Ng Ms11, digested by Tsp509 [sic], and products resulting from each of the iterations of the CDA method.

In track a 1 µg of the chromosome of Nm was deposited, in track b 1 µg of that of Ng, in track c 0.15 µg of the products resulting from the first CDA iteration, in track d 0.1 µg of those of the second iteration, in track e 0.05 µg of the third iteration, MW representing the molecular size markers.

FIGS. 1C and 1D show gels obtained as described in FIG. 1B after transfer to the membrane (Southern blots) and hybridization with pilC1 (FIG. 1C) and ppk (FIG. 1D).

At the end of the second iteration of the CDA method, the sequences corresponding to the pilC1 and ppk genes are completely excluded from the bank.

Exhaustivity—The exhaustivity of the bank was examined by reacting the products resulting from the subtractive hybridization with the probes corresponding to three Nm-specific genes (frp, rotamase and opc).

These Nm-specific probes react with the amplification products resulting from the first and second iteration of the subtractive hybridization.

FIGS. 1E, 1F and 1G show gels obtained as described in FIG. 1B after transfer to the membrane (Southern blots) and hybridization with frpA (FIG. 1E), rotamase (FIG. 1F) and opc (FIG. 1G).

However, a third iteration of the subtractive hybridization leads to the loss of Nm-specific sequences, since the fragments which react with the rotamase and opc genes are absent from this third iteration.

In consideration of all these data, it emerges that the products resulting from the second iteration of the CDA method are Nm-specific and also constitute an exhaustive bank of Nm-specific sequences.

The products resulting from this second iteration are cloned at the EcoRI site of the plasmid pBluescript.

The bank produced by Tsp509I is more exhautive [sic] than the bank produced by MboI, as the theory considerations based on the enzymatic production of smaller restriction fragments would suggest.

In accordance with this aspect, it should be noted that the Tsp509I bank is less redundant than the MboI bank, that is to say it comprises less duplication of clones. 86% of the clones of the Tsp509I bank correspond to distinct sequences, while only 43% of the clones correspond to distinct sequences in the MboI bank (data not shown).

The bank produced by Tsp509I thus constitutes a source of Nm-specific clones.

EXAMPLE 2

Analysis of the Clones of the Subtractive Bank

Cloning and Sequencing of the Nm-Specific DNAs

The DNAs of the subtractive banks are clones at the BamHI (MboI bank) or EcoRI (Tsp509I bank) site of the plasmid pBluescript, and then transformed in DH5α of E. coli. The inserts are amplified by PCR carried out on the transformed colonies using the primers M13-50 and M13-40, the latter primer being biotinylated on its 5' end.

Sequencing was carried out on each PCR product after separation of the biotinylated and non-biotinylated strands using the system of Dynabeads M-280 with streptavidin (Dynal, Oslo). The sequences are screened according to their homologies with previously published sequences using the computer programs Blastn and Blastx (NCBI, USA and Fasta).

The PCR products resulting from the transformed bacteria colonies after using the primers M13-40 and M13-50 as described above were labelled by incorporation with random priming of $\alpha$-$^{32}$P-dCTP and were used as a probe for the membrane transfers of the chromosomal DNA digested by ClaI of strains Nm Z2491 and Ng MS11, as described above, in order to verify their specificity.

Mapping of Clones on the Chromosome of the Strain Nm Z2491.

The results of studies carried out with 17 clones of the "MboI" bank (designated by the letter B) and 16 clones of the "Tsp5091" bank (designated by the letter E), each of these clones having a unique sequence and being without counterpart in Ng, are reported.

The positions of the DNA sequences corresponding to cloned Nm-specific products were determined with respect to the published map of the chromosome of Nm Z2491 (Dempsey et al. 1995, J. Bacteriol. 177, 6390–6400) and with the aid of transfers to membranes (Southern blots) of agarose gel subjected to pulsed field electrophoresis (PFGE).

The Nm-specific clones are used as probes for a hybridization on membranes (Southern blots) of the DNA of Nm Z2491 digested with enzymes of rare cutting sites, that is to say PacI, PmeI, SgfI, BglII, SpeI NheI and SgfI.

The gels (20×20 cm) were gels of 1% agarose in a buffer TBE 0.5× and were subjected to electrophoresis at 6 V/cm for 36 hours according to pulsation periods varying linearly between 5 and 35 seconds.

The hybridizations on the membrane (Southern blots) were carried out as described above.

The results obtained are shown on FIG. 2: the reactivity was located by comparison with the positions of the fragments of corresponding size on the published map. The positions of all the genetic markers mapped by Dempsey et al (mentioned above) are visualized with the aid of points on the to linear chromosomal map. The Nm-specific genes disclosed previously are labelled with an asterisk. The two loci called "frp" correspond to the frpA and frpc genes. The "pilC" loci correspond to the pilC1 and pilC2 genes, which are pairs of homologous genes and are not distinguished on the map. The accuracy of the positions of the Nm-specific clones of the invention depends on the overlapping of reactive restriction fragments. On average, the position is +/−20 kb.

This mapping reveals a non-random distribution of the Nm-specific sequences. The majority of the Nm-specific sequences belong to three distinct groups. One of these groups (region 1) corresponds to the position of genes relating to the capsule which have been described previously.

A distinction is made between:

E109, E138, B230 and B323 as being region 1,

B322, B220, B108, B132, B233, B328, E139, E145 as B101 as being region 2, and

B306, E114, E115, E124, E146, E120, E107, E137 and 142 as being region 3.

63% of the sequences identified as specific to meningococci are located inside these three distinct regions.

This grouping contrasts with the distribution of previously disclosed Nm-specific genes (frpA, frpC, porA, opc and the region relating to the capsule).

This prior art would suggest in fact that the Nm-specific genes, with the exception of functional genes relating to the capsule, were dispersed along the chromosome.

Mapping of Nm-specific sequences on the chromosome leads to an unexpected result with regard to the prior art.

The majority of the genetic differences between the meningococcal and gonococcal strains tested are grouped in three distinct regions.

Meningococcal genes relating to the capsule are grouped in region 1.

The function of genes of the other regions is unknown, but homologies with published sequences (table 1) suggest similarities between certain genes of region 3 and bacteriophage transposase and regulatory proteins. No meningococcal virus has been characterized and it is tempting to think that these sequences are of phagic origin. Interestingly, the genome of *H. influenzae* also contains a sequence homologous to that of the Ner regulatory protein of phage Mu, but it is not known if it is a functional gene.

The clone B208 has a high homology (48% identical, 91% homology for 33 amino acids) with a clone of conserved regions field III) in the class of proteins which bind to TonB-dependent ferric siderophors.

The proximity of this clone with the Nm-specific porA genes and the frp genes regulated by iron, and in particular the possibility that it is an Nm-specific receptor protein exposed on the external membrane in itself is a good candidate for further research.

The clone B339 corresponds to the Nm-specific insertion sequence IS1106.

The low homology between the clone B134 and the Aeromonas insertion sequence and also the presence of multiple copies of the clone B134 among the various strains of Nm suggest that it could be a new type of Nm-specific insertion sequence.

The possibility that the regions containing the Nm-specific clones could correspond to pathogenicity islets as described previously for *E. coli* and *Y. pestis* is of particular interest.

The clones isolated in this invention will allow better understanding of the relevance of Nm-specific regions in allowing cloning and sequencing of larger chromosomal fragments, and directly by their use for loci mutations.

Finally, detection of meningococcus-specific genes possibly involved in the pathogenicity of the organism allows targeting of suitable antigens which can be used in an antimeningococcal vaccine.

The effectiveness and the speed of the method according to the inventions enables it to be used in a large number of situations for which the genetic differences responsible for a phenotype peculiar to one of 2 close pathogens are investigated.

Study of the Reactivity of the Clones of Regions 1, 2 and 3 Towards a Panel of Strains of *Neisseria*.

The PCR products corresponding to inserts of each of the clones were collected and used as probes for hybridization on membranes (Southern blots) for a panel of strains of Nm, Ng, Nl and Nc.

Regions 1 and 2 produce a limited number of bands for each of the meningococci. This suggests that these regions are both Nm-specific and common to all the meningococci.

Figure 3:
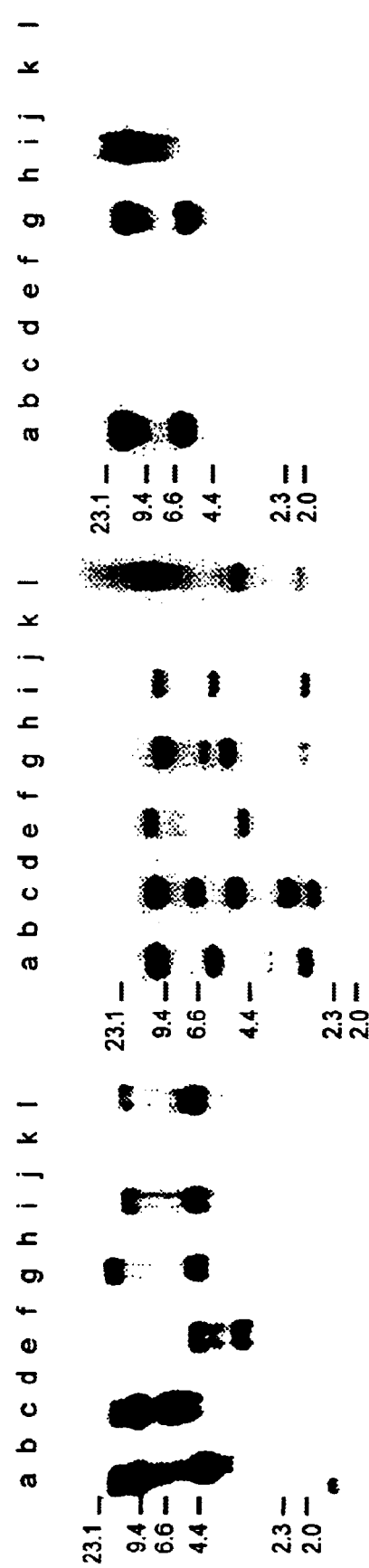

FIG. 3 illustrates the reactivity of the clones of regions 1, 2 and 3 towards a panel of neisserial strains. The clones of regions 1 (FIG. 3A), 2 (FIG. 3B) and 3 (FIG. 3C) taken together were used as probes towards a panel of meningococci, gonococci and towards a strain of Nl and Nc.

The tracks are as follows: DNA of: Nm Z2491 in track a, of Ng MS11 in track b, of Nm 8013 in track c, of Ng 403 in track d, of Nm 1121 in track e, of Ng 6934 in track f, of Nm 1912 in track g, of Ng WI (strain DGI) in track h, of Nm 7972 in track i, of Nl 8064 in track j, of Nc 32165 in track k, and of Nm 8216 in track l.

Remarkably, region 3 has reactivity only with the meningococci of serogroup A. This region 3 is therefore specific to a sub-group of Nm.

A comparison was made with the known sequences in the databanks in order to evaluate the possible functions of the cloned regions.

Table 1 which follows gives the positions of specific clones on the chromosomal map and the homologies with known sequences.

TABLE 1

Position of specific clones on the chromosomal map and homologies with known sequences

| Name of clone* | Size of insert | Reactive fragments | | | | | | Position on Z2491 | Homologies of protein sequences |
|---|---|---|---|---|---|---|---|---|---|
| | | Pac | Pmc | Bgl | Spe | Nhe | Sgf | | |
| B305 | 259 | 18–20 | 15–17 | 22–23 | 18 | 11–13 | 2 | λ736 | |
| B333 | 235 | | 15–17 | 22–23 | 18 | 11–13 | 2 | λ736 | |
| E109[1+] | 211 | | 6–7 | 11–15 | 10 | 11–13 | 2 | tufA ctrA | protein LipB *N. meningitidis* (3 × 10$^{-26}$) |

TABLE 1-continued

Position of specific clones on the chromosomal map and homologies with known sequences

| Name of clone* | Size of insert | Reactive fragments | | | | | Position on Z2491 | Homologies of protein sequences |
|---|---|---|---|---|---|---|---|---|
| | | Pac | Pmc | Bgl | Spe | Nhe | Sgf | | |
| E138[1+] | 315 | 1 | 6–7 | 11–15 | 10 | 11–13 | 2 | tufA ctrA | protein LipB *N. meningitidis* ($4 \times 10^{-75}$) |
| B230[1] | 356 | 1–3 | 6–7 | 1 | 10 | 11–13 | 2 | ctrA | protein KpsC *E. coli* ($3 \times 10^{-53}$) |
| B323[1] | 363 | 1 | 6–7 | 1 | 10 | 11–13 | 2 | ctrA | protein CtrB *N. meningitidis* ($2 \times 10^{64}$) |
| B322[2] | 210 | | 2 | 16–18 | 6 | 1 | 5 | pilQ/λ 740 | HlyB *S. marcescens* ($4 \times 10^{-15}$) |
| B220[2] | 341 | | 2 | 16–18 | 6 | ≧18 | 5 | pilQ/λ 740 | |
| B108[2] | 275 | | 2 | 19–21 | 6 | ≧18 | 5 | pilQ/λ 740 | |
| B132[2] | 411 | 2 | 2 | 19–21 | 6 | ≧18 | 5 | pilQ/λ 740 | |
| B233[2] | 164 | 1–3 | 2 | 19–21 | 6 | ≧18 | 5 | pilQ/λ 740 | |
| B328[2] | 256 | 1–3 | 2 | 22–23 | 6 | ≧18 | 5 | pilQ/λ 740 | |
| E139[2] | 324 | 2 | 2 | 19–21 | 6 | ≧18 | 5 | pilQ/λ 740 | |
| E145[2] | 343 | 2 | 2 | 19–21 | 6 | ≧18 | 5 | pilQ/λ 740 | |
| B101[2] | 254 | ≧20 | 2 | 19–21 | 6 | ≧18 | 5 | pilQ/λ 740 | |
| E103q | 334 | | 2 | 11–15 | 3–5 | 10 | 3 | λ644 | |
| B326[§] | 314 | | 2 | 11–15 | 3–4 | 10 | 3 | λ644 | |
| B326 (low reactivity) | | | 5 | 6 | 16 | 2 | 1 | argF | |
| B342 | 167 | | 2 | 19 | 3–4 | 6–7 | 3 | iga | |
| E136 | 249 | | 2 | 7 | 1 | 3 | 3 | lepA | |
| B208 | 177 | | 1 | 2 | 3–4 | 2 | 1 | porA | FeIII pyochelin receptor *P. aeruginosa* ($5.10^{-4}$) |
| = B306[3#] | 219 | 11 | 5 | 11–12 | 5 | 2 | 4 | parC | |
| E114[3] | 227 | 11 | 5 | 11–12 | 5 | 2 | 4 | parC | |
| E115[3#] | 251 | | 5 | 11–15 | 5 | 2 | 4 | parC | |
| E124[3] | 208 | | 5 | 11–12 | 5 | 2 | 4 | parC | |
| E146[3] | 146 | | 5 | 11–15 | 5 | | 4 | parC | |
| E120[3] | 263 | | 5 | 3–4 | 5 | 16 | 4 | opaB | |
| E107[3] | 248 | 11 | 14–17 | 3–4 | 5 | 16 | 4 | opaB | |
| E137[3] | 274 | | 14–17 | 3–4 | 5 | 16 | 4 | opaB | Transposase Bacteriophage D3112 ($6 \times 10^{-12}$) |
| E142[3] | 230 | | 14–17 | 3–4 | 5 | 16 | 4 | opaB | Protein Ner-Like *H. influenzae* ($6 \times 10^{-23}$) Protein binding to the DNA Ner, phage mu ($3 \times 10^{-18}$) |
| E116 | 379 | 5–7 | 11–13 | 3–4 | 2 | 6–7 | 8 | λ375 | |
| B313 | 436 | 9 | 9 | 3–4 | 13–14 | 5 | 2 | λ611 | |
| B341 | 201 | 8–10 | 9 | 3–4 | 13–14 | 5 | 2 | λ611 | |
| E102 | 238 | | 11–13 | 3–4 | 19 | 5 | 2 | λ601 | Hypothetical protein H11730 *H. influenzae* ($7 \times 10^{-24}$) |
| B134 | 428 | | | multiple | | | | | transposase ISAS2 *Aeromonas salmonicida* ($5 \times 10^{-5}$) |
| B339 | 259 | | | multiple | | | | | transposase IS 1106 *N. meningitidis* ($6 \times 10^{-45}$) |

The level of homologies found, as given by the Blastx program, are indicated in parentheses
*The clones labelled with the index "1", "2" or "3" belong to regions "1", "2" or "3" respectively of the chromosome of *N. meningitidis* Z2491.
[1+]E109 and E138 are contiguous clones [§]B306 and E115 overlap [#]B236 also has a low reactivity in the region of arg F
q) Clone E103 contains a Tsp509 I site and can therefore contain two inserts; however, since it reacts only with a single fragment ClaI (Oks) of the chromosome of *N. meningitidis* Z2491 and occupies only one position on the map, this clone is included here.

Firstly, it can be seen that the clones of region 1 all correspond to genes involved in biosynthesis of the capsule. These genes have previously been studied among the Nm of serogroup B (Frosch et al. 1989, Proc. Natl. Acad. Sci. USA 86, 1669–1673 and Frosch and Muller 1993, Mol. Microbiol. 8 483–493).

With the exception of a low homology with the haemolysin activator of Serratia marcescens, the clones of region 2 have no significant homology with published sequences, either in the DNA or the proteins.

Two of the clones of region 3 have interesting homologies with proteins which bind to the DNA, in particular the bacteriophage regulatory proteins and transposase proteins.

Clone B208 has a high homology with one of the conserved regions in one class of receptors (TonB-dependent ferric siderophor).

Clones B134 and B339 hybridize with several regions of the chromosome (at least 5 and at least 8 respectively).

Data relating to the sequences show that clone B339 corresponds to the Nm-specific insertion sequence S1106.

The translation of the clone B143 has a limited homology with the transposase of an Aeromonas insertion sequence (SAS2) (Gustafson et al. 1994, J. Mol. Biol. 237, 452–463). We were able to demonstrate by transfer on a membrane (Southern blots) that this clone is an Nm-specific entity present in multiple copies in the chromosomes of every meningococcus of the panel tested.

The other clones have no significant homology with the published neisserial sequences, and furthermore nor with any published sequence. These clones therefore constitute, with the majority of the other clones isolated, a bank of totally new Nm-specific loci.

EXAMPLE 3

Study of Region 2 of the Nm Chromosome
Determination and Characterization of the Sequence of Region 2

PCR amplification is carried out with the chromosomal DNA of strain Z2491 of serogroup A, sub-group IV-1 using oligonucleotide primers formulated from each of the sequences of clones of region 2 in several different combinations. The PCR products which overlap are sequenced from the 2 strands using the chain termination technique and automatic sequencing (ABI 373 or 377).

To prolong the sequence beyond the limits of the clones available, partial SauIIIA fragments of 15 kb of the strain Z2491 are cloned in Lambda DASH-II (Stratagene).

The phages containing the inserts overlapping region 2 are identified by hybridization with clones of this region as probes. The DNA inserted is sequenced from the ends of the inserts, and these sequences are used to formulate new primers which will serve to amplify the chromosomal DNA directly, and not the phagic DNA.

An amplification of the chromosomal DNA is obtained using these new primers and those of the sequence previously available.

These PCR products are also sequenced from the 2 strands, which leads to a complete sequence of 15,620 bp (SEQ ID No. 36). The reading frames of this sequence which start with ATG or GTG and are characterized by a high codon usage index are analysed.

This analysis reveals 7 ORFs of this type which fill the major part of the sequence of 15,620 bp. The positions of these ORFs are the following:

ORF-1: 1330 to 2970 (SEQ ID No. 37); ORF-2: 3083 to 9025 (SEQ ID No. 38); ORF-3: 9044 to 9472 (SEQ ID No. 39); ORF-4: 9620 to 12118 (SEQ ID No. 40); ORF-5: 12118 to 12603 (SEQ ID No. 42); ORF-6: 12794 to 13063 (SEQ ID No. 43); ORF-7: 13297 to 14235 (SEQ ID No. 44); and ORF-8: 14241 to 15173 (SEQ ID No.45).

ORF-4 starts with the codon GTG and overlaps a slightly smaller ORF (SEQ ID No. 41) in the same reading frame (10127–12118, frame 2), which starts with the codon ATG.

ORF-4 codes for a protein which has structural homologies with a family of polypeptides comprising pyocins (Pseudomonas aeruginosa), collcins and intimins (Escherichia coli), which are bactericidal toxins (pyocins, collcins) or surface proteins involved in adhesion of bacteria to eukaryotic proteins. ORF-7 encodes a protein, the sequence of which contains a potentially transmembrane region and which has structural homologies with periplasmic proteins or proteins inserted in the external membrane of bacteria. The structural homologies of ORF-4 and ORF-7 have been identified with the aid of the PropSearch program.

Investigation of sequences homologous to other ORFs in GenBank with the aid of the BLAST program revealed a homology between the N-terminal regions of ORF-2 and filamentous haemagglutinin B of Bordetella pertussis (43% similarity, 36% identical over 352 amino acids) and between ORF-1 and the protein fhaC of Bordetella pertussis (35% similarity, 27% identical over 401 amino acids). ORF-1 and ORF-2 are neighbouring genes in the strain Z249I and filamentous haemagglutinin B of Bordetella pertussis and fhaC are neighbouring genes in Bordetella pertussis, which reinforces the probability that these homologies reflect functional homologies.

Confirmation of the specificity of region 2 with respect to Nm

Southern blots are carried out using the DNA probes obtained by PCR amplification of various parts of region 2 using oligonucleotide primers formulated from sequences of clones of region 2.

Figure 4:
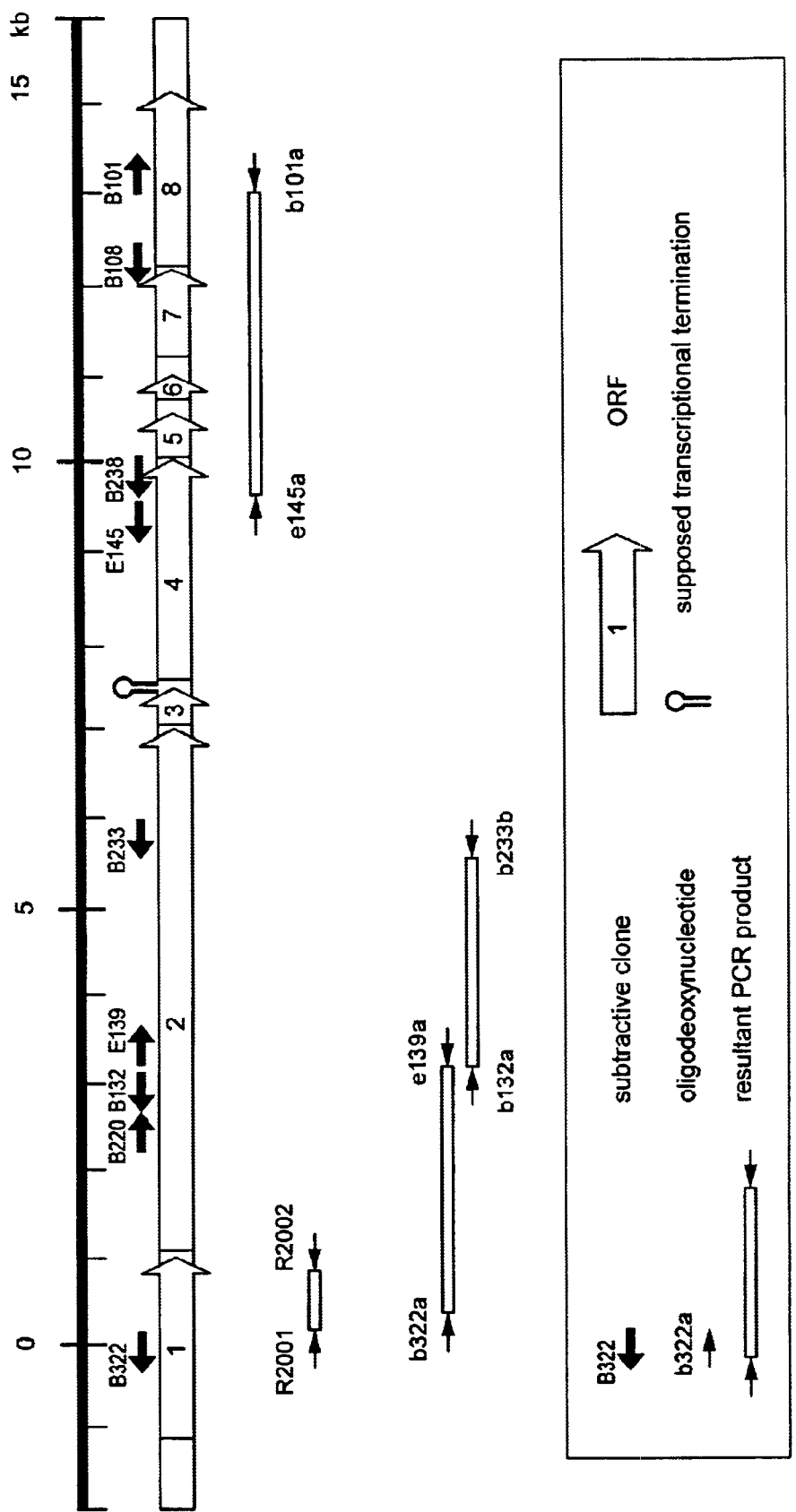

The approximate position of these oligonucleotides is shown on FIG. 4.

These are the oligonucleotides called R2001 (SEQ ID No. 46) and R2002 (SEQ ID No. 47) in one half of ORF-1, the oligonucleotides b332a (SEQ ID No. 48), e139a (SEQ ID No. 49), b132a (SEQ ID No. 50) and b233b (SEQ ID No. 51) in one half of ORF-1+the majority of ORF-2, and the oligonucleotides e145a (SEQ ID No. 52) and b101a (SEQ ID No. 53) in ⅓ of ORF-4+ORF-5 to 7.

The three Southerns are carried out under the following hybridization conditions:
16 h at 65° C.,
NaPO$_4$ 0.5 M, pH 7.2
EDTA-Na 0.001 M
1% sodium dodecylsulphate.

For the washing, heating is carried out for 10 min at 65° C., and NaPO$_4$ 0.5 M, pH 7.2; EDTA-Na 0.001 M, 1% sodium dodecylsulphate are used.

Figure 5:
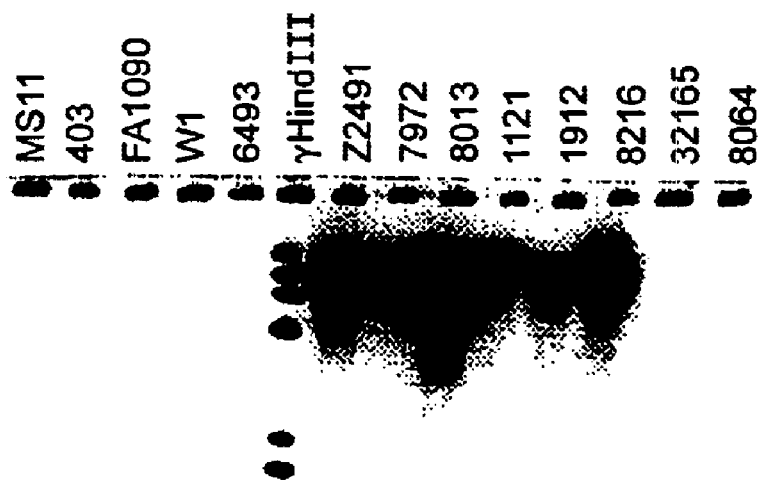
Figure 6:
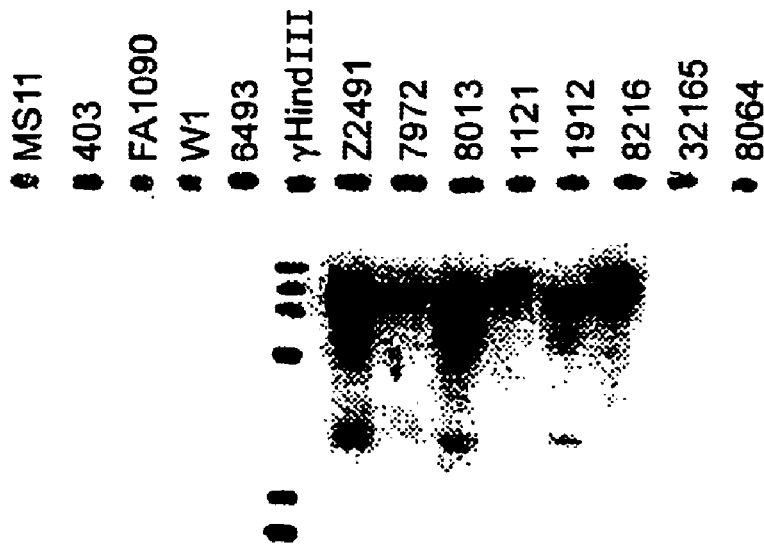
Figure 7:

FIGS. 5, 6 and 7 respectively show the Southern blots obtained with each of the abovementioned ORF parts.

The 14 tracks correspond respectively, in each of the Southerns, to
1: MS11 (Ng)
2: 403 (Ng)
3: FA1090 (Ng)
4: W1 (Ng)
5: 6493 (Ng)
6: marker (lambda hindIII)
7: Z2491 (Nm, gpA)
8: 7972 (Nm gpA)
9: 8013 (Nm, gpC)
10: 1121 (Nm, grouping not possible)

11: 1912 (Nm, gpB)
13: 32165 (Nc)
14: 8064 (Nl).

Given that a panel of strains of *Neisseria* is used in these experiments and that each well is charged with a similar amount of digested DNA, these 3 Southern blots clearly show that the sequences corresponding to region 2 are found in all the meningococci tested and that significant homologous sequences do not exist in the genome of the Ng of the strains tested.

EXAMPLE 4

Identification of Regions of the Nm Genome Absent from Nl and Common with Ng

The technique described in example 1 is followed, but the chromosomal DNA of one strain of Nm (Z2491) and 2 strains of Nl (XN collections), equal parts of the DNAs of which are mixed, is used.

2 subtractions are performed using the R and J series of primers. Three different banks are thus obtained.

Two banks, called Bam and Eco, are obtained respectively by digestion of the chromosomal DNA of Nm Z2491 by MboI and Tsp509I; a third bank, called Cla, which results from digestion of the chromosomal DNA of Nm by MspI, is obtained using the primer set RMsp10, RMsp24, JMsp10 and JMsp24. All the primers used are shown in the following table 2.

TABLE 2

Adapters for differential banks

| Chromosomal DNA digested by | Cloning in pBluescript by |
|---|---|
| MboI → | BamHI |
| Tsp509I → | EcoRI |
| MspI → | ClaI |

First subtraction cycle

```
                                              (SEQ ID No.54)
RBam12:   3' AGTGGCTCCTAG 5'
                                              (SEQ ID No. 55)
RBam24:   5' AGCACTCTCCAGCCTCTCACCGAG 3'
                                              (SEQ ID No.56)
REco12:   AGTGGCTCTTAA
                                              (SEQ ID No. 55)
RBam24:   5' AGCACTCTCCAGCCTCTCACCGAG 3'
          (REco 24 = RBam 24)
                                              (SEQ ID No.57)
RMsp10:   AGTGGCTGGC
                                              (SEQ ID No. 58)
RMsp24:   5' AGCACTCTCCAGCCTCTCACCGAC 3'
Second subtraction cycle
                                              (SEQ ID No.59)
Jbam12:   3' GTACTTGCCTAG 5'
                                              (SEQ ID No. 60)
JBam24:   5' ACCGACGTCGACTATCCATGAACC 3'
                                              (SEQ ID No. 61)
JEco12:   GTACTTGCTTAA
                                              (SEQ ID No 60)
JBam24:   5' ACCGACGTCGACTATCCATGAACG 3'
          (JEco 24 = TBam 24)
                                              (SEQ ID No. 62)
JMsp10:   GTACTTGGGC
                                              (SEQ ID No. 63)
JMsp24:   5' ACCGACGTCGACTATCCATGAACC 3'
```

After 2 subtractions, the entire product of each amplification is labelled and used as a probe.

The subtractive banks are checked by Southern blotting over a panel of 12 strains of *Neisseria* (chromosomal DNA cut by ClaI). The hybridization conditions are identical to those given in example 1.

Figure 8A:
Figure 8B:
Figure 8C:
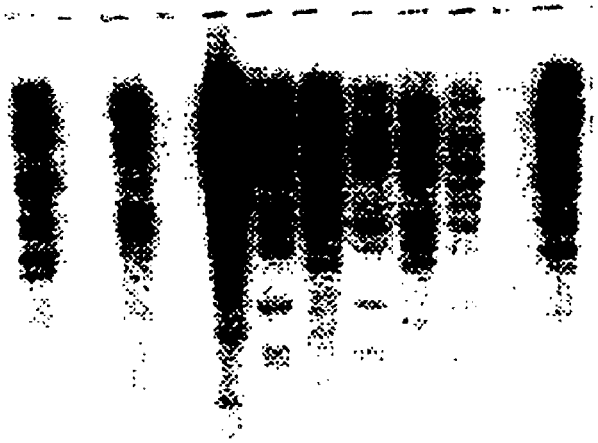

These Southern blots are shown on FIGS. 8A to 8C, which relate respectively to the MboI/BamHI bank, to the MspI/ClaI bank and to the Tsp509I/EcoRI bank.

The 12 tracks correspond respectively, to
1: Nm Z2491 (group A)
2: Nl 8064
3: Nm 8216 (group B)
4: Nl 9764
5: Nm 8013 (group C)
6: Ng MS11
7: Nm 1912 (group A)
8: Ng 4C1
9: Nm 1121 (grouping not possible)
10: Ng FA1O9O
11: Nc 32165
12: Nm 7972 (group A)

Examination of the Southern blots shows that the sequences contained in each bank are specific to Nm and are not found in Nl. Furthermore, the reactivity found with the strains of Ng suggests that some of these sequences are present in Ng.

Figure 9:
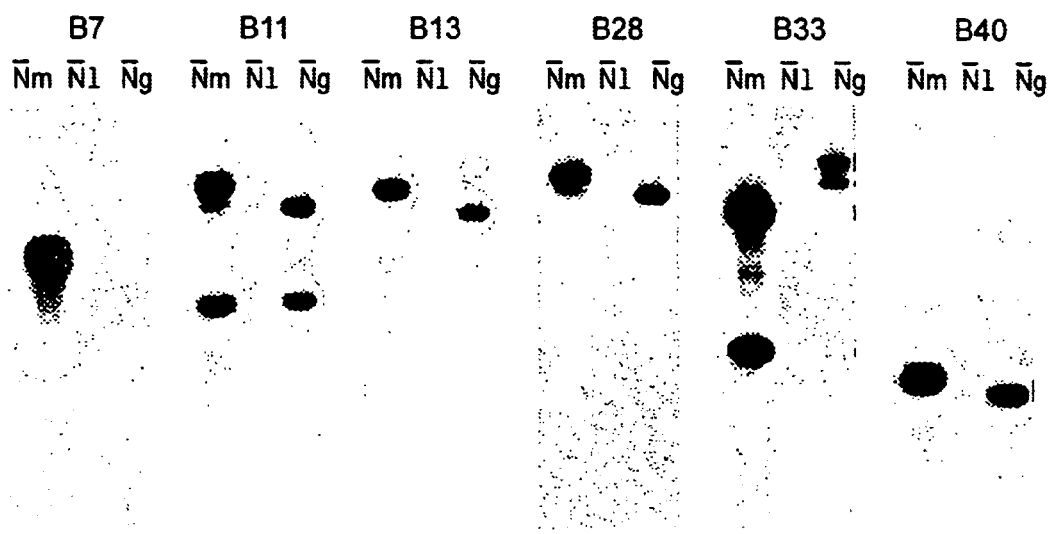
Figure 10:
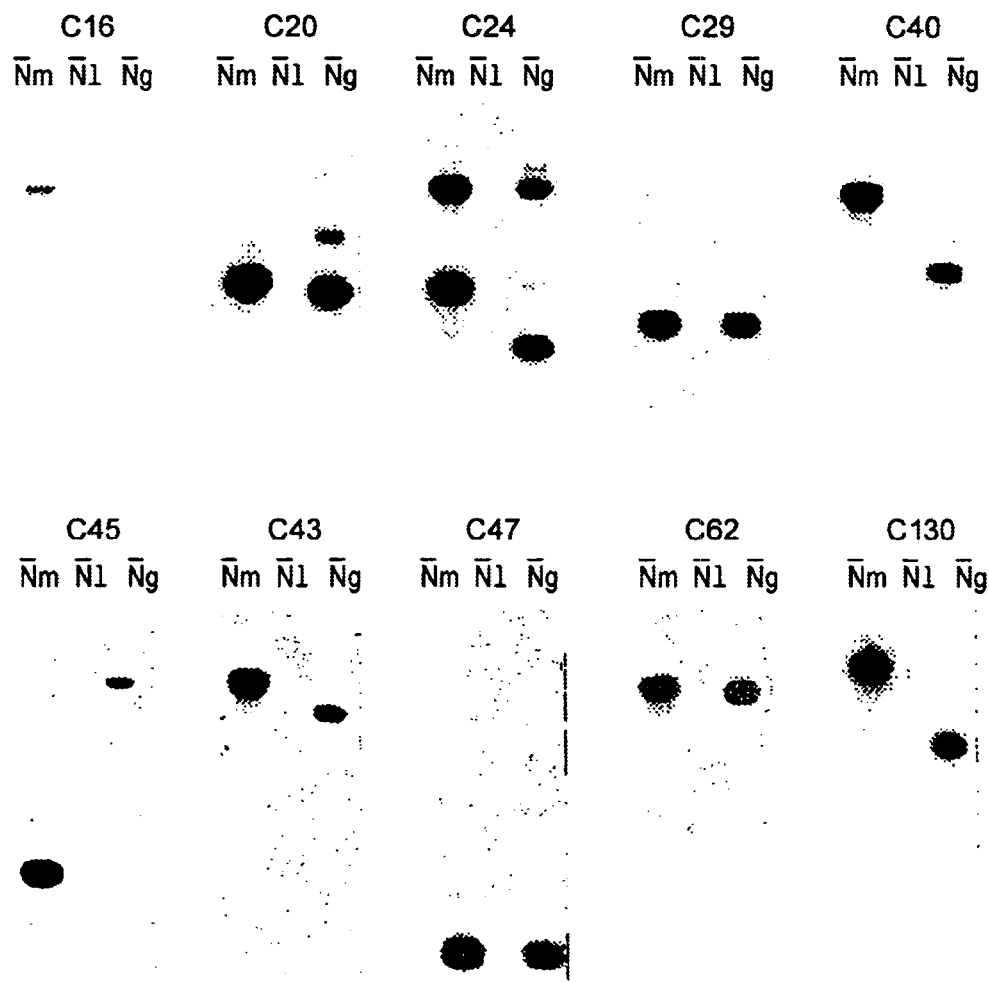
Figure 11:
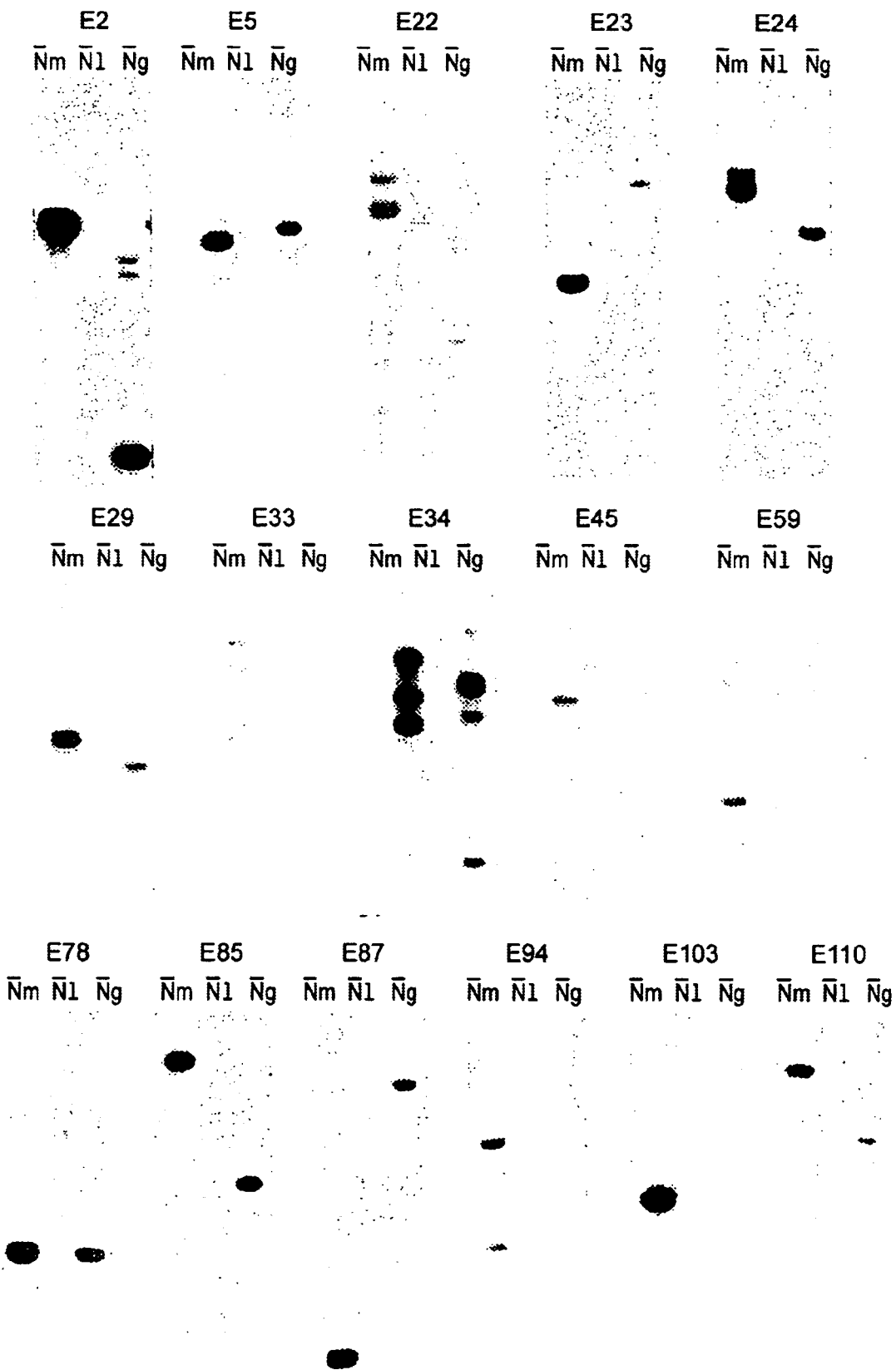

Each of these banks was then cloned in pBluescript at the BamHI site for Bam, or the EcoRI sit for Eco, or the ClaI site for Cla. In order to confirm the specificity of the clones with respect to the Nm genome, restriction of the individual clones and radiolabelling thereof were carried out. The clones showing reactivity for both Nm and Ng were kept for subsequent studies. These clones are shown on FIGS. 9, 10 and 11, which give the profiles with respect to Nm, Nl and Ng of 5 clones of the Bam bank (FIG. 9), 16 clones of the Eco bank (FIG. 10) and 13 clones of the Cla bank (FIG. 11).

These clones were sequenced using universal and reverse primers. They are
Bam clones
partial B11 of 140 bp (SEQ ID No. 66), partial B13 estimated at 425 bp (SEQ ID No. 67), B26 of 181 bp (SEQ ID No. 68), B33 of 307 bp (SEQ ID No. 69), B40 of 243 bp (SEQ ID No. 70),
Cla clones
C16 of 280 bp (SEQ ID No. 72), partial C20 estimated at 365 bp (SEQ ID No. 73), partial C24 estimated at 645 bp (SEQ ID No. 74), partial C29 estimated at 245 bp (SEQ ID No. 75), C34 of 381 bp (SEQ ID No. 76), C40 of 269 bp (SEQ ID No. 77), C42 of 203 bp (SEQ ID No. 78), p C43 of 229 bp (SEQ ID No. 79), C45 of 206 bp (SEQ ID No. 80), C47 of 224 bp (SEQ ID No. 81), C62 of 212 bp (SEQ ID No. 82), and C130 (5' . . . ) estimated at 900 bp (SEQ ID No. 83), and
Eco clones
E2 of 308 bp (SEQ ID No. 84), partial E5 estimated at 170 bp (SEQ ID No. 85), partial E22 estimated at 300 bp (SEQ ID No. 86), E23 of 273 bp (SEQ ID No. 87), E24 of 271 bp (SEQ ID No. 88), E29 of 268 bp (SEQ ID No. 89), partial E33 estimated at 275 bp (SEQ ID No. 90), partial E34 estimated at 365 bp (SEQ ID No. 91), E45 of 260 bp (SEQ ID No. 92), E59 estimated at greater than 380 bp (SEQ ID No. 93), E78 of 308 bp (SEQ ID No. 94), E85 of 286 bp (SEQ ID No. 95), E87 of 238 bp (SEQ ID No. 96), partial E94 greater than 320 bp (SEQ ID No. 97), partial E103 greater than 320 bp (SEQ ID No. 98) and E110 of 217 bp (SEQ ID No. 99).

Mapping of each clone was carried out on the chromosome of Nm Z2491 as described in example 1. The results obtained are given on the right-hand part of FIG. 2. It is found that these clones correspond to regions called 4 and 5. These regions are therefore made up of sequences present both in Nm and in Ng, but not found in Nl. It is therefore regarded that these are sequences which code for virulence factors responsible for the initial colonization and penetration of the mucosa. Region 4 is located between argF and regF on the chromosome of Nm 2491 [sic], and region 5 is located between the lambda 375 marker and penA. This region probably contains sequences which code for an Opa variant and a protein which binds transferrin.

A comparison with the known sequences in the databanks has half [sic] that in region 4 only the clone C130 has a homology, that is to say with MspI methylase. In region 5, no homology with known sequences was found with the clones C8, E2, B40, C45, E23 and E103. For the other clones, the homologies are the following:

B11 arginine decarboxylase SpeA; C29 arginine decarboxylase SpeA; C62 oxoglutarate/malate transporter; repetitive DNA element; E34 repetitive DNA element; E94 murine endopeptidase MepA; C47 citrate synthase PrpC; E78 citrate synthase PrpC

EXAMPLE 5

Demonstration of the Presence of One or More Strains of *Neisseria meningitidis* in a Biological Sample A biological sample of the cephalorachidian fluid, urine, blood or saliva type is taken.

After filtration and extraction, the DNAs present in this sample are subjected to gel electrophoresis and transferred to a membrane by Southern blotting.

A nucleotide probe constructed by labelling SEQ ID No. 5 with $^{32}P$ is incubated with this transfer membrane.

After autoradiography, the presence of reactive band(s) allows diagnosis of the presence of *Neisseria meningitidis* in the sample.

EXAMPLE 6

Vaccine Composition Including in its Spectrum Antimeningococcal Prophylaxis and Intended for Prevention of any form of Infection by *Neisseria meningitidis*

The peptide coded by a sequence including SEQ ID No. 10 is conjugated with a toxin.

This conjugated peptide is then added to a composition comprising the anti-*Haemophilus* and antipneumococcal vaccine, or any other childhood vaccine.

After having been sterilized, the resulting composition can be injected parenterally, subcutaneously or intramuscularly.

This same composition can also be sprayed on to mucosa with the aid of a spray.

What is claimed is:

1. An isolated DNA which is specific to *Neisseria meningitidis* (Nm) and *Neisseria gonorrheae* (Ng), and hybridizes on a Southern blot to SEQ ID NO:95 and does not hybridize on a Southern blot to a DNA sequence of *Neisseria lactamica* (Nl) strain Nl8064, under the following hybridization conditions: 18 h at 65° C., with a solution comprising 0.5 M NaPO₄ pH 7.2, 0.001 M EDTA-Na, 1% bovine serum albumin and 7% sodium dodocylsulphate, followed by at least two washes in a solution comprising 40 mM Na PO₄ pH 7.2, 1 mM EDTA, and 1% SDST, the final wash being conducted at 85° C. for 5 minutes, or the complement of said isolated DNA which is specific to *Neisseria meningitidis* (Nm) and *Neisseria gonorrheae* (Ng), provided that said DNA or the complement of said isolated DNA is not pilC, or a gene involved in the biosynthesis of any one of the polysaccharide capsule, IgA proteases, pilin, a protein which binds transferin, a protein which binds lactoferin, and an opacity protein said DNA being within an islet involved in the polonization of the nasopharynx or invasion of the submucousal space or systemic dissemination of Nm.

2. A composition comprising the DNA or complement of claim 1 and a carrier.

3. An isolated DNA which is specific to *Neisseria memingitidis* (Nm) and *Neisseria gonorrheae* (Ng), and hybridizes on a Southern blot to SEQ ID NO:95 and does not hybridize on a Southern blot to a DNA sequence of *Neisseria lactamica* (Nl) strain Nl8064, under the following hybridization conditions: 16 h at 65° C., with a solution comprising 0.5 M $NaPO_4$, pH 7.2, M EDTA-Na, 1% bovine serum albumin and 7% sodium dodecylsulphate, followed by at least two washes in a solution comprising 40 mM Na $PO_4$ pH7.2, 1 mM EDTA and 1% SDS, the final wash being conducted at 65° C. for 5 minutes, or the complement of said isolated DNA which is specific to *Neisseria meningitidis* (Nm) and *Neisseria gonorrheae* (Ng), provided that said DNA or the complement of said isolated DNA is not pilC, or a gene involved in the biosynthesis of any one of the polysaccharide capsule, IgA proteases, pilin, a protein which binds transferin, a protein which binds lactoferin, and an opacity protein.

4. A composition comprising the DNA or complement of claim 3 and a carrier.

5. A method of detecting *Neisseria meningitidis* (Nm) or *Neisseria gonorrheae* (Ng) in a sample from a patient said method comprising providing isolated sample DNA of said sample from the patient, contacting said sample DNA with the isolated DNA of claim 1, said contacting being performed under conditions which allow hybridization of said sample DNA and said isolated DNA, and detecting any hybridization of said sample DNA and said isolated DNA, such that said hybridization of said sample DNA and said isolated DNA specifically indicates the presence of said Nm or Ng in said sample, wherein said isolated DNA is specific to Nm and Ng and does not hybridize on a Southern blot to a DNA sequence of *Neisseria lactamica* (Nl) strain Nl8064 under the following hybridization conditions: 18 h at 65° C., with a solution comprising 0.5 M $NaPO_4$ pH 7.2, 0.001 M EDTA-Na, 1% bovine serum albumin and 7% sodium dodecylsulphate, followed by at least two washes in a solution comprising 40 mM Na $PO_4$ pH 7.2, 1 mM EDTA, and 1% SDS, the final wash being conducted at 65° C. for 5 minutes, and wherein said isolated DNA specifically hybridizes to Nm DNA and Ng DNA in the presence of Nl DNA.

6. A method of detecting *Neisseria meningitidis* (Nm) or *Neisseria gonorrheae* (Ng) in a sample from a patient, said method comprising providing isolated sample DNA of said sample from the patient, contacting said sample DNA with the composition of claim 1 under conditions which a low hybridization of said sample DNA and DNA in said composition, and detecting any hybridization of said sample DNA and said DNA in said composition, such that said hybridization of said sample DNA and said DNA in said composition specifically indicates the presence of said Nm or Ng in said sample, wherein said DNA in said composition is specific to Nm and Ng and does not hybridize on a Southern blot to a DNA sequence of *Neisseria lactamica* (Nl) strain Nl8064 under the following hybridization conditions: 16 h at 65° C., with a solution comprising 0.5 M $NaPO_4$ pH 7.2, 0.001 M EDTA-Na, 1% bovine serum albumin and 7% sodium dodecylsulphate, followed by at least two washes in a solution comprising 40 mM Na $PO_4$ pH 7.2, 1 mM EDTA, and 1% SDS, the final wash being conducted at 65° C. for 5 minutes, and wherein said DNA is said composition specifically hybridizes to Nm DNA and Ng DNA in the presence of Nl DNA.

7. A method of detecting *Neisseria meningitidis* (Nm) of *Neisseria gonorrheae* (Ng) in a sample from a patient, said method comprising providing isolated sample DNA of said sample from the patient, contacting said sample DNA with the isolated DNA of claim 3, said contacting being performed under conditions which allow hybridization of said sample DNA and said isolated DNA, and detecting any hybridization of said sample DNA and said isolated DNA, such that said hybridization of said sample DNA and said isolated DNA specifically indicates the presence of said Nm or Ng in said sample, wherein said isolated DNA is specific to Mm and Ng and does not hybridize on a Southern blot to a DNA sequence of *Neisseria lactamica* (Nl) strain Nl8064 under the following hybridization conditions: 16 h at 65° C., with a solution comprising 0.5 M $NaPO_4$ pH 7.2, 0.001 M EDTA-Na, 1% bovine serum albumin and 7% sodium dodecylsulphate, followed by at least two washes in a solution comprising 40 mM Na $PO_4$pH 7.2, 1 mM EDTA, and 1% SDS, the final wash being conducted at 65° C. for 5 minutes, and wherein said isolated DNA specifically hybridizes to Nm DNA and Ng DNA in the presence of Nl DNA.

8. A method of detecting *Neisseria meningitidis* (Nm) or *Neisseria gonorrheae* (Ng) in a sample from a patient, said method comprising providing isolated sample DNA of said sample from the patient, contacting said sample DNA with the composition of claim 4 under conditions which allow hybridization of said sample DNA and DNA in said composition, and detecting any hybridization of said sample DNA and said DNA in said composition, such that said hybridization of said sample DNA and said DNA in said composition specifically indicates the presence of said Nm or Ng in said sample, wherein said DNA in said composition is specific to Nm and Ng and does not hybridize on a Southern blot to a DNA sequence of *Neisseria lactamica* (Nl) strain Nl8064 under the following hybridization conditions: 16 h at 65° C., with a solution comprising 0.5 M $NaPO_4$ pH 7.2, 0.001 M EDTA-Na, 1% bovine serum albumin and 7% sodium dodecylsulphate, followed by at least two washes in a solution comprising 40 mM Na $PO_4$ pH 7.2, 1 mM EDTA, and 1% SDS, the final wash being conducted at 65° C. for 5 minutes, and wherein said DNA is said composition specifically hybridizes to Nm DNA and Ng DNA in the presence of Nl DNA.

* * * * *

UNITED STATES PATENT AND TRADEMARK OFFICE
CERTIFICATE OF CORRECTION

PATENT NO. : 7,029,845 B2  Page 1 of 1
APPLICATION NO. : 09/928457
DATED : April 18, 2006
INVENTOR(S) : Nassif et al.

It is certified that error appears in the above-identified patent and that said Letters Patent is hereby corrected as shown below:

On the Title Page, left hand column, delete the "Assignees" in item (73) and insert the following therefor:

(73) Assignee: Institut National de la Sante et de la Recherche Medicale
   (I.N.S.E.R.M.) (Paris, FR)

Column 121, line 66 (line 6 of claim 1): delete "18h" and insert therefor --16h--.

Column 122, line 62 (line 10 of claim 1): delete "SDST" and insert therefor --SDS--.

Column 122, line 63 (line 11 of claim 1): delete "85" and insert therefor --65--.

Column 123, lines 4-5 (lines 19-20 of claim 1): delete "polonization" and insert therefor --colonization--.

Column 123, line 43 (line 15 of claim 5): delete "18 h" and insert therefor --16 h--.

Column 123, line 57 (line 5 of claim 6): delete "claim 1" and insert therefor --claim 2--.

Signed and Sealed this

Twentieth Day of November, 2007

JON W. DUDAS
*Director of the United States Patent and Trademark Office*

SEQUENCE LISTING (1) GENERAL INFORMATION:

(iii) NUMBER OF SEQUENCES: 99

(2) INFORMATION FOR SEQ ID NO: 1:

(i) SEQUENCE CHARACTERISTICS:
      (A) LENGTH: 257 base pairs
      (B) TYPE: nucleotide
      (C) STRANDEDNESS: single
      (D) TOPOLOGY: linear (ii) MOLECULE TYPE: DNA (genomic)

(vi) ORIGINAL SOURCE:
      (A) ORGANISM: Neisseria meningitidis
      (B) STRAIN: Z2491

(xi) SEQUENCE DESCRIPTION: SEQ ID NO: 1:

```
GATCCGCTGC CGGCAGACGA ATATCAAGAC ATCTTCGATT TTATGAAACA GTATGACTTG      60

TCTTACCCGT ATGAATATCT GCAGGATTGG ATAGATTACT ATACGTTCAA AACCGATAAG     120

CTGGTATTTG GTAACGCGAA GCGAGAGTGA GCCGTAAAAC TCTGAGCTCC TGTTTTATAG     180

ATTACAACTT TAGGCCGTCT TAAAGCTGAA AGATTTTCGA AAGCTATAAA TTGAAGCCCT     240

TCCACAGTAC ATAGATC                                                    257
```

(2) INFORMATION FOR SEQ ID NO: 2:

(i) SEQUENCE CHARACTERISTICS:
      (A) LENGTH: 276 base pairs
      (B) TYPE: nucleotide
      (C) STRANDEDNESS: single (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 2:

GATCATGTTC AAATAGATAG GCATGGGAAG CTGCAGCTCT AACGTCCATG AAAATATGTT    60

GCATAGCTGC AAGCGGAACG CCTTTTCTTT CATCTACATA ATCTATAGAG TCAAGGCAAC   120

CGCTATTGAA ATTAGCAGTA TTGCCTATGA TTACATTAGT AATATGCTCA TACCATTTTT   180

GGGTGGTCAT CATATTGTGC CCCATTGTTA TCTCCTTATA TTGGTTTTAG AAGGAACTTT   240

GACAGGAAGA ATAACGGCCT TACCTGTTTG ACGATC                            276

(2) INFORMATION FOR SEQ ID NO: 3:

(i) SEQUENCE CHARACTERISTICS:
        (A) LENGTH: 428 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 3:

GATCTGGTGG TGTTTGCACA GGTAGGCGCA TACTTGTTCG GGACTGAGTT TGCGGCGGAT    60

AAGGGTGTCG ATGTGCTGAA TCAGCTGCGA ATCGAGCTTA TAGGGTTGTC GCTTACGCTG   120

TTTGATAGTC CGGCTTTGCC GCTGGGCTTT TTCGGCGCTG TATTGCTGCC CTTGGGTGCG   180

GTGCCGTCTG ATTTCGCGGC TGATGGTGCT TTTGTGGCGG TTAAGCTGTT TGGCGATTTC   240

GGTGACGGTG CAGTGGCGGG ACAGGTATTG GATGTGGTAT CGTTCGCCTT GGGTCAGTTG   300

CGTGTAGCTC ATGGCAATCT TTCTTGCAGG AAAGGCCGTA TGCTACCGCA TACTGGCCTT   360

TTTCTGTTAG GGAAAGTTGC ACTTCAAATG CGAATCCGCC GACCTCTTTC AGTTACAGCA   420

GCTTGATC                                                           428

(2) INFORMATION FOR SEQ ID NO: 4:

(i) SEQUENCE CHARACTERISTICS:
        (A) LENGTH: 390 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 4:

GATCCTGCAT TGACATCGGC CTTGGCTGTC AGGGTATTGT GACCGGTAAA GTCGGCATTA    60

CCGTTGGCCA ATAAGGATAC ATGACCGTCT GCAGAAACAG CATGAAGGCC GTCTGAAACG   120

ATATTGCCCT GCAATGCGGT GGTTTCGAGA GCCTTGGCTG CGTTCAGCTT GGTATTGCGA   180

AGCTGAATAT TGCCTTTGGC TGCCTGAATG TGCAGATTAC CCGAGTTGGT ACGCAGATTG   240

GTATTGGTAA CATTCAGCAA GCCTGCCTCC ACACCCATGT CTTTTGAGGC AGTGAGGGTT   300

```
TTACTGGTGC CGGTAATATG GGCAGCGTTA TCCGATTTCA ATGGATGCT GGCCGGCAGA    360

CAAATCTTTA TCAACATTCA AATTCAGATC                                   390
```

(2) INFORMATION FOR SEQ ID NO: 5:

(i) SEQUENCE CHARACTERISTICS:
        (A) LENGTH: 177 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 5:

```
GATCAGATTG GTGAAGACGG TATTACCGTC AATGTTGCAG GCCGTTCGGG ATATACGGCG    60

AAAATCGACG TGTCTCCGAG TACCGATTTG GCGGTTTATG GCCATATTGA AGTTGTACGG   120

GGTGCAACGG GGTTGACCCA ATCCAATTCA GAGCCGGGTG AACCGTCAA TTTGATC      177
```

(2) INFORMATION FOR SEQ ID NO: 6:

(i) SEQUENCE CHARACTERISTICS:
        (A) LENGTH: 341 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 6:

```
GATCAATGAT GCTACTATTC AAGCGGGCAG TTCCGTGTAC AGCTCCACCA AAGGCGATAC    60

TGAATTGGGT GAAAATACCC GTATTATTGC TGAAAACGTA ACCGTATTAT CTAACGGTAG   120

TATTGGCAGT GCTGCTGTAA TTGAGGCTAA AGACACTGCA CACATTGAAT CGGGCAAACC   180

GCTTTCTTTA GAAACCTCGA CCGTTGCCTC CAACATCCGT TGAACAACG GTAACATTAA   240

AGGCGGAAAG CAGCTTGCTT TACTGGCAGA CGATAACATT ACTGCCAAAA CTACCAATCT   300

ACTCCC GGCAATCTGT ATGTTCATAC AGGTAAAGAT C                          341
```

(2) INFORMATION FOR SEQ ID NO: 7:

(i) SEQUENCE CHARACTERISTICS:
        (A) LENGTH: 164 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 7:

```
GATCCAACTG TTTGATTTTA CTGGCTGCTT CTCCATGCGC GGTATTGACC AAAGCCGCAA    60

GGATATTCGC TTCCAGATTG TCTTTCAGGC TGCCGCCGTT GACAGCGGTA TTAATCAGTG   120

CGGCACTGCC CGCATTGGCT AGGTTGACGG TCAGGTTGTT GATC                   164
```

(2) INFORMATION FOR SEQ ID NO: 8:

(i) SEQUENCE CHARACTERISTICS:
        (A) LENGTH: 219 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 8:

| | | | | | |
|---|---|---|---|---|---|
| GATCAATCAC | ACATCTTGTC | ATTTTTTCGA | TTCCTTCATT | TCGGTTTCTA | ATGTTTCAAT | 60 |
| TCTTGCGGCC | ATTTCCTGAA | TGGCTTTAGT | CAAAACGGGG | ATGAACGCTT | CGTATTCGAC | 120 |
| GGTGTAGGTA | TCGTTTGTTT | TATTTACCAT | CGGCAATCGA | CCATATTCAT | CTTCCAGCGC | 180 |
| AGCAATGTCC | TGGGCAATAA | ACCAATGCCG | CAACCGATC | | | 219 |

(2) INFORMATION FOR SEQ ID NO: 9:

(i) SEQUENCE CHARACTERISTICS:
        (A) LENGTH: 356 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 9:

| | | | | | |
|---|---|---|---|---|---|
| GATCTTGGGT | AAGCCCCCAA | CCTGCATAGA | AAGGCAGGCC | GTAGCAGCTG | ACTTTTTTGC | 60 |
| CGCGCAACAA | GGCTTCAAAA | CCGGTCAGCG | AAGTCATGGT | ATGTATTTCG | TCTGCGTATT | 120 |
| GGAGACAGGT | CAGGATGTCG | GCTTGTTCGG | CGGTTTGGTC | GGCATATCGT | GCAGCATCAT | 180 |
| CAGGGGAAAT | ATGGCCGATG | CGGTTACCGC | TGACTACATC | GGGATGCGGT | TTGTAGATGA | 240 |
| TATAGGCATT | GGGGTTTCGT | TCGCGTACGG | TACGAGCAA | ATCCAGATTG | CGGTAGATTT | 300 |
| GGGGCGAACC | GTAGCGGATA | GACGCATCAT | CTTCAACCTG | GCCGGGAACG | AGGATC | 356 |

(2) INFORMATION FOR SEQ ID NO: 10:

(i) SEQUENCE CHARACTERISTICS:
        (A) LENGTH: 210 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 10:

| | | | | | |
|---|---|---|---|---|---|
| GATCCGCTTT | CAGTTTCCGT | ACCGGTGGCA | TCAGTCAAGT | CCGTTTTGTG | CACCAAACCG | 60 |
| CGTCCATATG | AAACATAAAA | CAAATCGCTT | AAGCCCAAAG | GGTTATCGAA | CGATAAAGCG | 120 |
| ACATTTCCTT | GATATTTGCC | GGTCGTTTTG | CCGCCCGCAT | CATCTATACC | GATACTGAAC | 180 |
| CGTATGGGTT | TATTCTGCTG | CCATTTGATC | | | | 210 |

(2) INFORMATION FOR SEQ ID NO: 11:

(i) SEQUENCE CHARACTERISTICS:
        (A) LENGTH: 259 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 11:

```
GATCCCGAAA CGCAATTGGT CGAAAGCTAT ATGCTGAACG ATGTGTTGCG GTTTTGGGAC      60

AGCGCAGGTT TGGGCGATGG GAAAGAAGCC GACCGCGCCC ATCGGCAAAA ACTGATTGAT     120

GTCCTGTCTA AAACCTATAC TCATTCGGAT GGGCAGTGGG GCTGGATAGA TTTGGTGTTC     180

GTTATCCTTG ACGGCAGCTC CGCGATTTTG GGTACGGCCT ATGATTTGTT GAGGGATGTT     240

ATCCTTAAAA TGATTGATC                                                  259
```

(2) INFORMATION FOR SEQ ID NO: 12:

(i) SEQUENCE CHARACTERISTICS:
        (A) LENGTH: 436 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 12:

```
GATCAAATGG ATGATTTATA TAGAATTTTC TTTTACGACT GCGTGCCGTT TGAAAAGAAA      60

ATGCACAATC CCGTATCTCA TCGTGCCATA GATTTTTCAA AGACTCCGGA AGCCATATTT     120

CGTTGCAATC TGCATACCGA ATTGAAGAAG AAGCGTAAAT TAGCGTTACG TTTAGGCAAG     180

CTGTCGGACA ATACAGCATG GATATTAAAA CCCCAAGTCA TGAAAAATCT TCTGAAAAAC     240

CCGTCAACTC AAATTACGGA AAACGATGTC GTGCTCGATG TTAAACAAAA AGGTGTAGAT     300

ATGCGTATAG GCTTGGATAT TTCATCTATT ACCTTAAAAA AACAAGCCGA TAAAATCATC     360

TTGTTTTCTG GTGATTCCGA TTTTGTCCCA GCAGCCAAAT TAGCCAGACG GGAAGGTATC     420

GATTTTATTC TTGATC                                                     436
```

(2) INFORMATION FOR SEQ ID NO: 13:

(i) SEQUENCE CHARACTERISTICS:
        (A) LENGTH: 363 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 13:

```
GATCGTTTTA CGTCGCAATC GAGCTTTGTG GTGCGCTCGC CTAAAAGCCA ATCTTCTCTC      60
```

AATGGCCTGG GTGCCATTTT GCAGGGCACA GGTTTTGCCC GTGCGCAAGA CGATATTTAT    120

ACCGTGCAGG AATATATGCA GTCGCGTTCG GCTTTGGATG CGTTGCGTAA GAAAATGCCC    180

ATTCGCGATT TTTATGAAAA AGAAGGCGAT ATTTTCAGCC GTTTTAATGG TTTTGGCCTG    240

CGTGGCGAGG ATGAGGCGTT TTATCAATAC TACCGTGATA AGGTATCCAT CCATTTTGAC    300

TCTGTCTCAG GCATTTCCAA TTTGAGCGTT ACATCGTTTA ATGCCGGTGA ATCTCAAAAG    360

ATC                                                                 363

(2) INFORMATION FOR SEQ ID NO: 14:

(i) SEQUENCE CHARACTERISTICS:
        (A) LENGTH: 314 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 14:

GATCTTGCGT CATTTATATC TTCACCGATA TTGCAATTAC CGCCGTTCCA GTTGAAATAA     60

CAACGACTAA AATTGTAGTT CCTAAAAGAA TCATTCCTAT TCTTGCGTAC CATTTCCCAA    120

TAATTGCGCC CGACAATTTC CATTTAATGC TCCATCAGTT CTTTTACTTC CGGAAATCTG    180

CTGTAATCTG ACATAAGACG CATAATTGAA CTATCAACGC CGTAACAGCC ATAGGTTTTA    240

ATACCGTTTT CGGCGTGTTC CCAAATGCAA TTACTGTATT CGTAGCCTTT TACAAATTTA    300

TCGGTTTCGG GATC                                                     314

(2) INFORMATION FOR SEQ ID NO: 15:

(i) SEQUENCE CHARACTERISTICS:
        (A) LENGTH: 256 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 15:

GATCATACGA ATCTACCCTA AAATACCCCG TCGCCGATTT AGGATTGGCT ACATAAAGCT     60

CATTATAAGG GTATTTTGAT GACATGATAC GGTTAAATTC ATTGCCGTTG TTTATCCTGA    120

TTCTATAAAT TGGTTCAACA GCAAAGCCTC TGGATTCCCT TAATTGATTA TAATATTGCC    180

TGTATGTTTG TACATCATGT CTTGTCCACG GCTCTCCAGG AGTCCTCAGA ATAGCAATCC    240

CGTTAAATTT CGGATC                                                   256

(2) INFORMATION FOR SEQ ID NO: 16:

(i) SEQUENCE CHARACTERISTICS:
        (A) LENGTH: 235 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
    (A) ORGANISM: Neisseria meningitidis
    (B) STRAIN: Z2491

(xi) SEQUENCE DESCRIPTION: SEQ ID NO: 16:

```
GATCCACGCC TGTGCCTACC TTGGCTTTTT GTTCGCCAAA CAAGGCATTT AAGGTTGAGG      60

ACTTGCCGAC ACCTGTCGCA CCGACAAGCA AGACATCCAA ATGACGGAAA CCGGCTGCTG     120

TGACTTTTTG CCCGATTTCA GAAATACGGT AACGATGCAT ATGCGCTCCT ACCAGCCAAA     180

AAAAGAAGCA ACCGTGCTAA TCGCCCCTCC AATCGCTTTT GCAGCACCGC CGATC          235
```

(2) INFORMATION FOR SEQ ID NO: 17:

(i) SEQUENCE CHARACTERISTICS:
        (A) LENGTH: 259 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 17:

```
GATCCAACGG GCATCGCTGT CCTTACTCGG TGTGGTTTGA CCGCTGATTT GTCCTTCTTC      60

GTCAACTTCT ATGGCCTGAC GCTGTTTGCT GCCGGCGGTC TGGATAATGG TGGCATCAAC     120

GACGGCGGCG GATGCTTTCT CTATTTTTAG GCCTTTTTCG GTCAGTTGGC AGTTAATCAG     180

TTTGAGTAAT TCGGACAGGG TGTCGTCTTG CGCCAGCCAG TTGCGGTAGC GGCATAAGGT     240

ACTGTAATCG GGGATGATC                                                  259
```

(2) INFORMATION FOR SEQ ID NO: 18:

(i) SEQUENCE CHARACTERISTICS:
        (A) LENGTH: 201 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 18:

```
GATCTGTGCC GTTGATTTTA TCTTTCAGAT GCAGCATCGA ATATCGGAAA GCCAAATCAG      60

CAATTCTTTT TGCATCGTGT GGATTTTGAG ACGGGCCTAA TGACCGTACC CGCTTAATAA     120

AAAATGCACC GTCAATCAAA ATGGCGGTTT TCATATTGCT TCCCCTATAT TTGTCAAAGA     180

TATAAAAAAG CCCTTGGGAT C                                               201
```

(2) INFORMATION FOR SEQ ID NO: 19:

(i) SEQUENCE CHARACTERISTICS:
        (A) LENGTH: 334 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:

(A) ORGANISM: Neisseria meningitidis
            (B) STRAIN: Z2491

(xi) SEQUENCE DESCRIPTION: SEQ ID NO: 19:

AATTCAAAGG AGGCATTTGT TGCAAGAAAA GTACAAAGTG ATTTGCAAAA AGCATTGAAT      60

GCTAGCAACT ATAACAAGCA GCAATATGCA AGACGTGCGG CAACAGCGTT AGAGAATGCT     120

TCAAAATCAA AAGTTATGGC AGCGAATTCT TTTTGATCTA TCTTGTGCGA ACGGGTCAAA     180

TATTCTTCGT ACATTGAGTT AATCGTACCA ATCGCCCTAA CCACATTTTC ATCAGAAAAT     240

ATGGAAATAA TAGCATCCCT ATACGCACCT AGTGTAATAT TGTTTCTATT ATTAGTTATA     300

GCATTATTCG AATACATAAT AGCACCTCCA AATT                                 334

(2) INFORMATION FOR SEQ ID NO: 20:

(i) SEQUENCE CHARACTERISTICS:
        (A) LENGTH: 238 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 20:

AATTCCTGCG CACCTTTGCC GATGGGGAGA TAATCGCCTT TTTGCAGCAT TCTGCCCTGA      60

TGGCCGCCGA AACCGGCTTT CAGGTCGGTA CTTCTCGAAC CCATCACTTC CGGCACATCA     120

AATCCGCCCG CCACGCACAC ATAGCCGTAC ATGCCCTGCA CGGCACGCAC CAGTTTCAAG     180

GTCTGCCCTT TGCGGGCGGT ATAACGCCAA TACGAATAGA CCGGTTCGCC GTCCAATT      238

(2) INFORMATION FOR SEQ ID NO: 21:

(i) SEQUENCE CHARACTERISTICS:
        (A) LENGTH: 249 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 21:

AATTGGGCGA GATGCTGCCG GAAACGGATT TAAAACAGAT TGCGGCGGCA GTGTTGAAGA      60

CGAACGATGA GGCGGCATTG CAGAAGGTGG TGAAAACGGC CAAAGGCAAT GCGCGGAAAC     120

TGTCGAAGCT GCTGCTGATT GTGGACTATT TGTTGCAGGT TAACCCTGAT GTTGATTTGG     180

ATGATGATGT AATCGAACAC GCGGAAACCT ATTTAATCCA CTAAACCTTT GACAGATAAG     240

GCAATAATT                                                             249

(2) INFORMATION FOR SEQ ID NO: 22:

(i) SEQUENCE CHARACTERISTICS:
        (A) LENGTH: 212 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 22:

AATTTATGTA CGGTTTTGCC GTTTGCAGTC AGCCAGTCGG CAAGGCGCAG AAAAAAATCG    60

CCGACAGGGC CTTGAAGCAG CAGGATATTT TCTGCGCTTT CAAGCAGGTT TTGCAGGTTA   120

TTTTTGAGGA CGGTCTGTTT CATGTTGCAA TGTGGTTTTG TTTTTTATGT AATAGTTTTA   180

GGTTGAACTT TCAAGCATAC GCCAAGAGAA TT                                 212

(2) INFORMATION FOR SEQ ID NO: 23:

(i) SEQUENCE CHARACTERISTICS:
        (A) LENGTH: 227 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 23:

AATTCAGTGC CTGCGTCATA TCACGGCTAC CTTGTGGTTC AGGGTTACTG TATCGCCCGC    60

GGCATCGACG GCTTCAATAT GCAGCTTCAG CCAGCCGTGC TGCGGGGCGG ATGCGGTTAC   120

TTGGATGGAT TGGGCGCGTT TGGACTGAAT CACGGGCTGC AAGGCTTGCT CGGCGTACTG   180

TTTGGCCAGT ACTTCGATGC GCTTTAAATG CTTTTGGCGG CGCAATT                227

(2) INFORMATION FOR SEQ ID NO: 24:

(i) SEQUENCE CHARACTERISTICS:
        (A) LENGTH: 167 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 24:

GATCCAGGAC TCAAAAACCG ATTTCCTAAT AGAGTGTCTA ATATCCCAAT CTTTTTTACC    60

CCCTCTGCTG TAGAATTGAT AGAGAAAGTT TGTCTATCTT TTTCATATAC CCATGCCTTC   120

TTTTTATCAT TGTAGCTAAC ATAACCGCCA AACAATGCTT CTAGATC                167

(2) INFORMATION FOR SEQ ID NO: 25:

(i) SEQUENCE CHARACTERISTICS:
        (A) LENGTH: 251 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 25:

```
AATTCTTGCG GCCATTTCCT GAATGGCTTT AGTCAAAACG GGGATGAACG TTTCGTATTC      60

GACGGTGTAG GTATCGTTTG TTTTATTTAC CATCGGCAAT CGACCATATT CATCTTCCAG    120

CGCAGCAATG TCCTGGGCAA TAAACCAATG CCGCAACCGA TCTTCTTTAT GACTGCCGTC    180

CTTGATTGGA TTCGCCCACC ATTCGCGGAC TTTGTCCGCT CGTTCATCTG CCGGCAAGTC    240

TTTGAATAAT T                                                         251
```

(2) INFORMATION FOR SEQ ID NO: 26:

(i) SEQUENCE CHARACTERISTICS:
        (A) LENGTH: 207 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 26:

```
AATTCCCGAC TATCGCGGAT GCGTAGTTTT TGCCGGTGGG CAAGAGCAGG TGTGGGATAA      60

GTTAGGTGAT TTGCCCGATG GCGTCAGCCT GACCCCGCCT GAATCGGTAA ATATTGACGG    120

CTTAAAATCC GTAAAACTCG TCGCATTAAA TGCTGCCGCT CAGGCTTTTA TTAACAAGCA    180

CGCCGGTATC GACAGCGTAC CTGAATT                                        207
```

(2) INFORMATION FOR SEQ ID NO: 27:

(i) SEQUENCE CHARACTERISTICS:
        (A) LENGTH: 379 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 27:

```
AATTGTTTGG GAATAATCCA AACAAACAGC ATCAGGATAG CGGCGGCGGT CAGGCTGCCT      60

GAAAGGATTT TGCCGGGGTT TTTTGTAGGC AAAGCGGACG AGAAACCAAA GCAACAGCAG    120

CATGGTGTCC CAATAGCCGA TTGAGAATAG GATGGCCAAA CCTTCTAGGA AATGGCGTAA    180

ATCGTTTGTG GTAACCATGG GTAGTTCCTG TGGTTAAATG TGCAGGCTGC TTTTTGCCGA    240

ACCTTGCCGC ATCTCAAAAG CAGCCTGCGC TTCAGCGTTG CGTTACGCAG TAAAATAATG    300

AATATTTGTA ACGGCTTGGG TATTTTTTGT CAATATTCCC GCCCTTCCCT TAACAGCTGC    360

CGCGCTTTCC GTTAAAATT                                                 379
```

(2) INFORMATION FOR SEQ ID NO: 28:

(i) SEQUENCE CHARACTERISTICS:
        (A) LENGTH: 274 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:

(A) ORGANISM: Neisseria meningitidis
        (B) STRAIN: Z2491

(xi) SEQUENCE DESCRIPTION: SEQ ID NO: 28:

AATTCGCCGA AATCAGGCTG CTGCTCGATA ATCGGCGCGG CCGATTGGCG TTGTGCCTCG    60

ATTAAATCCA TCTTGTCTTG CAGACGTTTG GCCTGGCCTT TGCGGCGGCG TTCGGCCAGT   120

TGTTCCATCC GCGTTTCCGC AAATGCCGCC CGTTTGTTGC CGTTGAATAC CGCTTTGCAA   180

ATCACCTTGC CCTGCATATC CTTCACAATC ACATGGTCGG CATCGTGGAT GTCGTAAGCC   240

ACCCGTACCT TCTGACCGCT GTAATCCAGC AATT                               274

(2) INFORMATION FOR SEQ ID NO: 29:

(i) SEQUENCE CHARACTERISTICS:
        (A) LENGTH: 263 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 29:

AATTCCGTTC TTATTGGGCT TTTTCCATCC ATCGGGTATG CCTGAAGGGA ACGCAAACCC    60

TGCCACTTGC CCATCGCTCC ATTCCCGCAT TAGCGCGTCT GACGGCAAGT GTTCTCGCGC   120

CCAATCAAGC CACGCCTGCC GCATTGCGGC CTTGTCCTGC TGAAAACTTC GCAGTGCTTT   180

TGCAACCGGC CCATCATTAA CTTCAATCAA ATAAATCATT ATATTTGCGT TCATTTTTCC   240

TACACCTTCG CCACATCCAA ATT                                           263

(2) INFORMATION FOR SEQ ID NO: 30:

(i) SEQUENCE CHARACTERISTICS:
        (A) LENGTH: 316 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 30:

AATTGTTCAA GAAAAAAGTC GGCACGGCGC GGCAACGGGG AAAATGCGTT GACGCCGTCT    60

TTTTCTAAGG TGATGTAGTA GGGGCGGAAA TAGCCTTCTT CAAACGCCCA GAAACTGGCT   120

TGGTTTTCGT TTGCAATGCG TTTTGCAATG ACGTGATAAG GGCGTGTGTC GCCAAAGCAG   180

ACAACGGCCT GGATGTGATG TTGAGTGATG TATTCTTGCA AAAACTCAGG AAAGGCGTCG   240

TAGTTGTCGT TAAAAACAAC GGTATGCGCT TGAGTGGGCG GATAAAAATA GTCGTCGCCT   300

GCATTAAAGT TGAATT                                                  316

(2) INFORMATION FOR SEQ ID NO: 31:

(i) SEQUENCE CHARACTERISTICS:
        (A) LENGTH: 324 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
    (A) ORGANISM: Neisseria meningitidis
    (B) STRAIN: Z2491

(xi) SEQUENCE DESCRIPTION: SEQ ID NO: 31:

```
AATTCAATCA ACGGAAAACA CATCAGCATC AAAAACAACG GTGGTAATGC CGACTTAAAA    60
AACCTTAACG TCCATGCCAA AGCGGGGCA TTGAACATTC ATTCCGACCG GGCATTGAGC    120
ATAGAAAATA CCAAGCTGGA GTCTACCCAT AATACGCATC TTAATGCACA ACACGAGCGG    180
GTAACGCTCA ACCAAGTAGA TGCCTACGCA CACCGTCATC TAAGCATTAC CGGCAGCCAG    240
ATTTGGCAAA ACGACAAACT GCCTTCTGCC AACAAGCTGG TGGCTAACGG TGTATTGGCA    300
CTCAATGCGC GCTATTCCCA AATT                                          324
```

(2) INFORMATION FOR SEQ ID NO: 32:

(i) SEQUENCE CHARACTERISTICS:
        (A) LENGTH: 230 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 32:

```
AATTATGCAA AAAAACGCAA CGCCGAAAAA CTGGCACCGC GCGGATATTG TTGCTGCTTT    60
GAAAAAGAAA GGCTGGTCAC TTCGAGCACT TTCAATAGAA GCGGGGTTGT CGCCGAATAC    120
GCTTAGAAGC GCACTGGCCG CCCCTTATCT TAAGGGAGAA AGGATTATTG CCGCTGCAAT    180
CGGAGTGGAA CCGGAAGAGA TTTGGTCCGA ACGGTATGCA GATCGGAATT              230
```

(2) INFORMATION FOR SEQ ID NO: 33:

(i) SEQUENCE CHARACTERISTICS:
        (A) LENGTH: 249 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 33:

```
AATTTAATCG GTGGAATGCC TGTTCAACCG CACCAATCCC GCTGAATACG GTTGCTAATC    60
TAATATGTGA ATCAGGTTTA AGAAAAGTTT TAGATTTCCA ACCTTGTTGA CTGGGAAAGA    120
GCAAAGTTTT TTGTAATCGA GTATCGTGTG TCTGTGCCAT TGTCGAAATA GTCATACTTA    180
TATCGTTCTG TTTATCTTAT CAATATGAAA ACTACATCGT TGATTGCCCT GACAATGCCT    240
TGGTCAATT                                                           249
```

(2) INFORMATION FOR SEQ ID NO: 34:

(i) SEQUENCE CHARACTERISTICS:
        (A) LENGTH: 343 base pairs
        (B) TYPE: nucleotide

```
            (C) STRANDEDNESS: single
            (D) TOPOLOGY: linear (ii) MOLECULE TYPE: DNA (genomic)

(vi) ORIGINAL SOURCE:
             (A) ORGANISM: Neisseria meningitidis
             (B) STRAIN: Z2491

(xi) SEQUENCE DESCRIPTION: SEQ ID NO: 34:

AATTCTTGTC CCGGAGTCCA ACGTATATTT ACCCTCCTGC GAGCTAAAAG ACTATTATTC      60

TCCACTGCCA CAGTAGCCGC ATTCACCGCC GTATTCACAT CCCCTTTAAC CAATGCCACT     120

GCGCTGCCTG CGATAATCTG CGAGTAGGCT ATGACTTTTT GGCGTTCTTG GGGTGACAGT     180

TTGCCTACAT CGCGTCCGTC CAACAGGGTT TCTCCCACCA TCTCGCCGAC TGCCGCGCCG     240

ATTGCGCCGT CCCGACATTT GCCTTTATTT GCTACCGCCG ATGCACAGCC TGCTACGGCA     300

TGGGCTATCT TGTGGGCAAT GTAGTCTTCG CTGAGATTAA ATT                      343

(2) INFORMATION FOR SEQ ID NO: 35:

(i) SEQUENCE CHARACTERISTICS:
            (A) LENGTH: 184 base pairs
            (B) TYPE: nucleotide
            (C) STRANDEDNESS: single
            (D) TOPOLOGY: linear (ii) MOLECULE TYPE: DNA (genomic)

(vi) ORIGINAL SOURCE:
             (A) ORGANISM: Neisseria meningitidis
             (B) STRAIN: Z2491

(xi) SEQUENCE DESCRIPTION: SEQ ID NO: 35:

AATTCTTCAA ACATCGTTTC GATAATCGGG TCGGTGTACA CACTGATGCG GTCGCCCGCA      60

CGGCTTTGAC CGGCTCGGAA AATATAGGCG GTGGCTTTGC CGTCGGCGAT GTCGACGCAC     120

CAACGCCAGA TGGCGTCTTC GGTATTCAAA CAATCACCCG CACAGCTTTC ACCTGCGCGG     180

AATT                                                                 184

(2) INFORMATION FOR SEQ ID NO: 36:

(i) SEQUENCE CHARACTERISTICS:
            (A) LENGTH: 15620 base pairs
            (B) TYPE: nucleotide
            (C) STRANDEDNESS: single
            (D) TOPOLOGY: linear (ii) MOLECULE TYPE: DNA (genomic)

(vi) ORIGINAL SOURCE:
             (A) ORGANISM: Neisseria meningitidis
             (B) STRAIN: Z2491

(xi) SEQUENCE DESCRIPTION: SEQ ID NO: 36:

TATGCTCAAT CTCATTTTCA AAATGCAAAA CTTTTCTGAT TTTTCCTACT TTTTGCTCAA      60

TATTAGGAAG GTTTTAGGCA ATTGAAAATT TTTTGGCGCA TTTTTATGCG TCAAATTTCG     120

TTAACAGACT ATTTTTGCAA AGGTCTCCGT CTGTAAAAGC AAGGATAGGG CATCTGCCCT     180

TTTGATTGTT TGATTAACGA TACAAGGAGT TTCAAAATGA GAGTTTTATA GTGGATTAAC     240

AAAAACCAGT ACAGCGTTGC CTCGCCTTGC CGTACTATTT GTACTGTCTG CGGCTTCGTC     300

GCCTTGTCCT GATTTAAATT TAATCCACTA TATGTGTTCA TGAAATGACT TGGGTCGGAG     360

GCTCAGGTAA TGCGCAACAA AGTTCATATT ATTGCGAAAT TTGCGAATCT GCAGGGCTTA     420
```

```
ACGATACGGG AAATCCTGAT AAATCTTTAG GATTGCCAAA CAATACGTTC AGTAATCCGC      480

CTGGTTGGGG AGCTACAATC GGAGCTTTAG CAGGTAGCCG CATAGGTATG CCTGAATTTG      540

GTACGTTTGC GAGCCATGCC ATTGAAAATT TCGACTGGTC ATGGTATCGA CGTTATAGGG      600

AAATTGCCGA AACGATTGAA CGAGAATATT CAGGCGGTTT GCCTTAATAG TTGAGGAGGT      660

CATGATGTTT GCCAAACATT ATCAATTCAT CGCACTCGGC ATCATGCTGC TTCTTTATAT      720

GTTGATTCTC TATACGACCG ATTTTTCCAA TCTGACGTAT TGGATGCTGT TTTTTATCTG      780

TTTTATTACA GGAAAAATAT TAGCTCGTTT GTTAGAGAAA AGCTTTAAAT AAAATAGCAG      840

CTAGTCGCAA AAGGTCGTCT GAAACCTTTT CAGGCGGCCT TTCTAAAATA CATCCAACTT      900

CCTAATCCCT ATTTTTCAAA AAGGAAATCT ATGCCCCATC TGCAAAACCT GTCTTTGGGC      960

TTAAAGAAAA AGCTGCCTGT TATCCTGCAA ACAGAAATAT CAGAATGCGG CTTGGCATGT     1020

CTGGCGGCTG TGGCGGGATT TCATGGTTTC CATACGAATT TACGCGCACT GCGTTCAAAA     1080

TACTGTCCGA GACCTTTGCA AAATTCCCCA AAATCCCCTA AATGTCTTGG TGGGAATTTT     1140

GGGGAATTTT GCAAAGGTCT CATTCTATAA CTGTAAATAC TTTTAAATTT ATGACAAAAT     1200

AGTAAATATT GCTAAAATAA TATTGATGTC ATGAAATTTT TTCCTGCTCC ATGTCTGTTG     1260

GTTATCCTGG CTGTCATACC CCTTAAAACC TTAGCTGCCG ATGAAAACGA TGCAGAACTT     1320

ATCCGTTCCA TGCAGCGTCA GCAGCACATA GATGCTGAAT TGTTAACTGA TGCAAATGTC     1380

CGTTTCGAGC AACCATTGGA GAAGAACAAT TATGTCCTGA GTGAAGATGA ACACCGTGT      1440

ACTCGGGTAA ATTACATTAG TTTAGATGAT AAGACGGCGC GCAAATTTTC TTTTCTTCCT     1500

TCTGTGCTCA TGAAAGAAAC AGCTTTTAAA ACTGGGATGT GTTTAGGTTC CAATAATTTG     1560

AGCAGGCTAC AAAAAGCCGC GCAACAGATA CTGATTGTGC GTGGCTACCT CACTTCCCAA     1620

GCTATTATCC AACCACAGAA TATGGATTCG GGAATTCTGA AATTACGGGT ATCAGCAGGC     1680

GAAATAGGGG ATATCCGCTA TGAAGAAAAA CGGGATGGGA AGTCTGCCGA GGGCAGTATT     1740

AGTGCATTCA ATAACAAATT TCCCTTATAT AGGAACAAAA TTCTCAATCT TCGCGATGTA     1800

GAGCAGGGCT TGGAAAACCT GCGTCGTTTG CCGAGTGTTA AAACAGATAT TCAGATTATA     1860

CCGTCCGAAG AAGAAGGCAA AAGCGATTTA CAGATCAAAT GGCAGCAGAA TAAACCCATA     1920

CGGTTCAGTA TCGGTATAGA TGATGCGGGC GGCAAAACGA CCGGCAAATA TCAAGGAAAT     1980

GTCGCTTTAT CGTTCGATAA CCCTTTGGGC TTAAGCGATT TGTTTTATGT TTCATATGGA     2040

CGCGGTTTGG TGCACAAAAC GGACTTGACT GATGCCACCG GTACGGAAAC TGAAAGCGGA     2100

TCCAGAAGTT ACAGCGTGCA TTATTCGGTG CCCGTAAAAA AATGGCTGTT TTCTTTTAAT     2160

CACAATGGAC ATCGTTACCA CGAAGCAACC GAAGGCTATT CCGTCAATTA CGATTACAAC     2220

GGCAAACAAT ATCAGAGCAG CCTGGCCGCC GAGCGCATGC TTTGGCGTAA CAGGTTTCAT     2280

AAAACTTCAG TCGGAATGAA ATTATGGACA CGCCAAACCT ATAAATACAT CGACGATGCC     2340

GAAATCGAAG TGCAACGCCG CCGCTCTGCA GGCTGGGAAG CCGAATTGCG CCACCGTGCT     2400

TACCTCAACC GTTGGCAGCT TGACGGCAAG TTGTCTTACA AACGCGGGAC CGGCATGCGC     2460

CAAAGTATGC CCGCACCTGA AGAAAACGGC GGCGGTACTA TTCCAGGCAC ATCCCGTATG     2520

AAAATCATAA CCGCCGGATT GGATGCAGCG GCCCCGTTTA TGTTGGGCAA ACAGCAGTTT     2580

TTCTACGCAA CCGCCATTCA AGCTCAATGG AACAAAACGC CTTTGGTTGC CAAGACAAG     2640

TTGTCTATCG GCAGCCGCTA CACCGTTCGC GGATTTGATG GGAGCAGAG TCTTTTCGGA      2700

GAGCGAGGTT TCTACTGGCA GAATACTTTA ACTTGGTATT TTCATCCGAA CCATCAGTTC     2760

TATCTCGGTG CGGACTATGG CCGCGTATCT GGCGAAAGTG CACAATATGT ATCGGGCAAG     2820
```

```
CAGCTGATGG GTGCAGTGGT CGGCTTCAGA GGAGGGCATA AAGTAGGCGG TATGTTTGCT    2880
TATGATCTGT TTGCCGGCAA GCCGCTTCAT AAACCCAAAG GCTTTCAGAC GACCAACACC    2940
GTTTACGGCT TCAACTTGAA TTACAGTTTC TAACCTCTGA ATTTTTTTAC TGATATTTAG    3000
ACGGTCTTTC CTTATCCTCA GACTGTCAAA CTTTACCTAC GTACTTGGCG CGCAGTACGT    3060
TCATCTTCAA AATGGAATAG ACATGAATAA AGGTTTACAT CGCATTATCT TTAGTAAAAA    3120
GCACAGCACC ATGGTTGCAG TAGCCGAAAC TGCCAACAGC CAGGGCAAAG GTAAACAGGC    3180
AGGCAGTTCG GTTTCTGTTT CACTGAAAAC TTCAGGCGAC CTTTGCGGCA AACTCAAAAC    3240
CACCCTTAAA ACCTTGGTCT GCTCTTTGGT TTCCCTGAGT ATGGTATTGC CTGCCCATGC    3300
CCAAATTACC ACCGACAAAT CAGCACCTAA AAACCAGCAG GTCGTTATCC TTAAAACCAA    3360
CACTGGTGCC CCCTTGGTGA ATATCCAAAC TCCGAATGGA CGCGGATTGA GCCACAACCG    3420
CTATACGCAG TTTGATGTTG ACAACAAAGG GGCAGTGTTA ACAACGACC GTAACAATAA    3480
TCCGTTTCTG GTCAAAGGCA GTGCGCAATT GATTTTGAAC GAGGTACGCG GTACGGCTAG    3540
CAAACTCAAC GGCATCGTTA CCGTAGGCGG TCAAAAGGCC GACGTGATTA TTGCCAACCC    3600
CAACGGCATT ACCGTTAATG GCGGCGGCTT TAAAAATGTC GGTCGGGGCA TCTTAACTAT    3660
CGGTGCGCCC CAAATCGGCA AAGACGGTGC ACTGACAGGA TTTGATGTGC GTCAAGGCAC    3720
ATTGACCGTA GGAGCAGCAG GTTGGAATGA TAAAGGCGGA GCCGACTACA CCGGGGTACT    3780
TGCTCGTGCA GTTGCTTTGC AGGGGAAATT ACAGGGTAAA AACCTGGCGG TTTCTACCGG    3840
TCCTCAGAAA GTAGATTACG CCAGCGGCGA AATCAGTGCA GGTACGGCAG CGGGTACGAA    3900
ACCGACTATT GCCCTTGATA CTGCCGCACT GGGCGGTATG TACGCCGACA GCATCACACT    3960
GATTGCCAAT GAAAAAGGCG TAGGCGTCAA AAATGCCGGC ACACTCGAAG CGGCCAAGCA    4020
ATTGATTGTG ACTTCGTCAG GCCGCATTGA AAACAGCGGC CGCATCGCCA CCACTGCCGA    4080
CGGCACCGAA GCTTCACCGA CTTATCTCTC CATCGAAACC ACCGAAAAAG GAGCGGCAGG    4140
CACATTTATC TCCAATGGTG GTCGGATCGA GAGCAAAGGC TTATTGGTTA TTGAGACGGG    4200
AGAAGATATC AGCTTGCGTA ACGGAGCCGT GGTGCAGAAT AACGGCAGTC GCCCAGCTAC    4260
CACGGTATTA AATGCTGGTC ATAATTTGGT GATTGAGAGT AAAACTAATG TGAACAATGC    4320
CAAAGGCTCG GCTAATCTGT CGGCCGGCGG TCGTACTACG ATCAATGATG CTACTATTCA    4380
AGCGGGCAGT TCCGTGTACA GCTCCACCAA AGGCGATACT GAATTGGGTG AAAATACCCG    4440
TATTATTGCT GAAAACGTAA CCGTATTATC TAACGGTAGT ATTGGCAGTG CTGCTGTAAT    4500
TGAGGCTAAA GACACTGCAC ACATTGAATC GGGCAAACCG CTTTCTTTAG AAACCTCGAC    4560
CGTTGCCTCC AACATCCGTT TGAACAACGG TAACATTAAA GGCGGAAAGC AGCTTGCTTT    4620
ACTGGCAGAC GATAACATTA CTGCCAAAAC TACCAATCTG AATACTCCCG GCAATCTGTA    4680
TGTTCATACA GGTAAAGATC TGAATTTGAA TGTTGATAAA GATTTGTCTG CCGCCAGCAT    4740
CCATTTGAAA TCGGATAACG CTGCCCATAT TACCGGCACC AGTAAAACCC TCACTGCCTC    4800
AAAAGACATG GGTGTGGAGG CAGGCTTGCT GAATGTTACC AATACCAATC TGCGTACCAA    4860
CTCGGGTAAT CTGCACATTC AGGCAGCCAA AGGCAATATT CAGCTTCGCA ATACCAAGCT    4920
GAACGCAGCC AAGGCTCTCG AAACCACCGC ATTGCAGGGC AATATCGTTT CAGACGGCCT    4980
TCATGCTGTT TCTGCAGACG GTCATGTATC CTTATTGGCC AACGGTAATG CCGACTTTAC    5040
CGGTCACAAT ACCCTGACAG CCAAGGCCGA TGTCAATGCA GGATCGGTTG GTAAAGGCCG    5100
TCTGAAAGCA GACAATACCA ATATCACTTC ATCTTCAGGA GATATTACGT TGGTTGCCGG    5160
```

-continued

| | |
|---|---|
| CAACGGTATT CAGCTTGGTG ACGGAAAACA ACGCAATTCA ATCAACGAAA AACACATCAG | 5220 |
| CATCAAAAAC AACGGTGGTA ATGCCGACTT AAAAAACCTT AACGTCCATG CCAAAAGCGG | 5280 |
| GGCATTGAAC ATTCATTCCG ACCGGGCATT GAGCATAGAA AATACCAAGC TGGAGTCTAC | 5340 |
| CCATAATACG CATCTTAATG CACAACACGA GCGGGTAACG CTCAACCAAG TAGATGCCTA | 5400 |
| CGCACACCGT CATCTAAGCA TTACCGGCAG CCAGATTTGG CAAAACGACA AACTGCCTTC | 5460 |
| TGCCAACAAG CTGGTGGCTA ACGGTGTATT GGCACTCAAT GCGCGCTATT CCCAAATTGC | 5520 |
| CGACAACACC ACGCTGAGAG CGGGTGCAAT CAACCTTACT GCCGGTACCG CCCTAGTCAA | 5580 |
| GCGCGGCAAC ATCAATTGGA GTACCGTTTC GACCAAGACT TTGGAAGATA ATGCCGAATT | 5640 |
| AAAACCATTG GCCGGACGGC TGAATATTGA AGCAGGTAGC GGCACATTAA CCATCGAACC | 5700 |
| TGCCAACCGC ATCAGTGCGC ATACCGACCT GAGCATCAAA ACAGGCGGAA AATTGCTGTT | 5760 |
| GTCTGCAAAA GGAGGAAATG CAGGTGCGCC TAGTGCTCAA GTTTCCTCAT TGGAAGCAAA | 5820 |
| AGGCAATATC CGTCTGGTTA CAGGAGAAAC AGATTTAAGA GGTTCTAAAA TTACAGCCGG | 5880 |
| TAAAAACTTG GTTGTCGCCA CCACCAAAGG CAAGTTGAAT ATCGAAGCCG TAAACAACTC | 5940 |
| ATTCAGCAAT TATTTTCCTA CACAAAAAGC GGCTGAACTC AACCAAAAAT CCAAAGAATT | 6000 |
| GGAACAGCAG ATTGCGCAGT TGAAAAAAAG CTCGCCTAAA AGCAAGCTGA TTCCAACCCT | 6060 |
| GCAAGAAGAA CGCGACCGTC TCGCTTTCTA TATTCAAGCC ATCAACAAGG AAGTTAAAGG | 6120 |
| TAAAAAACCC AAAGGCAAAG AATACCTGCA AGCCAAGCTT TCTGCACAAA ATATTGACTT | 6180 |
| GATTTCCGCA CAAGGCATCG AAATCAGCGG TTCCGATATT ACCGCTTCCA AAAAACTGAA | 6240 |
| CCTTCACGCC GCAGGCGTAT TGCCAAAGGC AGCAGATTCA GAGGCGGCTG CTATTCTGAT | 6300 |
| TGACGGCATA ACCGACCAAT ATGAAATTGG CAAGCCCACC TACAAGAGTC ACTACGACAA | 6360 |
| AGCTGCTCTG AACAAGCCTT CACGTTTGAC CGGACGTACG GGGGTAAGTA TTCATGCAGC | 6420 |
| TGCGGCACTC GATGATGCAC GTATTATTAT CGGTGCATCC GAAATCAAAG CTCCCTCAGG | 6480 |
| CAGCATAGAC ATCAAAGCCC ATAGTGATAT TGTACTGGAG GCTGGACAAA ACGATGCCTA | 6540 |
| TACCTTCTTA AAAACCAAAG GTAAAAGCGG CAAAATCATC AGAAAAACCA AGTTTACCAG | 6600 |
| CACCCGCGAC CACCTGATTA TGCCAGCCCC CGTCGAGCTG ACCGCCAACG GTATCACGCT | 6660 |
| TCAGGCAGGC GGCAACATCG AAGCTAATAC CACCCGCTTC AATGCCCCTG CAGGTAAAGT | 6720 |
| TACCCTGGTT GCGGGTGAAG AGCTGCAACT GCTGGCAGAA GAAGGCATCC ACAAGCACGA | 6780 |
| GTTGGATGTC CAAAAAAGCC GCCGCTTTAT CGGCATCAAG GTAGGTAAGA GCAATTACAG | 6840 |
| TAAAAACGAA CTGAACGAAA CCAAATTGCC TGTCCGCGTC GTCGCCCAAA CTGCAGCCAC | 6900 |
| CCGTTCAGGC TGGGATACCG TGCTCGAAGG TACCGAATTC AAAACCACGC TGGCCGGTGC | 6960 |
| CGACATTCAG GCAGGTGTAG GCGAAAAAGC CCGTGTCGAT GCGAAAATTA TCCTCAAAGG | 7020 |
| CATTGTGAAC CGTATCCAGT CGGAAGAAAA ATTAGAAACC AACTCAACCG TATGGCAGAA | 7080 |
| ACAGGCCGGA CGCGGCAGCA CTATCGAAAC GCTAAAACTG CCCAGCTTCG AAAGCCCTAC | 7140 |
| TCCGCCCAAA TTGTCCGCAC CCGGCGGCTA TATCGTCGAC ATTCCGAAAG GCAATCTGAA | 7200 |
| AACCGAAATC GAAAAGCTGT CCAAACAGCC CGAGTATGCC TATCTGAAAC AGCTCCAAGT | 7260 |
| AGCGAAAAAC ATCAACTGGA ATCAGGTGCA GCTTGCTTAC GACAGATGGG ACTACAAACA | 7320 |
| GGAGGGCTTA ACCGAAGCAG GTGCGGCGAT TATCGCACTG GCCGTTACCG TGGTCACCTC | 7380 |
| AGGCGCAGGA ACCGGAGCCG TATTGGGATT AAACGGTGCG GCCGCCGCCG CAACCGATGC | 7440 |
| AGCATTCGCC TCTTTGGCCA GCCAGGCTTC CGTATCGTTC ATCAACAACA AAGGCGATGT | 7500 |
| CGGCAAAACC CTGAAAGAGC TGGGCAGAAG CAGCACGGTG AAAAATCTGG TGGTTGCCGC | 7560 |

-continued

```
CGCTACCGCA GGCGTAGCCG ACAAAATCGG CGCTTCGGCA CTGAACAATG TCAGCGATAA    7620
GCAGTGGATC AACAACCTGA CCGTCAACCT AGCCAATGCG GGCAGTGCCG CACTGATTAA    7680
TACCGCTGTC AACGGCGGCA GCCTGAAAGA CAATCTGGAA GCGAATATCC TTGCGGCTTT    7740
GGTCAATACC GCGCATGGAG AAGCAGCCAG TAAAATCAAA CAGTTGGATC AGCACTACAT    7800
AGTCCACAAG ATTGCCCATG CCATAGCGGG CTGTGCGGCA GCGGCGGCGA ATAAGGGCAA    7860
GTGTCAGGAT GGTGCGATAG GTGCGGCTGT GGGCGAGATA GTCGGGGAGG CTTTGACAAA    7920
CGGCAAAAAT CCTGACACTT TGACAGCTAA AGAACGCGAA CAGATTTTGG CATACAGCAA    7980
ACTGGTTGCC GGTACGGTAA GCGGTGTGGT CGGCGGCGAT GTAAATGCGG CGGCGAATGC    8040
GGCTGAGGTA GCGGTGAAAA ATAATCAGCT TAGCGACAAA GAGGGTAGAG AATTTGATAA    8100
CGAAATGACT GCATGCGCCA ACAGAATAA TCCTCAACTG TGCAGAAAAA ATACTGTAAA     8160
AAAGTATCAA AATGTTGCTG ATAAAAGACT TGCTGCTTCG ATTGCAATAT GTACGGATAT    8220
ATCCCGTAGT ACTGAATGTA GAACAATCAG AAAACAACAT TTGATCGATA GTAGAAGCCT    8280
TCATTCATCT TGGGAAGCAG GTCTAATTGG TAAAGATGAT GAATGGTATA AATTATTCAG    8340
CAAATCTTAC ACCCAAGCAG ATTTGGCTTT ACAGTCTTAT CATTTGAATA CTGCTGCTAA    8400
ATCTTGGCTT CAATCGGGCA ATACAAAGCC TTTATCCGAA TGGATGTCCG ACCAAGGTTA    8460
TACACTTATT TCAGGAGTTA ATCCTAGATT CATTCCAATA CCAAGAGGGT TTGTAAAACA    8520
AAATACACCT ATTACTAATG TCAAATACCC GGAAGGCATC AGTTTCGATA CAAACCTAAA    8580
AAGACATCTG GCAAATGCTG ATGGTTTTAG TCAAGAACAG GGCATTAAAG GAGCCCATAA    8640
CCGCACCAAT TTTATGGCAG AACTAAATTC ACGAGGAGGA CGCGTAAAAT CTGAAACCCA    8700
AACTGATATT GAAGGCATTA CCCGAATTAA ATATGAGATT CCTACACTAG ACAGGACAGG    8760
TAAACCTGAT GGTGGATTTA AGGAAATTTC AAGTATAAAA ACTGTTTATA ATCCTAAAAA    8820
ATTTTCTGAT GATAAAATAC TTCAAATGGC TCAAATGCT GCTTCACAAG GATATTCAAA     8880
AGCCTCTAAA ATTGCTCAAA ATGAAAGAAC TAAATCAATA TCGGAAAGAA AAAATGTCAT    8940
TCAATTCTCA GAAACCTTTG ACGGAATCAA ATTTAGATCA TATTTTGATG TAAATACAGG    9000
AAGAATTACA AACATTCACC CAGAATAATT TAAAGGAAAA ATTATGAAAA ATAATATTTT    9060
TCTAAACTTA AATAAAAAAT CTATAAATAA CAACCATTTT GTTATTTCGA TTTTTTTTGA    9120
AACAATTTAC CAATTTGAAA CTAAAGATAC GCTTTTAGAG TGTTTTAAAA ATATTACAAC    9180
TACCGGACAT TTTGGAGTAA TAGGTGCTCA ATATGAAAAA ATAGATGCTA CCAGATGGAT    9240
TGGAGATTAT GAAGAGGTAA ATGGATTTGA GTATATTGAT AAAGCTCCTT CTATTTATTT    9300
TTCAGTTGGA GATGATTTCA ATCCTGAAGA ATTAATTATA CCTATTAATT TAGCATATCA    9360
TTACTTTAAT ATTGCAATAT CTGATTTCTT AATAGCTCAC CCTGAATATC AAAAAAAGTG    9420
TAAAGAAATA CAAAAAACAT ATTCTCAAAC AAACTGTAGC CTGCATGAAA CCTAAAATCC    9480
ATGCGTAAGG TGTGTGCTTC AGCACGCACG CGTTCCATGA TTTACGGCTC AATGCCGTCT    9540
GAAAAGCTCA CAATTTTTCA GACGGCATTT GTTATGCAAG TAAATATTCA GATTCCCTAT    9600
ATACTGCCCA GACGCGTGCG TGCTGAAGAC ACCCCCTACG CTTGCTGCAG AACTTTCGGG    9660
TAAAACCGGT GTGAGCATTA GCGCACCGTA TGCCAATGAG AACAGTCGCA TCCTGCTCAG    9720
CACCACGGAT ATCAGTTCGG AAAACGGCAA AATCAAAATT CAATCTTACG GTGACCAATA    9780
TTACTATGCG AGACAGAGCG AACTCTATAC CTTTGAACGC CGCAGCTACA AAACTGGCAA    9840
ATGGTACAAC CGCAAACACA TTACCGAAGT CAAAGAACAC AAAAACGCCA AGCCCGACGC    9900
```

| | |
|---|---|
| AGTAAACCTC AGCGCATCCC AAGGCATCGA CATCAAATCT GGTGGCAGCA TCGACGCCTA | 9960 |
| CGCCACCGCA TTCGATGCCC CCAAAGGCAG CATTAACATC GAAGCCGGGC GGAAATTGAC | 10020 |
| ACTCTATGCC GTAGAAGAGC TCAACTACGA CAAACTAGAC AGCCAAAAAA GGCGCAGATT | 10080 |
| TCTCGGCATC AGCTACAGCA AAGCACACGA CACCACCACC CAAGTCATGA AAACCGCGCT | 10140 |
| GCCCTCAAGG GTAGTTGCAG AATCAGCCAA CCTCCAATCG GGCTGGGATA CCAAACTGCA | 10200 |
| AGGCACACAG TTTGAAACCA CACTGGGTGG CGCAACCATA CGCGCAGGCG TAGGTGAGCA | 10260 |
| GGCACGGGCA GATGCCAAGA TTATCCTCGA AGGGATCAAA AGCAGCATCC ACACAGAAAC | 10320 |
| CGTGAGCAGC AGCAAATCTA CTCTATGGCA AAAACAGGCA GGACGGGGCA GTAACATCGA | 10380 |
| AACCTTGCAA TTGCCGAGTT TCACCGGTCC CGTTGCGCCC GTACTGTCCG CACCCGGCGG | 10440 |
| TTACATTGTC GACATTCCGA AAGGCAATCT GAAAACCCAA ATCGAAACCC TCACCAAGCA | 10500 |
| GCCCGAGTAT GCTTATTTGA ACAACTTCA AGTTGCGAAA ACATCAACT GGAATCAGGT | 10560 |
| GCAGCTTGCT TACGATAAAT GGGACTACAA ACAGGAGGGC ATGACACCCG CAGCAGCAGC | 10620 |
| TGTCGTCGTT ATCGTCGTAA CCGTATTGAC CTACGGTGCA CTGTCCGCCC GGCAGCCGC | 10680 |
| CGGAACGGCG GGCGCGGCAG GCGCAGGAGC GGGAGGAGCC GCAGCAGGAA CGGCAGCCGG | 10740 |
| AACTGGAGTA GCAGCAGGAA CGGCAGCCAC AACCGGAGTA GCAGCAGGCA CATCAGCTGC | 10800 |
| AGCTATCACC ACAGCCGCAG GCAAAGCCGC ACTGGCCAGT CTCGCCAGCC AAGCCGCAGT | 10860 |
| TTCCCTCATC AACAACAAAG GAGACATAAA CCATACCCTG AAAGAACTGG GCAAAAGCAG | 10920 |
| CACCGTCAGA CAGGCCGCCA CCGCCGCCGT AACCGCAGGC GTACTGCAGG GCATAAGCGG | 10980 |
| GCTGAACACC CAAGCAGCCG AAGCCGTCAG CAAACATTTT CACAGTCCCG CAGCAGGCAA | 11040 |
| ACTGACCGCT AACCTGATCA ACAGCACCGC TGCCGCAAGT GTCCATACCG CCATCAACGG | 11100 |
| CGGCAGCCTG AAAGACAACT TGGGCGATGC CGCACTGGGT GCGATAGTCA GTACCGTACA | 11160 |
| CGGAGAAGTA GCGAGCAAAA TCAAATTTAA TCTCAGCGAA GACTACATTG CCCACAAGAT | 11220 |
| AGCCCATGCC GTAGCAGGCT GTGCATCGGC GGTAGCAAAT AAAGGCAAAT GTCGGGACGG | 11280 |
| CGCAATCGGC GCGGCAGTCG GCGAGATGGT GGGAGAAACC CTGTTGGACG GACGCGATGT | 11340 |
| AGGCAAACTG TCACCCCAAG AACGCCAAAA AGTCATAGCC TACTCGCAGA TTATCGCAGG | 11400 |
| CAGCGCAGTG GCATTGGTTA AAGGGGATGT GAATACGGCG GTGAATGCGG CTACTGTGGC | 11460 |
| AGTGGAGAAT AATAGTCTTT TAGCTCGCAG GAGGGTAAAT ATACGTTGGA CTCCGCGACA | 11520 |
| AGAATTGGAA CATGAATATG CCATTCTTGA AATCCAGGCC ATTACCAATC AAATCCGAAG | 11580 |
| GCTGGATCCG AAATTTAACG GGATTGCTAT TCTGAGGACT CCTGGAGAGC CGTGGACAAG | 11640 |
| ACATGATGTA CAAACATACA GGCAATATTA TAATCAATTA AGGGAATCCA GAGGCTTTGC | 11700 |
| TGTTGAACCA ATTTATAGAA TCAGGATAAA CAACGGCAAT GAATTTAACC GTATCATGTC | 11760 |
| ATCAAAATAC CCTTATAATG AGCTTTATGT AGCCAATCCT AAATCGGCGA CGGGGTATTT | 11820 |
| TAGGGTAGAT TCGTATGATC CTGCGACAAG GGAAATTATT TCAAGAAAAT TTACCCAATT | 11880 |
| TTCTCAAATC CAAGAAAGTA CGGGGATTGG TTATATCAAG GAGGCTGTTA GAAAATATAG | 11940 |
| CCCTGGTACT GTCATTTCCA ATGTTCCAAG TACACCTACT ACGATAAGAG GAAGAAAGCT | 12000 |
| TGAAGGAAAA CTTATTTTAG AAGTTCCTGC TCAGGTCAAT CCAATTCCAC AATCTGTATT | 12060 |
| AAGGGCGGCA CAAGAAGAAA ATGTTATCAT TAGAGATACA ACAGGAAGGA TTTACAAATG | 12120 |
| AAGAAAGATA TTTTTTATTG TGAGCAGTGG TCTTATGGTT ATAAGAGACT TCATAAGCCT | 12180 |
| TTTTCTGAGA AACAAGCTGA GGAAAAACAT CTTAAAGGGG AGTTATATAC TGCCGTAATA | 12240 |
| GGTTCGGCGA CACAACCTGA ATATGTAATT ACCTTGCGAG AGGAAGTAGG TTTTTTTTCG | 12300 |

```
GTAAATTTTT TCGATAAATT TGGAAGGGAT TATTTAACCC ATCAATTTCA AAAATATTCC    12360

AATTCGAATT ATTATTTTCT TTCTATGGCT GTATGGAGAG ATTATATAAC TTTGGAATCT    12420

CATGACTTAG CAGAAGGATA TACTTATTTC TTCAATGAAA ATACGGATGA TTGCTATGTT    12480

TTGAAACAAG ATTTTATTAA TAATGAGCGA TATGAAAAAA CAGAATTATA TTCCCAAAAA    12540

GATAAGGTAA TTCTATTTCC AAAGTTTGGT GAATATGATT TGGTGTTAAA TCCGACATT     12600

ATTTAATTAA GTTTTAAGGC CGTCTGAAAA AAATTTCAAA CGGCTTTTAT TATTGGGTTT    12660

GGAATCTGAG GATAAAGCTG ATAAAAACCA GGAAATTATC AGATTGCTAT ATACGTATTG    12720

TTGTACAGAC TAAAGGCAGC AATCAAATCA CTATTGCTTA CCCACAAAAA TAAATTGATT    12780

ATATGGAATA ATCATGAATA AGAGAATGAA AATGTGTCCT GCTTGTCAAC AAGGCTATCT    12840

CTACCATTCG AAACCTAAAT ATCTTCATGA TGAAATTATT CTGTGTGATG AATGCGATGC    12900

AGTATGGCTC AAAGGTATGA ATATATTTTA TGGAGAATAT GAAAAGATT TTTATTCTTA     12960

TGTTCCTTTC ATGGAATCCC AAGGTATAAC GAGTGAATGT ATTTGGGAAG GAGATTTGTT    13020

TGATCATCCA TATTATGAAG ATGAAAACTC AAATGATATG GATTGATGGA AATTTTAAGC    13080

CTGCGTAGGT ACGATTAGCC ATCAAACGGC GTAATCATAC GCAAGATTAT CAACAGAGAG    13140

GGCTGGCAGC GATATACCAC CCACAAGATT GCCCATGCCA TAGCGGGCTG TGCGGCAGCG    13200

GCGGCGAATA AGGGCAAGTG TCAGGATGGT GCGATAGGCG CTGCAGTCGG TGAGATTGTT    13260

GGTGAGGCTT TGGTTAAGAA TACTGATTTC AGTCGTATGA GTGCGACCGA AATCGAAAAA    13320

GCTAAAGCGA AGATTACTGC CTATTCAAAA CTGGTTGCCG GCACTGCGTC TGCCGTTGTA    13380

GGCGGGGATG TGAATACAGC GGCGAATGCG GCACAGATAG CGGTGGAGAA TAATACTTTG    13440

TATCCTAGAT GCGTTGGTGC AAAGTGTGAT GAATTTCAAA AGGAACAACA AAAATGGATA    13500

CGTGAAAATC CTGAAGAATA TCGAGAAGTT TTGCTTTTTC AGACAGGATT TATTCCAATT    13560

ATCGGTGATA TACAGAGTTT TGTACAAGCA CAGACCGCTG CCGATCACCT GTTTGCTTTG    13620

CTGGGTGTGG TTCCGGGTAT CGGTGAATCG ATACAGGCCT ATAAAGTAGC GAAAGCGGCA    13680

AAAAATTTAC AAGGCATGAA AAAAGCCTTG GACAAGGCAG CAACCGTTGC CACTGCACAG    13740

GGCTATGTCA GCAAAACCAA AATCAAAATC GGTCAAACTG AATTAAGGGT TACTGCAGCA    13800

ACTGACAAAC AATTGCTGAA AGCTATTGGC GAAGGAAGGG ACACGACAGG TAAAATGACC    13860

GAGCAGTTAT TTGACTCTTT AGCTAAACAA AATGGCTTCA GAGTGCTTTC GGGCGGCAAA    13920

TACGGCGGAA ATAACGGTTT TGATCATGTA TGGCAGGCTG CCGATGGTAG TGTCGTTTTG    13980

ATTGTAGAAA GTAAGCAGAT TAGGAACGGT ACGGTACAGC TGAATCCGAA TGGTGCGGGT    14040

GGATATACGC AAATGAGTGA GGATTGGATT AGACAAGTTT TAGATCAATT ACCCGATGGT    14100

AGTCCCGCTA AAGCTGCTGT CTTCAAAGCA AATAAGAACG GCACATTAAA AACAGCAATA    14160

GCAGGCGTTG ATCGTCAAAC AGGTAAGGCC GTTATTCTTC CTGTCAAAGT TCCTTCTAAA    14220

ACCAATATAA GGAGATAACA ATGGGCACA ATATGATGAC CACCCAAAAA TGGTATGAGC      14280

ATATTACTAA TGTAATCATA GGCAATACTG CTAATTTCAA TAGCGGTTGC CTTGACTCTA    14340

TAGATTATGT AGATGAAAGA AAAGGCGTTC CGCTTGCAGC TATGCAACAT ATTTTCATGG    14400

ACGTTAGAGC TGCAGCTTCC CATGCCTATC TATTTGAACA TGATCTTAAG AAATTCAAGC    14460

AATATGCTTA TGTTGCAGGA AAGCTGGGGG TTTTGCTGAG TGTAAATTCT ACAGACCCTG    14520

AACCCTTCTT CTTTCCCTGT GACATGCTCA ACATTCAAAA TCCGATGTTT CTGATGCTGA    14580

TGAGCGACAG CCCACAGCTG CGTGAGTTTC TGGTGCGCAA TATCGACAAC ATCGCCAACG    14640
```

```
ATACAGAAGC CTTTATAAAC CGCTACGACC TCAACCGGCA TATGATTTAC AATACTCTGC  14700

TGATGGTGGA GGGTAAGCAG CTTGATCGGT TGAAACAACG TAGCGAGAAA GTCTTGGCGC  14760

ATCCCACCCC TAGCAAATGG CTGCAAAAGC GGTTGTACGA TTACCGCTTC TTCCTCGCTT  14820

TCGCCGAACA GGATGCCGAG GCAATGAAAG CCGCCTTAGA GCCGCTTTTC GATAAAAAAA  14880

CCGCGCGTAT GGCTGCCAAA GAAACATTGT CCTATTTCGA TTTCTACCTG CAGCCGCAAA  14940

TCGTTACCTA CGCCAAAATC GCATCCATGC ACGGTTTCGA TTTGGGCATA GATCAAGAAA  15000

TCTCACCGAG GGATTTGATT GTTTACGATC CGCTGCCGGC AGACGAATAT CAAGACATCT  15060

TCGATTTTAT GAAACAGTAT GACTTGTCTT ACCCGTATGA ATATCTGCAG GATTGGATAG  15120

ATTACTATAC GTTCAAAACC GATAAGCTGG TATTTGGTAA CGCGAAGCGA GAGTGAGCCG  15180

TAAAACTCTG AGCTCCTGTT TTATAGATTA CAACTTTAGG CCGTCTTAAA GCTGAAAGAT  15240

TTTCGAAAGC TATAAATTGA AGCCCTTCCA CAGTACATAG ATCTGTGTTG TGGCGGGGCT  15300

TTACCACGCT GATTGCCGGA GAAGAACTCA ACCTGCTGGC AAAACAAGGC ATGAGATCTT  15360

TGCAATAACA TGAGTTGAGA CCTTTGCAAA AAAGCCCTTC CCCGACATCC GAAACCCAAA  15420

CACAGGATTT CGGCTGTTTT CGTACCAAAT ACCTCCTAAT TTTACCCAAA TACCCCCTTA  15480

ATCCTCCTCG GACACCCGAT AATCAGGCAT CCGGGCTGCC TTTTAGGCGG CAGCGGGCGC  15540

ATTTAGCCTG TTGGCCGCTT TCAACAGGTT CAAACACATC GCCTTCAGGT GGCTTTGCGC  15600

ACTCACTTTG TCATTTCCAA                                              15620
```

(2) INFORMATION FOR SEQ ID NO: 37:

(i) SEQUENCE CHARACTERISTICS:
        (A) LENGTH: 580 acides amin,s
        (B) TYPE: acide amin,
        (C) STRANDEDNESS: single
        (D) TOPOLOGY: linear (ii) MOLECULE TYPE: peptide (ix) FEATURE:
        (A) NAME/KEY: Protein
        (B) LOCATION:1..580

(xi) SEQUENCE DESCRIPTION: SEQ ID NO: 37:

```
Met Lys Phe Phe Pro Ala Pro Cys Leu Leu Val Ile Leu Ala Val Ile
1               5                   10                  15

Pro Leu Lys Thr Leu Ala Ala Asp Glu Asn Asp Ala Glu Leu Ile Arg
            20                  25                  30

Ser Met Gln Arg Gln His Ile Asp Ala Glu Leu Leu Thr Asp Ala
        35                  40                  45

Asn Val Arg Phe Glu Gln Pro Leu Glu Lys Asn Asn Tyr Val Leu Ser
    50                  55                  60

Glu Asp Glu Thr Pro Cys Thr Arg Val Asn Tyr Ile Ser Leu Asp Asp
65                  70                  75                  80

Lys Thr Ala Arg Lys Phe Ser Phe Leu Pro Ser Val Leu Met Lys Glu
                85                  90                  95

Thr Ala Phe Lys Thr Gly Met Cys Leu Gly Ser Asn Asn Leu Ser Arg
            100                 105                 110

Leu Gln Lys Ala Ala Gln Gln Ile Leu Ile Val Arg Gly Tyr Leu Thr
        115                 120                 125

Ser Gln Ala Ile Ile Gln Pro Gln Asn Met Asp Ser Gly Ile Leu Lys
    130                 135                 140

Leu Arg Val Ser Ala Gly Glu Ile Gly Asp Ile Arg Tyr Glu Glu Lys
```

-continued

```
           145                 150                 155                 160
      Arg Asp Gly Lys Ser Ala Glu Gly Ser Ile Ser Ala Phe Asn Asn Lys
                       165                 170                 175
      Phe Pro Leu Tyr Arg Asn Lys Ile Leu Asn Leu Arg Asp Val Glu Gln
                       180                 185                 190
      Gly Leu Glu Asn Leu Arg Arg Leu Pro Ser Val Lys Thr Asp Ile Gln
                       195                 200                 205
      Ile Ile Pro Ser Glu Glu Gly Lys Ser Asp Leu Gln Ile Lys Trp
                210                 215                 220
      Gln Gln Asn Lys Pro Ile Arg Phe Ser Gly Ile Asp Asp Ala Gly
      225                 230                 235                 240
      Gly Lys Thr Thr Gly Lys Tyr Gln Gly Asn Val Ala Leu Ser Phe Asp
                       245                 250                 255
      Asn Pro Leu Gly Leu Ser Asp Leu Phe Tyr Val Ser Tyr Gly Arg Gly
                       260                 265                 270
      Leu Val His Lys Thr Asp Leu Thr Asp Ala Thr Gly Thr Glu Thr Glu
                       275                 280                 285
      Ser Gly Ser Arg Ser Tyr Ser Val His Tyr Ser Val Pro Val Lys Lys
                290                 295                 300
      Trp Leu Phe Ser Phe Asn His Asn Gly His Arg Tyr His Glu Ala Thr
      305                 310                 315                 320
      Glu Gly Tyr Ser Val Asn Tyr Asp Tyr Asn Gly Lys Gln Tyr Gln Ser
                       325                 330                 335
      Ser Leu Ala Ala Glu Arg Met Leu Trp Arg Asn Arg Phe His Lys Thr
                       340                 345                 350
      Ser Val Gly Met Lys Leu Trp Thr Arg Gln Thr Tyr Lys Tyr Ile Asp
                       355                 360                 365
      Asp Ala Glu Ile Glu Val Gln Arg Arg Arg Ser Ala Gly Trp Glu Ala
                370                 375                 380
      Glu Leu Arg His Arg Ala Tyr Leu Asn Arg Trp Gln Leu Asp Gly Lys
      385                 390                 395                 400
      Leu Ser Tyr Lys Arg Gly Thr Gly Met Arg Gln Ser Met Pro Ala Pro
                       405                 410                 415
      Glu Glu Asn Gly Gly Gly Thr Ile Pro Gly Thr Ser Arg Met Lys Ile
                       420                 425                 430
      Ile Thr Ala Gly Leu Asp Ala Ala Pro Phe Met Leu Gly Lys Gln
                       435                 440                 445
      Gln Phe Phe Tyr Ala Thr Ala Ile Gln Ala Gln Trp Asn Lys Thr Pro
                       450                 455                 460
      Leu Val Ala Gln Asp Lys Leu Ser Ile Gly Ser Arg Tyr Thr Val Arg
      465                 470                 475                 480
      Gly Phe Asp Gly Glu Gln Ser Leu Phe Gly Glu Arg Gly Phe Tyr Trp
                       485                 490                 495
      Gln Asn Thr Leu Thr Trp Tyr Phe His Pro Asn His Gln Phe Tyr Leu
                       500                 505                 510
      Gly Ala Asp Tyr Gly Arg Val Ser Gly Glu Ser Ala Gln Tyr Val Ser
                       515                 520                 525
      Gly Lys Gln Leu Met Gly Ala Val Gly Phe Arg Gly His Lys
                530                 535                 540
      Val Gly Gly Met Phe Ala Tyr Asp Leu Phe Ala Gly Lys Pro Leu His
      545                 550                 555                 560
      Lys Pro Lys Gly Phe Gln Thr Asn Thr Val Tyr Gly Phe Asn Leu
                       565                 570                 575
```

```
Asn Tyr Ser Phe
        580

(2) INFORMATION FOR SEQ ID NO: 38:

(i) SEQUENCE CHARACTERISTICS:
        (A) LENGTH: 1981 acides amin,s
        (B) TYPE: acide amin,
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..1981

(xi) SEQUENCE DESCRIPTION: SEQ ID NO: 38:

Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
            20                  25                  30

Ala Gly Ser Ser Val Ser Val Ser Leu Lys Thr Ser Gly Asp Leu Cys
        35                  40                  45

Gly Lys Leu Lys Thr Thr Leu Lys Thr Leu Val Cys Ser Leu Val Ser
50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Asn Glu Lys Gly Val Gly Val Lys Asn
    290                 295                 300

Ala Gly Thr Leu Glu Ala Ala Lys Gln Leu Ile Val Thr Ser Ser Gly
```

-continued

```
            305                 310                 315                 320
        Arg Ile Glu Asn Ser Gly Arg Ile Ala Thr Thr Ala Asp Gly Thr Glu
                        325                 330                 335

Ala Ser Pro Thr Tyr Leu Ser Ile Glu Thr Thr Glu Lys Gly Ala Ala
                    340                 345                 350

Gly Thr Phe Ile Ser Asn Gly Gly Arg Ile Glu Ser Lys Gly Leu Leu
                    355                 360                 365

Val Ile Glu Thr Gly Glu Asp Ile Ser Leu Arg Asn Gly Ala Val Val
                370                 375                 380

Gln Asn Asn Gly Ser Arg Pro Ala Thr Thr Val Leu Asn Ala Gly His
        385                 390                 395                 400

Asn Leu Val Ile Glu Ser Lys Thr Asn Val Asn Asn Ala Lys Gly Ser
                        405                 410                 415

Ala Asn Leu Ser Ala Gly Gly Arg Thr Thr Ile Asn Asp Ala Thr Ile
                    420                 425                 430

Gln Ala Gly Ser Ser Val Tyr Ser Ser Thr Lys Gly Asp Thr Glu Leu
                    435                 440                 445

Gly Glu Asn Thr Arg Ile Ile Ala Glu Asn Val Thr Val Leu Ser Asn
                450                 455                 460

Gly Ser Ile Gly Ser Ala Ala Val Ile Glu Ala Lys Asp Thr Ala His
        465                 470                 475                 480

Ile Glu Ser Gly Lys Pro Leu Ser Leu Glu Thr Ser Thr Val Ala Ser
                        485                 490                 495

Asn Ile Arg Leu Asn Asn Gly Asn Ile Lys Gly Gly Lys Gln Leu Ala
                    500                 505                 510

Leu Leu Ala Asp Asp Asn Ile Thr Ala Lys Thr Thr Asn Leu Asn Thr
                515                 520                 525

Pro Gly Asn Leu Tyr Val His Thr Gly Lys Asp Leu Asn Leu Asn Val
                530                 535                 540

Asp Lys Asp Leu Ser Ala Ala Ser Ile His Leu Lys Ser Asp Asn Ala
        545                 550                 555                 560

Ala His Ile Thr Gly Thr Ser Lys Thr Leu Thr Ala Ser Lys Asp Met
                        565                 570                 575

Gly Val Glu Ala Gly Leu Leu Asn Val Thr Asn Thr Asn Leu Arg Thr
                    580                 585                 590

Asn Ser Gly Asn Leu His Ile Gln Ala Ala Lys Gly Asn Ile Gln Leu
                    595                 600                 605

Arg Asn Thr Lys Leu Asn Ala Ala Lys Ala Leu Glu Thr Thr Ala Leu
                610                 615                 620

Gln Gly Asn Ile Val Ser Asp Gly Leu His Ala Val Ser Ala Asp Gly
        625                 630                 635                 640

His Val Ser Leu Leu Ala Asn Gly Asn Ala Asp Phe Thr Gly His Asn
                        645                 650                 655

Thr Leu Thr Ala Lys Ala Asp Val Asn Ala Gly Ser Val Gly Lys Gly
                    660                 665                 670

Arg Leu Lys Ala Asp Asn Thr Asn Ile Thr Ser Ser Gly Asp Ile
                675                 680                 685

Thr Leu Val Ala Gly Asn Gly Ile Gln Leu Gly Asp Gly Lys Gln Arg
                690                 695                 700

Asn Ser Ile Asn Gly Lys His Ile Ser Ile Lys Asn Asn Gly Gly Asn
        705                 710                 715                 720

Ala Asp Leu Lys Asn Leu Asn Val His Ala Lys Ser Gly Ala Leu Asn
                        725                 730                 735
```

```
Ile His Ser Asp Arg Ala Leu Ser Ile Glu Asn Thr Lys Leu Glu Ser
            740                 745                 750

Thr His Asn Thr His Leu Asn Ala Gln His Glu Arg Val Thr Leu Asn
        755                 760                 765

Gln Val Asp Ala Tyr Ala His Arg His Leu Ser Ile Thr Gly Ser Gln
    770                 775                 780

Ile Trp Gln Asn Asp Lys Leu Pro Ser Ala Asn Lys Leu Val Ala Asn
785                 790                 795                 800

Gly Val Leu Ala Leu Asn Ala Arg Tyr Ser Gln Ile Ala Asp Asn Thr
                805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
        835                 840                 845

Asp Asn Ala Glu Leu Lys Pro Leu Ala Gly Arg Leu Asn Ile Glu Ala
    850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Leu Ser Ala Lys
                885                 890                 895

Gly Gly Asn Ala Gly Ala Pro Ser Ala Gln Val Ser Ser Leu Glu Ala
            900                 905                 910

Lys Gly Asn Ile Arg Leu Val Thr Gly Glu Thr Asp Leu Arg Gly Ser
        915                 920                 925

Lys Ile Thr Ala Gly Lys Asn Leu Val Val Ala Thr Thr Lys Gly Lys
    930                 935                 940

Leu Asn Ile Glu Ala Val Asn Asn Ser Phe Ser Asn Tyr Phe Pro Thr
945                 950                 955                 960

Gln Lys Ala Ala Glu Leu Asn Gln Lys Ser Lys Glu Leu Glu Gln Gln
                965                 970                 975

Ile Ala Gln Leu Lys Lys Ser Ser Pro Lys Ser Lys Leu Ile Pro Thr
            980                 985                 990

Leu Gln Glu Glu Arg Asp Arg Leu Ala Phe Tyr Ile Gln Ala Ile Asn
        995                 1000                1005

Lys Glu Val Lys Gly Lys Lys Pro Lys Gly Lys Glu Tyr Leu Gln Ala
    1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
                1045                1050                1055

Ala Gly Val Leu Pro Lys Ala Ala Asp Ser Glu Ala Ala Ile Leu
            1060                1065                1070

Ile Asp Gly Ile Thr Asp Gln Tyr Glu Ile Gly Lys Pro Thr Tyr Lys
        1075                1080                1085

Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
                1125                1130                1135

Ile Lys Ala His Ser Asp Ile Val Leu Glu Ala Gly Gln Asn Asp Ala
            1140                1145                1150
```

-continued

```
Tyr Thr Phe Leu Lys Thr Lys Gly Lys Ser Gly Lys Ile Ile Arg Lys
        1155                1160                1165

Thr Lys Phe Thr Ser Thr Arg Asp His Leu Ile Met Pro Ala Pro Val
        1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
        1205                1210                1215

Ala Gly Glu Glu Leu Gln Leu Leu Ala Glu Gly Ile His Lys His
        1220                1225                1230

Glu Leu Asp Val Gln Lys Ser Arg Arg Phe Ile Gly Ile Lys Val Gly
        1235                1240                1245

Lys Ser Asn Tyr Ser Lys Asn Glu Leu Asn Glu Thr Lys Leu Pro Val
        1250                1255                1260

Arg Val Val Ala Gln Thr Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
        1285                1290                1295

Ala Gly Val Gly Glu Lys Ala Arg Val Asp Ala Lys Ile Ile Leu Lys
        1300                1305                1310

Gly Ile Val Asn Arg Ile Gln Ser Glu Glu Lys Leu Glu Thr Asn Ser
        1315                1320                1325

Thr Val Trp Gln Lys Gln Ala Gly Arg Gly Ser Thr Ile Glu Thr Leu
        1330                1335                1340

Lys Leu Pro Ser Phe Glu Ser Pro Thr Pro Lys Leu Ser Ala Pro
1345                1350                1355                1360

Gly Gly Tyr Ile Val Asp Ile Pro Lys Gly Asn Leu Lys Thr Glu Ile
        1365                1370                1375

Glu Lys Leu Ser Lys Gln Pro Glu Tyr Ala Tyr Leu Lys Gln Leu Gln
        1380                1385                1390

Val Ala Lys Asn Ile Asn Trp Asn Gln Val Gln Leu Ala Tyr Asp Arg
        1395                1400                1405

Trp Asp Tyr Lys Gln Glu Gly Leu Thr Glu Ala Gly Ala Ala Ile Ile
        1410                1415                1420

Ala Leu Ala Val Thr Val Val Thr Ser Gly Ala Gly Thr Gly Ala Val
1425                1430                1435                1440

Leu Gly Leu Asn Gly Ala Ala Ala Ala Thr Asp Ala Ala Phe Ala
        1445                1450                1455

Ser Leu Ala Ser Gln Ala Ser Val Ser Phe Ile Asn Asn Lys Gly Asp
        1460                1465                1470

Val Gly Lys Thr Leu Lys Glu Leu Gly Arg Ser Ser Thr Val Lys Asn
        1475                1480                1485

Leu Val Val Ala Ala Thr Ala Gly Val Ala Asp Lys Ile Gly Ala
        1490                1495                1500

Ser Ala Leu Asn Asn Val Ser Asp Lys Gln Trp Ile Asn Asn Leu Thr
1505                1510                1515                1520

Val Asn Leu Ala Asn Ala Gly Ser Ala Ala Leu Ile Asn Thr Ala Val
        1525                1530                1535

Asn Gly Gly Ser Leu Lys Asp Asn Leu Glu Ala Asn Ile Leu Ala Ala
        1540                1545                1550

Leu Val Asn Thr Ala His Gly Glu Ala Ala Ser Lys Ile Lys Gln Leu
        1555                1560                1565

Asp Gln His Tyr Ile Val His Lys Ile Ala His Ala Ile Ala Gly Cys
```

```
          1570              1575              1580
Ala Ala Ala Ala Ala Asn Lys Gly Lys Cys Gln Asp Gly Ala Ile Gly
1585              1590              1595              1600

Ala Ala Val Gly Glu Ile Val Gly Glu Ala Leu Thr Asn Gly Lys Asn
              1605              1610              1615

Pro Asp Thr Leu Thr Ala Lys Glu Arg Glu Gln Ile Leu Ala Tyr Ser
              1620              1625              1630

Lys Leu Val Ala Gly Thr Val Ser Gly Val Val Gly Asp Val Asn
              1635              1640              1645

Ala Ala Ala Asn Ala Ala Glu Val Ala Val Lys Asn Asn Gln Leu Ser
1650              1655              1660

Asp Lys Glu Gly Arg Glu Phe Asp Asn Glu Met Thr Ala Cys Ala Lys
1665              1670              1675              1680

Gln Asn Asn Pro Gln Leu Cys Arg Lys Asn Thr Val Lys Lys Tyr Gln
              1685              1690              1695

Asn Val Ala Asp Lys Arg Leu Ala Ala Ser Ile Ala Ile Cys Thr Asp
              1700              1705              1710

Ile Ser Arg Ser Thr Glu Cys Arg Thr Ile Arg Lys Gln His Leu Ile
              1715              1720              1725

Asp Ser Arg Ser Leu His Ser Ser Trp Glu Ala Gly Leu Ile Gly Lys
              1730              1735              1740

Asp Asp Glu Trp Tyr Lys Leu Phe Ser Lys Ser Tyr Thr Gln Ala Asp
1745              1750              1755              1760

Leu Ala Leu Gln Ser Tyr His Leu Asn Thr Ala Ala Lys Ser Trp Leu
              1765              1770              1775

Gln Ser Gly Asn Thr Lys Pro Leu Ser Glu Trp Met Ser Asp Gln Gly
              1780              1785              1790

Tyr Thr Leu Ile Ser Gly Val Asn Pro Arg Phe Ile Pro Ile Pro Arg
              1795              1800              1805

Gly Phe Val Lys Gln Asn Thr Pro Ile Thr Asn Val Lys Tyr Pro Glu
              1810              1815              1820

Gly Ile Ser Phe Asp Thr Asn Leu Lys Arg His Leu Ala Asn Ala Asp
1825              1830              1835              1840

Gly Phe Ser Gln Glu Gln Gly Ile Lys Gly Ala His Asn Arg Thr Asn
              1845              1850              1855

Phe Met Ala Glu Leu Asn Ser Arg Gly Gly Arg Val Lys Ser Glu Thr
              1860              1865              1870

Gln Thr Asp Ile Glu Gly Ile Thr Arg Ile Lys Tyr Glu Ile Pro Thr
              1875              1880              1885

Leu Asp Arg Thr Gly Lys Pro Asp Gly Gly Phe Lys Glu Ile Ser Ser
              1890              1895              1900

Ile Lys Thr Val Tyr Asn Pro Lys Lys Phe Ser Asp Lys Ile Leu
1905              1910              1915              1920

Gln Met Ala Gln Asn Ala Ala Ser Gln Gly Tyr Ser Lys Ala Ser Lys
              1925              1930              1935

Ile Ala Gln Asn Glu Arg Thr Lys Ser Ile Ser Glu Arg Lys Asn Val
              1940              1945              1950

Ile Gln Phe Ser Glu Thr Phe Asp Gly Ile Lys Phe Arg Ser Tyr Phe
              1955              1960              1965

Asp Val Asn Thr Gly Arg Ile Thr Asn Ile His Pro Glu
              1970              1975              1980

(2) INFORMATION FOR SEQ ID NO: 39:
```

(i) SEQUENCE CHARACTERISTICS:
    (A) LENGTH: 143 acides amin,s
    (B) TYPE: acide amin,
    (C) STRANDEDNESS: single
    (D) TOPOLOGY: linear (ii) MOLECULE TYPE: peptide (ix) FEATURE:
    (A) NAME/KEY: Peptide
    (B) LOCATION:1..143

(xi) SEQUENCE DESCRIPTION: SEQ ID NO: 39:

```
Met Lys Asn Asn Ile Phe Leu Asn Leu Asn Lys Lys Ser Ile Asn Asn
1               5                   10                  15

Asn His Phe Val Ile Ser Ile Phe Phe Glu Thr Ile Tyr Gln Phe Glu
            20                  25                  30

Thr Lys Asp Thr Leu Leu Glu Cys Phe Lys Asn Ile Thr Thr Thr Gly
            35                  40                  45

His Phe Gly Val Ile Gly Ala Gln Tyr Glu Lys Ile Asp Ala Thr Arg
    50                  55                  60

Trp Ile Gly Asp Tyr Glu Glu Val Asn Gly Phe Glu Tyr Ile Asp Lys
65                  70                  75                  80

Ala Pro Ser Ile Tyr Phe Ser Val Gly Asp Asp Phe Asn Pro Glu Glu
                85                  90                  95

Leu Ile Ile Pro Ile Asn Leu Ala Tyr His Tyr Phe Asn Ile Ala Ile
                100                 105                 110

Ser Asp Phe Leu Ile Ala His Pro Glu Tyr Gln Lys Lys Cys Lys Glu
            115                 120                 125

Ile Gln Lys Thr Tyr Ser Gln Thr Asn Cys Ser Leu His Glu Thr
            130                 135                 140
```

(2) INFORMATION FOR SEQ ID NO: 40:

(i) SEQUENCE CHARACTERISTICS:
    (A) LENGTH: 833 acides amin,s
    (B) TYPE: acide amin,
    (C) STRANDEDNESS: single
    (D) TOPOLOGY: linear (ii) MOLECULE TYPE: peptide (ix) FEATURE:
    (A) NAME/KEY: Peptide
    (B) LOCATION:1..833

(xi) SEQUENCE DESCRIPTION: SEQ ID NO: 40:

```
Val Leu Lys Thr Pro Pro Thr Leu Ala Ala Glu Leu Ser Gly Lys Thr
1               5                   10                  15

Gly Val Ser Ile Ser Ala Pro Tyr Ala Asn Glu Asn Ser Arg Ile Leu
            20                  25                  30

Leu Ser Thr Thr Asp Ile Ser Ser Glu Asn Gly Lys Ile Lys Ile Gln
            35                  40                  45

Ser Tyr Gly Asp Gln Tyr Tyr Tyr Ala Arg Gln Ser Glu Leu Tyr Thr
    50                  55                  60

Phe Glu Arg Arg Ser Tyr Lys Thr Gly Lys Trp Tyr Asn Arg Lys His
65                  70                  75                  80

Ile Thr Glu Val Lys Glu His Lys Asn Ala Lys Pro Asp Ala Val Asn
                85                  90                  95

Leu Ser Ala Ser Gln Gly Ile Asp Ile Lys Ser Gly Gly Ser Ile Asp
                100                 105                 110
```

```
Ala Tyr Ala Thr Ala Phe Asp Ala Pro Lys Gly Ser Ile Asn Ile Glu
            115                 120                 125

Ala Gly Arg Lys Leu Thr Leu Tyr Ala Val Glu Glu Leu Asn Tyr Asp
        130                 135                 140

Lys Leu Asp Ser Gln Lys Arg Arg Phe Leu Gly Ile Ser Tyr Ser
145                 150                 155                 160

Lys Ala His Asp Thr Thr Thr Gln Val Met Lys Thr Ala Leu Pro Ser
                165                 170                 175

Arg Val Val Ala Glu Ser Ala Asn Leu Gln Ser Gly Trp Asp Thr Lys
            180                 185                 190

Leu Gln Gly Thr Gln Phe Glu Thr Thr Leu Gly Gly Ala Thr Ile Arg
        195                 200                 205

Ala Gly Val Gly Glu Gln Ala Arg Ala Asp Ala Lys Ile Ile Leu Glu
    210                 215                 220

Gly Ile Lys Ser Ser Ile His Thr Glu Thr Val Ser Ser Ser Lys Ser
225                 230                 235                 240

Thr Leu Trp Gln Lys Gln Ala Gly Arg Gly Ser Asn Ile Glu Thr Leu
                245                 250                 255

Gln Leu Pro Ser Phe Thr Gly Pro Val Ala Pro Val Leu Ser Ala Pro
            260                 265                 270

Gly Gly Tyr Ile Val Asp Ile Pro Lys Gly Asn Leu Lys Thr Gln Ile
        275                 280                 285

Glu Thr Leu Thr Lys Gln Pro Glu Tyr Ala Tyr Leu Lys Gln Leu Gln
    290                 295                 300

Val Ala Lys Asn Ile Asn Trp Asn Gln Val Gln Leu Ala Tyr Asp Lys
305                 310                 315                 320

Trp Asp Tyr Lys Gln Glu Gly Met Thr Pro Ala Ala Ala Ala Val Val
                325                 330                 335

Val Ile Val Val Thr Val Leu Thr Tyr Gly Ala Leu Ser Ala Pro Ala
            340                 345                 350

Ala Ala Gly Thr Ala Gly Ala Ala Gly Ala Gly Ala Gly Gly Ala Ala
        355                 360                 365

Ala Gly Thr Ala Ala Gly Thr Gly Val Ala Ala Gly Thr Ala Ala Thr
    370                 375                 380

Thr Gly Val Ala Ala Gly Thr Ser Ala Ala Ala Ile Thr Thr Ala Ala
385                 390                 395                 400

Gly Lys Ala Ala Leu Ala Ser Leu Ala Ser Gln Ala Ala Val Ser Leu
                405                 410                 415

Ile Asn Asn Lys Gly Asp Ile Asn His Thr Leu Lys Glu Leu Gly Lys
            420                 425                 430

Ser Ser Thr Val Arg Gln Ala Ala Thr Ala Ala Val Thr Ala Gly Val
        435                 440                 445

Leu Gln Gly Ile Ser Gly Leu Asn Thr Gln Ala Ala Glu Ala Val Ser
    450                 455                 460

Lys His Phe His Ser Pro Ala Ala Gly Lys Leu Thr Ala Asn Leu Ile
465                 470                 475                 480

Asn Ser Thr Ala Ala Ala Ser Val His Thr Ala Ile Asn Gly Gly Ser
                485                 490                 495

Leu Lys Asp Asn Leu Gly Asp Ala Ala Leu Gly Ala Ile Val Ser Thr
            500                 505                 510

Val His Gly Glu Val Ala Ser Lys Ile Lys Phe Asn Leu Ser Glu Asp
        515                 520                 525
```

```
Tyr Ile Ala His Lys Ile Ala His Ala Val Ala Gly Cys Ala Ser Ala
    530                 535                 540

Val Ala Asn Lys Gly Lys Cys Arg Asp Gly Ala Ile Gly Ala Ala Val
545                 550                 555                 560

Gly Glu Met Val Gly Glu Thr Leu Leu Asp Gly Arg Asp Val Gly Lys
                565                 570                 575

Leu Ser Pro Gln Glu Arg Gln Lys Val Ile Ala Tyr Ser Gln Ile Ile
            580                 585                 590

Ala Gly Ser Ala Val Ala Leu Val Lys Gly Asp Val Asn Thr Ala Val
        595                 600                 605

Asn Ala Ala Thr Val Ala Val Glu Asn Asn Ser Leu Leu Ala Arg Arg
610                 615                 620

Arg Val Asn Ile Arg Trp Thr Pro Arg Gln Glu Leu Glu His Glu Tyr
625                 630                 635                 640

Ala Ile Leu Glu Ile Gln Ala Ile Thr Asn Gln Ile Arg Arg Leu Asp
                645                 650                 655

Pro Lys Phe Asn Gly Ile Ala Ile Leu Arg Thr Pro Gly Glu Pro Trp
            660                 665                 670

Thr Arg His Asp Val Gln Thr Tyr Arg Gln Tyr Asn Gln Leu Arg
        675                 680                 685

Glu Ser Arg Gly Phe Ala Val Glu Pro Ile Tyr Arg Ile Arg Ile Asn
690                 695                 700

Asn Gly Asn Glu Phe Asn Arg Ile Met Ser Ser Lys Tyr Pro Tyr Asn
705                 710                 715                 720

Glu Leu Tyr Val Ala Asn Pro Lys Ser Ala Thr Gly Tyr Phe Arg Val
                725                 730                 735

Asp Ser Tyr Asp Pro Ala Thr Arg Glu Ile Ile Ser Arg Lys Phe Thr
            740                 745                 750

Gln Phe Ser Gln Ile Gln Glu Ser Thr Gly Ile Gly Tyr Ile Lys Glu
        755                 760                 765

Ala Val Arg Lys Tyr Ser Pro Gly Thr Val Ile Ser Asn Val Pro Ser
770                 775                 780

Thr Pro Thr Thr Ile Arg Gly Arg Lys Leu Glu Gly Lys Leu Ile Leu
785                 790                 795                 800

Glu Val Pro Ala Gln Val Asn Pro Ile Pro Gln Ser Val Leu Arg Ala
                805                 810                 815

Ala Gln Glu Glu Asn Val Ile Ile Arg Asp Thr Thr Gly Arg Ile Tyr
            820                 825                 830

Lys
```

(2) INFORMATION FOR SEQ ID NO: 41:

(i) SEQUENCE CHARACTERISTICS:
        (A) LENGTH: 664 acides amin,s
        (B) TYPE: acide amin,
        (D) TOPOLOGY: linear (ii) MOLECULE TYPE: protein (xi) SEQUENCE DESCRIPTION: SEQ ID NO: 41:

```
Val leu Lys Thr Pro Pro Thr Leu Ala Ala Glu leu Ser Gly Lys Thr
 1               5                  10                  15

Gly Val Ser Ile Ser Ala Pro Tyr Ala Asn Glu Asn Ser Arg Ile Leu
 20                  25                  30

Leu Ser Thr Thr Asp Ile Ser Ser Glu Asn Gly Lys Ile Lys Ile Gln
 35              40                  45
```

```
Ser Tyr Gly Asp Gln Tyr Tyr Tyr Ala Arg Gln Ser Glu Leu Tyr Thr
 50             55                 60

Phe Glu Arg Arg Ser Tyr Lys Thr Gly Lys Trp Tyr Asn Arg Lys His
 65         70             75                 80

Ile Thr Glu Val Lys Glu His Lys Asn Ala Lys pro Asp Ala Val Asn
             85             90             95

Leu Ser Ala Ser Gln Gly Ile Asp Ile Lys Ser Gly Gly Ser Ile Asp
100             105            110

Ala Tyr Ala Thr Ala Phe Asp Ala Pro Lys Gly Ser Ile Asn Ile Glu
115             120             125

Ala GlyArg Lys Leu Thr leu Tyr Ala Val Glu Glu Leu Asn Tyr Asp
130    135              140

Lys leu Asp Ser Gln Lys Arg Arg Arg Phe Leu Gly Ile Ser Tyr Ser
145          150             155             160

Lys Ala His Asp Thr Thr Thr Gln Val Met Lys Thr Ala Leu Pro Ser
                 165                 170                 175

Arg Val Val Ala Glu Ser Ala Asn Leu Gln Ser Gly Trp Asp Thr Lys
                 180                 185                 190

Leu Gln Gly Thr Gln Phe Glu Thr Thr Leu Gly Gly Ala Thr Ile Arg
                 195                 200                 205

Ala Gly Val Gly Glu Gln Ala Arg Ala Asp Ala Lys Ile Ile Leu Glu
                 210                 215                 220

Gly Ile Lys Ser Ser Ile His Thr Glu Thr Val Ser Ser Lys Ser
225                 230                 235                 240

Thr Leu Trp Gln Lys Gln Ala Gly Arg Gly Ser Asn Ile Glu Thr Leu
                 245                 250                 255

Gln Leu Pro Ser Phe Thr Gly Pro Val Ala Pro Val Leu Ser Ala Pro
                 260                 265                 270

Gly Gly Tyr Ile Val Asp Ile Pro Lys Gly Asn Leu Lys Thr Gln Ile
                 275                 280                 285

Glu Thr Leu Thr Lys Gln Pro Glu Tyr Ala Tyr Leu Lys Gln Leu Gln
                 290                 295                 300

Val Ala Lys Asn Ile Asn Trp Asn Gln Val Gln Leu Ala Tyr Asp Lys
305                 310                 315                 320

Trp Asp Tyr Lys Gln Glu Gly Met Thr Pro Ala Ala Ala Val Val
                 325                 330                 335

Val Ile Val Val Thr Val Leu Thr Tyr Gly Ala Leu Ser Ala Pro Ala
                 340                 345                 350

Ala Ala Gly Thr Ala Gly Ala Ala Gly Ala Gly Ala Gly Ala Ala
                 355                 360                 365

Ala Gly Thr Ala Ala Gly Thr Gly Val Ala Ala Gly Thr Ala Ala Thr
                 370                 375                 380

Thr Gly Val Ala Ala Gly Thr Ser Ala Ala Ala Ile Thr Thr Ala Ala
385                 390                 395                 400

Gly Lys Ala Ala Leu Ala Ser Leu Ala Ser Gln Ala Ala Val Ser Leu
                 405                 410                 415

Ile Asn Asn Lys Gly Asp Ile Asn His Thr Leu Lys Glu Leu Gly Lys
                 420                 425                 430

Ser Ser Thr Val Arg Gln Ala Ala Thr Ala Ala Val Thr Ala Gly Val
                 435                 440                 445

Leu Gln Gly Ile Ser Gly Leu Asn Thr Gln Ala Ala Glu Ala Val Ser
                 450                 455                 460
```

```
Lys His Phe His Ser Pro Ala Ala Gly Lys Leu Thr Ala Asn Leu Ile
465                 470                 475                 480

Asn Ser Thr Ala Ala Ser Val His Thr Ala Ile Asn Gly Gly Ser
            485                 490                 495

Leu Lys Asp Asn Leu Gly Asp Ala Ala Leu Gly Ala Ile Val Ser Thr
            500                 505                 510

Val His Gly Glu Val Ala Ser Lys Ile Lys Phe Asn Leu Ser Glu Asp
            515                 520                 525

Tyr Ile Ala His Lys Ile Ala His Ala Val Ala Gly Cys Ala Ser Ala
            530                 535                 540

Val Ala Asn Lys Gly Lys Cys Arg Asp Gly Ala Ile Gly Ala Ala Val
545                 550                 555                 560

Gly Glu Met Val Gly Glu Thr Leu Leu Asp Gly Arg Asp Val Gly Lys
                565                 570                 575

Leu Ser Pro Gln Glu Arg Gln Lys Val Ile Ala Tyr Ser Gln Ile Ile
            580                 585                 590

Ala Gly Ser Ala Val Ala Leu Val Lys Gly Asp Val Asn Thr Ala Val
            595                 600                 605

Asn Ala Ala Thr Val Ala Val Glu Asn Asn Ser Leu Leu Ala Arg Arg
610                 615                 620

Arg Val Asn Ile Arg Trp Thr Pro Arg Gln Leu Glu His Glu Tyr
625                 630                 635                 640

Ala Ile Leu Glu Ile Gln Ala Ile Thr Asn Gln Ile Arg Arg Leu Asp
                645                 650                 655

Pro Lys Phe Asn Gly Ile Ala Ile Leu Arg Thr Pro Gly Glu Pro Trp
                660                 665                 670

Thr Arg His Asp Val Gln Thr Tyr Arg Gln Tyr Tyr Asn Gln Leu Arg
                675                 680                 685

Glu Ser Arg Gly Phe Ala Val Glu Pro Ile Tyr Arg Ile Arg Ile Asn
            690                 695                 700

Asn Gly Asn Glu Phe Asn Arg Ile Met Ser Ser Lys Tyr Pro Tyr Asn
705                 710                 715                 720

Glu Leu Tyr Val Ala Asn Pro Lys Ser Ala Thr Gly Tyr Phe Arg Val
                725                 730                 735

Asp Ser Tyr Asp Pro Ala Thr Arg Glu Ile Ile Ser Arg Lys Phe Thr
            740                 745                 750

Gln Phe Ser Gln Ile Gln Glu Ser Thr Gly Ile Gly Tyr Ile Lys Glu
            755                 760                 765

Ala Val Arg Lys Tyr Ser Pro Gly Thr Val Ile Ser Asn Val Pro Ser
770                 775                 780

Thr Pro Thr Thr Ile Arg Gly Arg Lys Leu Glu Gly Lys Leu Ile Leu
785                 790                 795                 800

Glu Val Pro Ala Gln Val Asn Pro Ile Pro Gln Ser Val Leu Arg Ala
                805                 810                 815

Ala Gln Glu Glu Asn Val Ile Ile Arg Asp Thr Thr Gly Arg Ile Tyr
            820                 825                 830

Lys (2) INFORMATION FOR SEQ ID NO: 42:

(i) SEQUENCE CHARACTERISTICS:
        (A) LENGTH: 162 acides amin,s
        (B) TYPE: acide amin,
        (C) STRANDEDNESS: single
```

```
        (D) TOPOLOGY: linear (ii) MOLECULE TYPE: peptide (ix) FEATURE:
        (A) NAME/KEY: Peptide
        (B) LOCATION:1..162

(xi) SEQUENCE DESCRIPTION: SEQ ID NO: 42:

Met Lys Lys Asp Ile Phe Tyr Cys Glu Gln Trp Ser Tyr Gly Tyr Lys
1               5                  10                  15

Arg Leu His Lys Pro Phe Ser Glu Lys Gln Ala Glu Glu Lys His Leu
            20                  25                  30

Lys Gly Glu Leu Tyr Thr Ala Val Ile Gly Ser Ala Thr Gln Pro Glu
        35                  40                  45

Tyr Val Ile Thr Leu Arg Glu Val Gly Phe Phe Ser Val Asn Phe
 50                  55                  60

Phe Asp Lys Phe Gly Arg Asp Tyr Leu Thr His Gln Phe Gln Lys Tyr
65                  70                  75                  80

Ser Asn Ser Asn Tyr Tyr Phe Leu Ser Met Ala Val Trp Arg Asp Tyr
                85                  90                  95

Ile Thr Leu Glu Ser His Asp Leu Ala Glu Gly Tyr Thr Tyr Phe Phe
            100                 105                 110

Asn Glu Asn Thr Asp Asp Cys Tyr Val Leu Lys Gln Asp Phe Ile Asn
        115                 120                 125

Asn Glu Arg Tyr Glu Lys Thr Glu Leu Tyr Ser Gln Lys Asp Lys Val
    130                 135                 140

Ile Leu Phe Pro Lys Phe Gly Glu Tyr Asp Leu Val Leu Asn Pro Asp
145                 150                 155                 160

Ile Ile (2) INFORMATION FOR SEQ ID NO: 43:

(i) SEQUENCE CHARACTERISTICS:
        (A) LENGTH: 90 acides amin,s
        (B) TYPE: acide amin,
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..90

(xi) SEQUENCE DESCRIPTION: SEQ ID NO: 43:

Met Asn Lys Arg Met Lys Met Cys Pro Ala Cys Gln Gln Gly Tyr Leu
1               5                  10                  15

Tyr His Ser Lys Pro Lys Tyr Leu His Asp Glu Ile Ile Leu Cys Asp
            20                  25                  30

Glu Cys Asp Ala Val Trp Leu Lys Gly Met Asn Ile Phe Tyr Gly Glu
        35                  40                  45

Tyr Glu Lys Asp Phe Tyr Ser Tyr Val Pro Phe Met Glu Ser Gln Gly
    50                  55                  60

Ile Thr Ser Glu Cys Ile Trp Glu Gly Asp Leu Phe Asp His Pro Tyr
65                  70                  75                  80

Tyr Glu Asp Glu Asn Ser Asn Asp Met Asp
                85                  90

(2) INFORMATION FOR SEQ ID NO: 44:
```

```
    (i) SEQUENCE CHARACTERISTICS:
        (A) LENGTH: 313 acides amin,s
        (B) TYPE: acide amin,
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..313

(xi) SEQUENCE DESCRIPTION: SEQ ID NO: 44:

Met Ser Ala Thr Glu Ile Glu Lys Ala Lys Ala Lys Ile Thr Ala Tyr
1               5                  10                  15

Ser Lys Leu Val Ala Gly Thr Ala Ser Ala Val Val Gly Gly Asp Val
            20                  25                  30

Asn Thr Ala Ala Asn Ala Ala Gln Ile Ala Val Glu Asn Asn Thr Leu
        35                  40                  45

Tyr Pro Arg Cys Val Gly Ala Lys Cys Asp Glu Phe Gln Lys Glu Gln
    50                  55                  60

Gln Lys Trp Ile Arg Glu Asn Pro Glu Glu Tyr Arg Glu Val Leu Leu
65                  70                  75                  80

Phe Gln Thr Gly Phe Ile Pro Ile Ile Gly Asp Ile Gln Ser Phe Val
                85                  90                  95

Gln Ala Gln Thr Ala Ala Asp His Leu Phe Ala Leu Leu Gly Val Val
            100                 105                 110

Pro Gly Ile Gly Glu Ser Ile Gln Ala Tyr Lys Val Ala Lys Ala Ala
        115                 120                 125

Lys Asn Leu Gln Gly Met Lys Lys Ala Leu Asp Lys Ala Ala Thr Val
130                 135                 140

Ala Thr Ala Gln Gly Tyr Val Ser Lys Thr Lys Ile Lys Ile Gly Gln
145                 150                 155                 160

Thr Glu Leu Arg Val Thr Ala Ala Thr Asp Lys Gln Leu Leu Lys Ala
                165                 170                 175

Ile Gly Glu Gly Arg Asp Thr Thr Gly Lys Met Thr Glu Gln Leu Phe
            180                 185                 190

Asp Ser Leu Ala Lys Gln Asn Gly Phe Arg Val Leu Ser Gly Gly Lys
        195                 200                 205

Tyr Gly Gly Asn Asn Gly Phe Asp His Val Trp Gln Ala Ala Asp Gly
    210                 215                 220

Ser Val Val Leu Ile Val Glu Ser Lys Gln Ile Arg Asn Gly Thr Val
225                 230                 235                 240

Gln Leu Asn Pro Asn Gly Ala Gly Gly Tyr Thr Gln Met Ser Glu Asp
                245                 250                 255

Trp Ile Arg Gln Val Leu Asp Gln Leu Pro Asp Gly Ser Pro Ala Lys
            260                 265                 270

Ala Ala Val Phe Lys Ala Asn Lys Asn Gly Thr Leu Lys Thr Ala Ile
        275                 280                 285

Ala Gly Val Asp Arg Gln Thr Gly Lys Ala Val Ile Leu Pro Val Lys
    290                 295                 300

Val Pro Ser Lys Thr Asn Ile Arg Arg
305                 310

(2) INFORMATION FOR SEQ ID NO: 45:

(i) SEQUENCE CHARACTERISTICS:
```

(A) LENGTH: 311 acides aminés
        (B) TYPE: acide aminé
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..311

(xi) SEQUENCE DESCRIPTION: SEQ ID NO: 45:

```
Met Gly His Asn Met Met Thr Thr Gln Lys Trp Tyr Glu His Ile Thr
1               5                   10                  15

Asn Val Ile Ile Gly Asn Thr Ala Asn Phe Asn Ser Gly Cys Leu Asp
            20                  25                  30

Ser Ile Asp Tyr Val Asp Glu Arg Lys Gly Val Pro Leu Ala Ala Met
        35                  40                  45

Gln His Ile Phe Met Asp Val Arg Ala Ala Ser His Ala Tyr Leu
    50                  55                  60

Phe Glu His Asp Leu Lys Lys Phe Lys Gln Tyr Ala Tyr Val Ala Gly
65                  70                  75                  80

Lys Leu Gly Val Leu Leu Ser Val Asn Ser Thr Asp Pro Glu Pro Phe
                85                  90                  95

Phe Phe Pro Cys Asp Met Leu Asn Ile Gln Asn Pro Met Phe Leu Met
            100                 105                 110

Leu Met Ser Asp Ser Pro Gln Leu Arg Glu Phe Leu Val Arg Asn Ile
        115                 120                 125

Asp Asn Ile Ala Asn Asp Thr Glu Ala Phe Ile Asn Arg Tyr Asp Leu
    130                 135                 140

Asn Arg His Met Ile Tyr Asn Thr Leu Leu Met Val Glu Gly Lys Gln
145                 150                 155                 160

Leu Asp Arg Leu Lys Gln Arg Ser Glu Lys Val Leu Ala His Pro Thr
                165                 170                 175

Pro Ser Lys Trp Leu Gln Lys Arg Leu Tyr Asp Tyr Arg Phe Phe Leu
            180                 185                 190

Ala Phe Ala Glu Gln Asp Ala Glu Ala Met Lys Ala Ala Leu Glu Pro
        195                 200                 205

Leu Phe Asp Lys Lys Thr Ala Arg Met Ala Ala Lys Glu Thr Leu Ser
    210                 215                 220

Tyr Phe Asp Phe Tyr Leu Gln Pro Gln Ile Val Thr Tyr Ala Lys Ile
225                 230                 235                 240

Ala Ser Met His Gly Phe Asp Leu Gly Ile Asp Gln Glu Ile Ser Pro
                245                 250                 255

Arg Asp Leu Ile Val Tyr Asp Pro Leu Pro Ala Asp Glu Tyr Gln Asp
            260                 265                 270

Ile Phe Asp Phe Met Lys Gln Tyr Asp Leu Ser Tyr Pro Tyr Glu Tyr
        275                 280                 285

Leu Gln Asp Trp Ile Asp Tyr Tyr Thr Phe Lys Thr Asp Lys Leu Val
    290                 295                 300

Phe Gly Asn Ala Lys Arg Glu
305                 310
```

(2) INFORMATION FOR SEQ ID NO: 46:

(i) SEQUENCE CHARACTERISTICS:
        (A) LENGTH: 21 base pairs
        (B) TYPE: nucleotide

```
        (C) STRANDEDNESS: single
        (D) TOPOLOGY: linear (ii) MOLECULE TYPE: DNA (genomic)

(xi) SEQUENCE DESCRIPTION: SEQ ID NO: 46:

GCCACCGGTA CGGAAACTGA A                                             21

(2) INFORMATION FOR SEQ ID NO: 47:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

CCTGAATTCA TGTCTATTCC ATTTTGAAGA                                    30

(2) INFORMATION FOR SEQ ID NO: 48:

(i) SEQUENCE CHARACTERISTICS:
        (A) LENGTH: 31 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

CCGAGATCTT TAACCCTTTG GGCTTAAGCG A                                  31

(2) INFORMATION FOR SEQ ID NO: 49:

(i) SEQUENCE CHARACTERISTICS:
        (A) LENGTH: 29 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

GGGAGATCTC CCGCTCGTGT TGTGCATTA                                     29

(2) INFORMATION FOR SEQ ID NO: 50:

(i) SEQUENCE CHARACTERISTICS:
        (A) LENGTH: 28 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO: 50:

AAGAGATCTG CAGCCAAGGC TCTCGAAA                                      28

(2) INFORMATION FOR SEQ ID NO: 51:

(i) SEQUENCE CHARACTERISTICS:
          (A) LENGTH: 26 base pairs
          (B) TYPE: nucleotide
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

GGGAGATCTC AGGCTGCCGC CGTTGA                                        26

(2) INFORMATION FOR SEQ ID NO: 52:

(i) SEQUENCE CHARACTERISTICS:
          (A) LENGTH: 28 base pairs
          (B) TYPE: nucleotide
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

GGGAGATCTC ACCCCAAGAA CGCCAAAA                                      28

(2) INFORMATION FOR SEQ ID NO: 53:

(i) SEQUENCE CHARACTERISTICS:
          (A) LENGTH: 31 base pairs
          (B) TYPE: nucleotide
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

GGGAGATCTG AACGTATAGT AATCTATCCA A                                  31

(2) INFORMATION FOR SEQ ID NO: 54:

(i) SEQUENCE CHARACTERISTICS:
          (A) LENGTH: 12 base pairs
          (B) TYPE: nucleotide
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

```
AGTGGCTCCT AG                                                    12

(2) INFORMATION FOR SEQ ID NO: 55:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

AGCACTCTCC AGCCTCTCAC CGAG                                       24

(2) INFORMATION FOR SEQ ID NO: 56:

(i) SEQUENCE CHARACTERISTICS:
        (A) LENGTH: 12 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

AGTGGCTCTT AA                                                    12

(2) INFORMATION FOR SEQ ID NO: 57:

(i) SEQUENCE CHARACTERISTICS:
        (A) LENGTH: 10 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

AGTGGCTGGC                                                       10

(2) INFORMATION FOR SEQ ID NO: 58:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:58:

AGCACTCTCC AGCCTCTCAC CGAC                                       24
```

(2) INFORMATION FOR SEQ ID NO: 59:

(i) SEQUENCE CHARACTERISTICS:
        (A) LENGTH: 12 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

GTACTTGCCT AG                                                           12

(2) INFORMATION FOR SEQ ID NO: 60:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

ACCGACGTCG ACTATCCATG AACG                                              24

(2) INFORMATION FOR SEQ ID NO: 61:

(i) SEQUENCE CHARACTERISTICS:
        (A) LENGTH: 12 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

GTACTTGCTT AA                                                           12

(2) INFORMATION FOR SEQ ID NO: 62:

(i) SEQUENCE CHARACTERISTICS:
        (A) LENGTH: 10 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

GTACTTGGGC                                                              10

(2) INFORMATION FOR SEQ ID NO: 63:

(i) SEQUENCE CHARACTERISTICS:
    (A) LENGTH: 24 base pairs
    (B) TYPE: nucleotide
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

ACCGACGTCG ACTATCCATG AACC                                              24

(2) INFORMATION FOR SEQ ID NO:64:

(i) SEQUENCE CHARACTERISTICS:
    (A) LENGTH: 12 base pairs
    (B) TYPE: nucleotide
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

AATTCTCCCT CG                                                           12

(2) INFORMATION FOR SEQ ID NO:65:

(i) SEQUENCE CHARACTERISTICS:
    (A) LENGTH: 24 base pairs
    (B) TYPE: nucleotide
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

AGGCAACTGT GCTATCCGAG GGAG                                              24

(2) INFORMATION FOR SEQ ID NO: 66:

(i) SEQUENCE CHARACTERISTICS:
    (A) LENGTH: 140 base pairs
    (B) TYPE: nucleotide
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

GATCAACTTT TCCCTGTTTG TCCCATTACC GGTTTGAATG AACCGATTGC GCGCCGCGCG        60

TGTTGTTGGA CATTACCTGC GATTCAGACG GTACGATTGA CCACTACATC GAGGAGAACG       120

GCAATCAGGG TACAATGCTA                                                  140

(2) INFORMATION FOR SEQ ID NO: 67:

(i) SEQUENCE CHARACTERISTICS:
        (A) LENGTH: 192 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

GATCCGCGTA CTTGGTTTTT CATATTTTGC ATAGTCTTGT CGGTCGGGCA TCTTCCCCGA      60

CATCATCTAA ATTTGTCTTT ATTGGTTTTT ACGCCACTCA TTGCGGATAA ACAATATTCC     120

GCCTTGCCGT CGCGAATGTT CAAGCTAGCC TGCATCACCG TAATCAGGTT GCCCGTTACC     180

GAGCCTTCGA GA                                                         192

(2) INFORMATION FOR SEQ ID NO: 68:

(i) SEQUENCE CHARACTERISTICS:
        (A) LENGTH: 188 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

GATCCGGCTG CCCGACGCGC GCAAAATTGC CGCCGAGGAA AGCGCGCACA ACCACGACGG      60

CAAAACCAGC GTATGGCAAT ACAAACATCT CGTGTTCGGT ACGGCAGGCA TTTTCTGCTA     120

TGTCGGCGCG GAGGTGTCTA TCGGTTCGTT GATGGTCAAC GTATTGGGTT ATCTGAAAGG     180

GCTGGATC                                                              188

(2) INFORMATION FOR SEQ ID NO: 69:

(i) SEQUENCE CHARACTERISTICS:
        (A) LENGTH: 304 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

GATCCCCCAC TTTACCTCGG GCAGATTTTG CGCGTTCATT ACAATAGCGT ATTTATGCGT      60

TTGCGTTTGC GCTTGCCGCT GCCCCCCCCC CGCCGGTATG GGAAAACATC AATATGGCGG     120

TATAAAGCGC GGTATGGCGG AAAACCTGCC GTTTCCAAGT TTTATTCATC TTTTATTCCT     180

TGAGTTTGCC TTCACGGGAC GGGGCGGCGC GCGGAACGCG GGGTTCGGTA AACCGCCCGA     240

TTCCGCGCCC GCCGAATTGC TGATTGAAAA GCTTACTTCC CCATTTTAAC TTTGCACACT     300

GATC                                                                  304

(2) INFORMATION FOR SEQ ID NO: 70:

(i) SEQUENCE CHARACTERISTICS:
        (A) LENGTH: 243 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

GATCAGACCC ATTTTCAGCG CACCGTAAGC GCGGATTTTC TCGAATTTTT CCAAAGCTGC      60

GGCATCGTTG TTGATGTCGT CTTGCAACTC TTTGCCCGTG TAGCCCAAGT CGGCGGCATT     120

CAGGAAAACG GTCGGAATGC CGGCGTTGAT GAGCGTGGCT TTCAAACGGC CTATATTCGG     180

CACATCAATT TCATCGACCA AATTGCCGGT TGGGAACATA CTGCCTTCGC CGTCGGCTGG     240

ATC                                                                    243

(2) INFORMATION FOR SEQ ID NO:71:

(i) SEQUENCE CHARACTERISTICS:
        (A) LENGTH: 236 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

CGGCGGCGTA GTCCGCCGCG ACAGCGTTAC CATAAGCGGG ACAGACTACA CCCCTTTATC      60

TAACCCGCAA AGTTTGGATA CGGAATTAAA ATGGTTGCTT CAAGAAGCTC CCGAAATAGA     120

AAATCCTTTC GACCGCGCCG TTTATCTCCA TAATAATTTG GCGTATCTTC AATATTTTAA     180

AGATTGCAAT AAACGTACTG CCAGAAACTG CATGACCTTG TCGCTGATGC GCTCCG        236

(2) INFORMATION FOR SEQ ID NO: 72:

(i) SEQUENCE CHARACTERISTICS:
        (A) LENGTH: 280 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

CGGTCAATCA CAAGAAAGTC AGCCGTCTGA TGGCGAAGAC GGGGCTGAAG GCAGTGATAT      60

GGCGGCGCAA ATACCGCTCG TTCAAAGGAG AAGTCGGCAA AATTGCGCCG AATATCCTGC     120

GACGCTGTTT CCATGCAGAA AAGCCGAATG AGAAATGGGT AACGGACGTT GCCGAGTTCA     180

ATGTAGGCGG AGAAAAGATA TACCTTTCTC CGATTATGGA TTTGTTTAAC GGGGAAATCG     240

TCAGTTACCG TATTCAGACC CGCCCGACTT TCGATTTGGC                           280

(2) INFORMATION FOR SEQ ID NO: 73:

(i) SEQUENCE CHARACTERISTICS:
        (A) LENGTH: 120 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

CGGTCAGAAA CAGGCAAGGT AATGAAAATG CCTGAGGCAC GGACTGTGCT GCGAACGAAA    60

ACTCCTTACC GAAGTCTTCT ATACCCAGGC TCAATAGCCG CTCAAGGAGA GAGCTATCAT   120

(2) INFORMATION FOR SEQ ID NO: 74:

(i) SEQUENCE CHARACTERISTICS:
        (A) LENGTH: 120 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 74:

CGGTCAGAAA CAGGCAAGGT AATGAAAATG CCTGAGGCAC GGACTGTGCT GCGAACGAAA    60

ACTCCTTACC GAAGTCTTCT ATACCCAGGC TCAATAGCCG CTCAAGGAGA GAGCTATCAT   120

(2) INFORMATION FOR SEQ ID NO: 75:

(i) SEQUENCE CHARACTERISTICS:
        (A) LENGTH: 152 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

CGGTGTTTTT CTTAACAATT CGCCGACTTC ATGGCGATAT TTAAGTGACA GTTGCTCCGC    60

CCACGCAGTT GCGCCGAACT CAGCACCACG ACATTATACT GATTATGCAC ATCGGCAAGA   120

TCAAACTGAC CTATCGTAGT ATCGCAGACT GT                                 152

(2) INFORMATION FOR SEQ ID NO:76:

(i) SEQUENCE CHARACTERISTICS:
        (A) LENGTH: 381 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 76:

```
CGGGAGGTTT TGTGCATCCT GATACCGATC GGTTGTTGTT GCTCAAAGGA CAGAAGGCCG      60

CTGATAAACG AGATTACCTG TTTGTCGCTA TTGACGATTT TTATACTCTG CCATTTTGCC     120

AGACAAAACC GCAGACAGTG CTGCCAAGTT TCTGACCGAA CATCTGGCCG ACCCCTGCTT     180

GTACCTGATT GAGTACGCTT ACTCTGACAA TGATAGGTAA TATAAAGAGC CGTCCAACAT     240

GCTTTCGGTG CAGTTTGTTA TGATAATGGG ATTGGTTGGA GGCTTGCCCG ATTTGCTTGT     300

CCGCAGACCA ACGGTAAGGC GGAGCGGGTT ATCCGTACCT TGATGGAGAT GTGGCATGAG     360

GAACAGTCGT TTGACAGACC G                                               381

(2) INFORMATION FOR SEQ ID NO:77:

(i) SEQUENCE CHARACTERISTICS:
        (A) LENGTH: 269 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

CGGAGCATAA AATCGTTATT AAAGATAATG GTATAGGAAC GAGCTTCGAT GAAATCAATG      60

ATTTTTATTT GAGAATCGGT CGGAACAGAA GGGAAGAAAA ACAAGCCTCC CCGTGCGGAA     120

GAATTCCAAC GGGTAAAAAA GGCCTTGGTA AATTGGCATT ATTCGGGCTT GGCAACAAAA     180

TTGAAATTTC TACTATCCAG GGAAACGAAA GGGTTACTTT TACTTTGGAT TATGCAGAGA     240

TTCGAAGAAG CAAGGGTATT TATCAACCG                                       269

(2) INFORMATION FOR SEQ ID NO:78:

(i) SEQUENCE CHARACTERISTICS:
        (A) LENGTH: 203 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

CGGATGAAAA CGGCATACGC GCCAAAGTAT TTACGAACAT CAAAGGCTTG AAGATACCGC      60

ACACCTACAT AGAAACGGAC GCGAAAAAGC TGCCGAAATC GACAGATGAG CAGCTTTCGG     120

CGCATGATAT GTACGAATGG ATAAAGAAGC CGAAAATAT CGGGTCTATT GTCATTGTAG     180

ATGAAGCTCA AGACGTATGG CCG                                             203

(2) INFORMATION FOR SEQ ID NO: 79:

(i) SEQUENCE CHARACTERISTICS:
        (A) LENGTH: 229 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO: 79:

CGGTTTCAGG TTGTCGCGAA GGCTCGGTAA CGGGCAACCT GATTACGGGT GATGCAGGCA      60

GCTTGAACAT TCGCGACGGC AAGGCGGAAT ATGTTTATCC GCAATGAGTG GCGTAAAAAC     120

CAATAAAGAC AAATTTAGAT GATGTCGGGG AAGATGCCCG ACCGACAAGA CTATGCAAAA    180

TATGAAAAAC CAAGTACGCG GATCAGGCAT GGATGCACGA TCCAATCCG               229

(2) INFORMATION FOR SEQ ID NO: 80:

(i) SEQUENCE CHARACTERISTICS:
        (A) LENGTH: 207 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

CGGGTCGCTT TATTTGTGC AGGCATTATT TTTCATTTTT GGCTTGACAG TTTGGAAATA      60

TTGTGTATCG GGGGGGGGTA TTTGCTGACG TAAAAAACTA TAAACGCCGC GCAAAATATG    120

GCTGACTATA TTATTGACTT TGATTTTGTC CTGCGCGGTG ATGGATAAAA TCGCCAGCGA    180

TAAAGAATTT GCGAGAACCT GATGCCG                                      207

(2) INFORMATION FOR SEQ ID NO: 81 :

(i) SEQUENCE CHARACTERISTICS:
        (A) LENGTH: 224 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 81:

CGGCAACGAT TTGAGCTATC GCGGTTACGA CATTCTGGAT TTGGCACAAA AATGCGAGTT     60

TGAAGAAGTC GCCCACCTGC TGATTCACGG CCATCTGCCC AACAAATTCG AGCTGGCCGC    120

TTATAAAACC AAGCTCAAAT CCATGCGCGG CCTGCCTATC CGTGTGATTA AAGTTTTGGA    180

AAGCCTGCCT GCACATACCC ATCCGATGGA CGTAATGCGT ACCG                    224

(2) INFORMATION FOR SEQ ID NO: 82:

(i) SEQUENCE CHARACTERISTICS:
        (A) LENGTH: 212 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

| CGGGAACAGC CATTGCCCAC GCCCACGCCC CCCAAGAAAG ACGGAAACTA CTGCCTAAAT | 60 |
| TTTCGGCAAT CAAGTTGACG ATTAAAGGGT TGGGGGCAGT TGCAGTAATA AACATAGCCG | 120 |
| ACGAAATGGG ATTGGAATGA TAGTTGACCA AAGCCAAATA TTTACCCATC TTGCCTTCTG | 180 |
| TGCCTTTTGC GGGATTGGAG CCGTAACTGC CG | 212 |

(2) INFORMATION FOR SEQ ID NO:83:

(i) SEQUENCE CHARACTERISTICS:
        (A) LENGTH: 353 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

| CGGGAATTCT GAGCAGAATG AAAGAAAGCA GGCTTGATAA TTTCATAAAG TTATTGGAAG | 60 |
| AAAAAGGATT TACCGTCCAT TTCGGTATTC ACAATACGGC TGATTACGGA ATTCCCCAAA | 120 |
| GCCGTAAAAG ATTTACGTTA ATTGCAAACA GAATAACCAA AGAAAAGCTG GAACCAGTCA | 180 |
| AGTATTCGGG CAAACGGCTT ACGGTAGCCG ATGTTTTGGG AATGGAAATG GCTTTCCCAA | 240 |
| CATTATTGCA GGACACCAAG ACGAAACGGA TTTTATGCAT AGCTGTGCGG GAATTATCTG | 300 |
| ATATCACTTG AACGATTGGC TTGATACCTA AAAACGGAGG AACCGTTGGC TTT | 353 |

(2) INFORMATION FOR SEQ ID NO: 84:

(i) SEQUENCE CHARACTERISTICS:
        (A) LENGTH: 308 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

| AATTCCGTAT CCAAACTTTG CGGGTTAGAT AAAGGGGTGT AGTCTGTCCC GCTTATGGTA | 60 |
| ACGCTGTCGC GGCGGACTAC GCCCGGAGCC TTTTTCCAGT AAGTTTTCGG AAATCAGGCT | 120 |
| GTGGGTGGTT TTTAAGAAAT CCAACCAGTC AAACGGCTCG GGGCTGTCCA AACCGGACAC | 180 |
| AGGTGCCGGT AACTTTCCCT CAGGTTGATT AACATTACGG CATCCGAATA TAACTTCCCG | 240 |
| CCTGCGGTTT GCCCGAGTTT AAGCAATGCC TGCGTATCGT ATTGATTATA AAGTGTTTCC | 300 |
| TTCCAATT | 308 |

(2) INFORMATION FOR SEQ ID NO: 85:

(i) SEQUENCE CHARACTERISTICS:
        (A) LENGTH: 104 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:

AATTCGTGTG CCGCGTCGAC AAACCGCTGA CGTAGCGGAT GTCTCATGCC ACGTTTCAAA      60

GCAGGTTGAT GGCGGTTAGC AACCCTCTGA TTTCACTGGG ATAT      104

(2) INFORMATION FOR SEQ ID NO: 86:

(i) SEQUENCE CHARACTERISTICS:
        (A) LENGTH: 89 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

AATTGCGTAG AGTGGGCTTC AGCCACGTTT TTTCTTTTTC GGTCGTTGAT TGGTGGGCTG      60

AACCACTTGT TTCGGAAATC CGTATCATG      89

(2) INFORMATION FOR SEQ ID NO: 87:

(i) SEQUENCE CHARACTERISTICS:
        (A) LENGTH: 273 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

AATTTCCACC TATGCCCTAC GCAGCGATTA TCCGTGGTTT ACCCAAAGGG TGATTATGGC      60

AAAAGCGCGG GGTTGAGCGA CCGCCTTTTG TTGCCGGCGT TCAAACGGGT TTTGATAGGA      120

AATGCAGGCA CGAAGCCTCG GCTGATTGTG ATGCACCTGA TGGGTTCGCA CAGTGATTTT      180

TGCACACGTT TGGATAAGGA TGCGCGGCGG TTTCAGTATC AAACTGAAAA AATATCCTGC      240

TATGTTTCCA TCAATCGCGC AAACCGATAA ATT      273

(2) INFORMATION FOR SEQ ID NO: 88:

(i) SEQUENCE CHARACTERISTICS:
        (A) LENGTH: 270 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

AATTCTTCCG CACGGGGAGG CTTGTTTTTC TTCCCTTCTG TTCCGACCGA TTCTCAAATA      60

AAAATCATTG ATTTCATCGA AGTTCATTCC TATACCATTA TCTTTAATAA CGATTTTATG      120

CTCCGGTTTA TCGAATAACC TAACTTCCAC TTCCGTAGCA CATGCATCGT AGGCATTCGC      180

TATCAACTCG GCAATCGCAG GAACAGTGTG CGAATACAAT CTTTACACCC AAATGTTCGA      240

TTACGGTTGG CTCGAAACTC AATTTCAATT                                      270

(2) INFORMATION FOR SEQ ID NO: 89:

(i) SEQUENCE CHARACTERISTICS:
        (A) LENGTH: 267 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

AATTATGAAC ACACGCATCA TCGTTTCGGC TGCGTTCGTT GCGTTGGCAT TAGCAGGTTG       60

CGGCTCAATC AATAATGTAA CCGTTTCCGA CCAGAAACTT CAGGAACGTG CCGCGTTTGC      120

CTTGGGCGTC ACCAATGCCG TAAAAATCAG CAACCGCAGC AATGAAGGCA TACGCATCAA      180

CTTTACCGCA ACTGTGGGTA AGCGCGTGAC CAATGCTATG TTACCAGTGT AATCAGCACA      240

ATCGGCGTTA CCACTTCCGA TGCAATT                                         267

(2) INFORMATION FOR SEQ ID NO: 90:

(i) SEQUENCE CHARACTERISTICS:
        (A) LENGTH: 234 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

AATTTTTATT TGGTTCGTAG TCATTTTGTG CAACTGAACG ATATTCGTTT TCATCATTGC       60

TAACGTCTAG TGCCCATTGT GGCCCGTAAT AAGAGATTTC GTCTCCTTTT ACATGTTTGA      120

CGCTGACGGC ATACTGGGGA TCGATGACGG ATAATGTACG TCTGTTGACA TCTGCAACGC      180

TAAATCAATC ATCGGTATTG GATAATGCGT TGCCGATGTT TTGACTTGTA TGTT           234

(2) INFORMATION FOR SEQ ID NO: 91:

(i) SEQUENCE CHARACTERISTICS:
        (A) LENGTH: 295 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

AATTCGGCCG GCTGTGTCAA ATAATGCGTT ACTTTGGCCG GGTCTTGTTC TTTGTAAGTG       60

GTGGTCTTTT TTTGCGCGTT ATCCCCATCT GTTTGAGTGC ATAGCAAATG GTGGCTGCCG     120

TACAATCAAA TGTTTGGCGT TCATGCAGAT AGGCATCATG GTGTTGCCCA ATATATTGAG     180

CCGGTTTTTG CCTATCCGAT TTGACGGCAT TTAGACCGGT AACTTGATGT TTTAAGCTGC    240

CTGTTTGTTT AAAGGCGAAT CCACAAGTAA AGCGTGTTTC TTGACAGGTT AAACG    295

(2) INFORMATION FOR SEQ ID NO: 92:

(i) SEQUENCE CHARACTERISTICS:
        (A) LENGTH: 259 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

AATTGTGTAT ATCAAGTAGG ATGGGCATTT ATGCCTGACC TACAAAACCA AAAACAACCT    60

ACCACCCTTA ATCAACTCCA CAAACCCTCT TCAGACAACC TCGTTTTTTG AAAAACAATC    120

TGTAAACAGA TAACTGCTGA AGAATACCGT TGCCGAGCCC CAAAACCCGT ACTGCAACTT    180

TTATTGTGAA CTTCCCATTA TGAGAAAATC CCTTTTCGTC CTCTTTCTGT ATTCGTCCCT    240

ACTTACTGCC AGCGAAATT    259

(2) INFORMATION FOR SEQ ID NO: 93:

(i) SEQUENCE CHARACTERISTICS:
        (A) LENGTH: 379 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

AATTGCACCA CGCGATGATG GGTACGCCTC TGTTGCCATT GCGACCGCCG CCGCCGTGCC    60

CGGTACGCTG GTCAACCTTG CCGCGGCGGA ACGGGTAAAG AAGTGCGCTT CGGGCATCCT    120

TCCGGTACAT TGCGCGTCGG TGCAGCGCCG AATGTCAGGA CGGACAATGG ACGGCCACCA    180

AAGCGGTTAT GAGCCGCAGC GCACGCGTGA TGATGGAAGG TTGGGTCAGG GTGCCGGAAG    240

ATTGTTTTTA AATTGGACGG CGAACCGGTC TATTCGTATT GGCGTTATAC CGCCGCAAAG    300

GCAGACCTTG AAACTGGTGC GTGCCGTGCA GGGCATGTAC GGCTATGTGT GCGTGGCGGG    360

CGGATTTGAT GTGCGGAAT    379

(2) INFORMATION FOR SEQ ID NO: 94:

(i) SEQUENCE CHARACTERISTICS:
        (A) LENGTH: 308 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 94:

```
AATTTGTTGG GCAGATGGCC GTGAATCAGC AGGTGGGCGA CTTCTTCAAA CTCGCATTTT    60

TGTGCCAAAT CCAGAATGTC GTAACCGCGA TACGTCAAAT CGTTGCCGGT ACGCAACGGT   120

ACACAAAGCG GTATTACCGG CCGCAACGCC AGAAAGCGCA ACGGATTTTT AGGTTTGAGG   180

GTCGGGGTTT GAGTAGTTTC AGTCATGGTA TTTCTCCTTT GTGTTTTTAT GGGTTTCGGG   240

TTTTCAGACG ACCGATGCGG ATTTGTTGAA AGGCAGTCTG AAAGCGGTAA ATCATTTTTG   300

AAACAATT                                                            308

(2) INFORMATION FOR SEQ ID NO: 95:

(i) SEQUENCE CHARACTERISTICS:
        (A) LENGTH: 286 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

AATTCGGAGG AGCAGTACCG CCAAGCGTTG CTCGCCTATT CCGGCGGTGA TAAAACAGAC    60

GAGGGTATCC GCCTGATGCA ACAGAGCGAT TACGGCAACT TGTCCTACCA CATCCGTAAT   120

AAAAACATGC TTTTCATTTT TTCGGCAAGC AATGACGCAC AAGCTCAGCC CAACACAACT   180

GACCCTATTG CCATTTTATG AAAAAGACGC TCAAAAAGGC ATTATCACAG TTGCAGGCGT   240

AGACCGCAGT GGAGAAAAGT TCAATGGCTC CAACCATTGC GGAATT                  286

(2) INFORMATION FOR SEQ ID NO: 96:

(i) SEQUENCE CHARACTERISTICS:
        (A) LENGTH: 238 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

AATTTGGATA CGTTGGAAAA GGGATATTTG ATTGGGAATG GGATGAAGAT AAGCGTAGAT    60

GAGTTGGGGA AAAAGTGTT AGAACATATC GGTAAGAATG AACCGTTATT GTTGAAAAAT   120

CTACTGGTTA ACTTCAATCA GGGAAAACAT GAAGAAGTTA GGAAGTTGAT TTATCAGTTG   180

ATAGAGTTAG ATTTTCTGGA ACTTTTGTGA GGGATTCTAT GAAAAACTGG AAGCAATT     238

(2) INFORMATION FOR SEQ ID NO: 97:

(i) SEQUENCE CHARACTERISTICS:
        (A) LENGTH: 322 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

-continued (xi) SEQUENCE DESCRIPTION: SEQ ID NO: 97:

| | | | | | |
|---|---|---|---|---|---|
| AATTCGGCAC | GCAGGTTTTC | TAAAAAAAGG | CCGTTGATGA | CTTTGTCGAT | ATTGGCGGCT | 60 |
| TCGGTGTAGT | GCGCGCCCGC | TTCGGCCGCT | CTTGCGCGTC | CATGACGGAT | TGGAAGAGCG | 120 |
| TGCCGAAGAT | TTCTGGACTG | ATGTTGCGCC | AGTCGAAATT | GCCGACACGG | GAGGAATACC | 180 |
| TGCCAACAAG | AGTGCAGGCA | GCGTAATCAA | ACCACCCCA | CCCGCAATCG | CATCGATAAA | 240 |
| TCCGGCAATC | ATCGCAACCA | AACCCAAAGC | GAGTATTATG | TATAAATCTT | CCATGTTTCT | 300 |
| TAATCCTGTT | AACTTGCACC | AA | | | | 322 |

(2) INFORMATION FOR SEQ ID NO: 98:

(i) SEQUENCE CHARACTERISTICS:
      (A) LENGTH: 316 base pairs
      (B) TYPE: nucleotide
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

| | | | | | |
|---|---|---|---|---|---|
| AATTTGTCGG | CAATCTTCCC | GGGTCGCTTT | ATTTTGTGCA | GGCATTATTT | TTCATTTTTG | 60 |
| GCTTGACAGT | TTGGAGATAT | TGTGTATCGG | GGGGGGGTAT | TTGCTGACGT | AAAAAACTAT | 120 |
| AAACGCCGCA | GCAAAATATG | GCTGACTATA | TTATTGACTT | TGATTTTGTC | CTGCGCGGTG | 180 |
| ATGGATAAAA | TCGCCAGCGA | TAAAGATTTG | CGAGAACCTG | ATGCCGGCCT | GTTGTTGAAT | 240 |
| ATTTTCGACC | TGTAATTACG | ATTTGGCTTC | CGCGCCGGCA | CAATATGCCG | CCAAGCGGCG | 300 |
| CCCACATTTT | GGAAGC | | | | | 316 |

(2) INFORMATION FOR SEQ ID NO: 99:

(i) SEQUENCE CHARACTERISTICS:
      (A) LENGTH: 217 base pairs
      (B) TYPE: nucleotide
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

| | | | | | |
|---|---|---|---|---|---|
| AATTCGGACA | GTATGAATAC | AGCGGATTAA | TACAAGGTAA | GTTCATTACA | ACGGAAAAAC | 60 |
| CTTTAAAGAA | TAATATGAAA | GGTATTACCT | TGTTTGCCAA | CGGGAATGGT | AAATATGCCC | 120 |
| GAGTTTTTCA | CTGAATAGCG | AATCCAGCCA | TTTCTATTCA | TATTTGACTG | GATGGCTGAA | 180 |
| TGTGGACTTT | ATAGATAATG | ACGATGAAGA | TTTAATT | | | 217 |